US012600724B2

(12) United States Patent
Shen et al.

(10) Patent No.: US 12,600,724 B2
(45) Date of Patent: Apr. 14, 2026

(54) INDOLE ALKALOID AND PREPARATION METHOD AND USE THEREOF

(71) Applicants: NANJING UNIVERSITY OF CHINESE MEDICINE, Nanjing (CN); CHINA PHARMACEUTICAL UNIVERSITY, Nanjing (CN)

(72) Inventors: Xu Shen, Nanjing (CN); Sheng Jiang, Nanjing (CN); Kuojun Zhang, Nanjing (CN); Jiaying Wang, Nanjing (CN); He Tang, Nanjing (CN); Yujie Huang, Nanjing (CN); Tong Zhao, Nanjing (CN); Minyi Qian, Nanjing (CN)

(73) Assignees: NANJING UNIVERSITY OF CHINESE MEDICINE, Nanjing (CN); CHINA PHARMACEUTICAL UNIVERSITY, Nanjing (CN)

( * ) Notice: Subject to any disclaimer, the term of this patent is extended or adjusted under 35 U.S.C. 154(b) by 403 days.

(21) Appl. No.: 18/264,435

(22) PCT Filed: Nov. 9, 2022

(86) PCT No.: PCT/CN2022/130902
§ 371 (c)(1),
(2) Date: Aug. 7, 2023

(87) PCT Pub. No.: WO2023/216533
PCT Pub. Date: Nov. 16, 2023

(65) Prior Publication Data

US 2025/0011328 A1 Jan. 9, 2025

(30) Foreign Application Priority Data

May 9, 2022 (CN) ......................... 202210498643.8

(51) Int. Cl.
*A61P 3/10* (2006.01)
*A61K 31/4375* (2006.01)
(Continued)

(52) U.S. Cl.
CPC ........ *C07D 471/22* (2013.01); *A61K 31/4375* (2013.01); *A61P 11/00* (2018.01); *A61P 17/02* (2018.01); *A61P 25/02* (2018.01)

(58) Field of Classification Search
CPC .............. C07D 471/22; A61K 31/4375; A61K 31/765; A61K 38/00; A61P 11/00;
(Continued)

(56) References Cited

U.S. PATENT DOCUMENTS

2018/0016270 A1* 1/2018 Yuan .................... C07D 519/00

* cited by examiner

*Primary Examiner* — Taylor V Oh
(74) *Attorney, Agent, or Firm* — CBM PATENT CONSULTING, LLC

(57) ABSTRACT

A compound represented by formula (I) and a preparation method thereof, and a pharmaceutically acceptable salt thereof, a metabolic precursor thereof, a metabolite thereof, an isomer thereof or a prodrug thereof; experiments show that the indole alkaloid not only promotes axon growth of peripheral sensory neurons, improves the nerve conduction velocity and anesthesia symptom of diabetic rats, but also promotes healing of foot ulcer wounds of diabetic rats, thus having good therapeutic effects on diabetic complication peripheral neuropathy and diabetic feet; they also show that the indole alkaloid also obviously reduces a degree of pulmonary fibrosis induced by bleomycin in mice, and plays a role in protecting lung tissues.

13 Claims, 3 Drawing Sheets

(51) Int. Cl.
*A61P 11/00* (2006.01)
*A61P 17/02* (2006.01)
*A61P 25/02* (2006.01)
*C07D 471/22* (2006.01)

(58) Field of Classification Search
CPC .. A61P 17/02; A61P 25/02; A61P 3/10; Y02P 20/55; C07K 5/06139; C07K 5/0821; C08G 65/33396; C07B 2200/07
USPC .......................................................... 514/283
See application file for complete search history.

INDOLE ALKALOID AND PREPARATION METHOD AND USE THEREOF

TECHNICAL FIELD

The present invention belongs to the field of medicine and chemical synthesis, and particularly relates to an indole alkaloid and a preparation method thereof, a pharmaceutical composition, and use of the indole alkaloid as drugs for treating peripheral neuron axon injury and periphery related neuropathy and diabetic foot, and pulmonary fibrosis.

BACKGROUND

Diabetes is a serious worldwide disease. It is estimated that, by 2045, the number of diabetic patients will reach 629 Million. The diabetes has become the third non-infective disease that threatens human health and life after cardiovascular diseases and tumors. The diabetes has become an epidemic disease from a rare disease in China, and an average prevalence rate of the diabetes has soared from 0.67% to 11.6% in the past 30 years. If the diabetic patients do not receive effective control and treatment, they will be easily troubled by many diabetic complications, such as diabetic neuropathy, diabetic nephropathy, diabetic foot, and etc., accompanied by blindness, renal failure and even limb disability and death.

Diabetic Peripheral Neuropathy (DPN) is chronic diabetic neuropathy caused by long-term hyperglycemia with an incidence rate as high as 50% to 80%, which is the most common chronic diabetic complication. The diabetic peripheral neuropathy implicates motor nerve, sensory nerve and autonomic nerve, resulting in motor and sensory disorders. Clinically, vibration and thermal perception thresholds of diabetic peripheral neuropathy patients can be increased, which may develop into anesthesia with the degeneration of all fibers in a peripheral nerve. At present, diagnostic methods of the diabetic peripheral neuropathy are mainly sensory detection, electrophysiological detection, nerve fiber morphology examination, imaging examination and the like. However, there are a variety of clinical manifestations of the diabetic peripheral neuropathy, with different classification methods at home and abroad, complicated screening and examination methods, and different diagnostic criteria, so that the prevention and treatment of the diabetic peripheral neuropathy has always been a clinical difficulty. With the rapid development of science and technology, scientists have made a breakthrough in the study of the diabetic peripheral neuropathy, but there is still a lack of a specific drug to cure the diabetic peripheral neuropathy once and for all. Therefore, it is urgent to research and develop a new therapeutic strategy and a new compound.

Diabetic Foot (DF) is a lesion leading to diabetic angiopathy and (or) neuropathy and infection due to long-term hyperglycemia, and then leading to foot or lower limb tissue necrosis of the diabetic patients. The diabetic foot is one of the most serious diabetic complications and one of the main causes of disability and death of the diabetic patients, and is also a major public health problem causing a heavy burden on society. With the increase of the incidence rate of the diabetes, a number of patients suffering from the diabetic foot have also increased year by year. An incidence rate of the diabetic foot is as high as 8.1% among the diabetic patients over 50 years old in China. Unfortunately, the diabetic foot is very poor in prognosis, even has higher fatality rate and disability rate than most cancers (except a lung cancer, a pancreatic cancer, and the like). Moreover, the diabetic foot has a high treatment expense and needs long-term treatment, and clinically, foot ulcers of the patients are mainly healed by medical care to avoid a risk of amputation. However, the diabetic foot cannot be completely cured by the care, and is easy to relapse. Therefore, it is of great practical significance to study the pathogenesis of the diabetic foot and develop a novel effective therapeutic drug for the diabetic foot.

Pulmonary Fibrosis (PF) is a chronic, progressive and fatal lung disease, and is a terminal stage of many diseases, and the pathogenesis of the pulmonary fibrosis is still uncertain. The pulmonary fibrosis seriously affects a respiratory function of a human body, and is manifested as dry cough and progressive dyspnea (feeling a lack of air), and with the aggravation of illness and lung injury, the respiratory function of the patients continues to deteriorate. An incidence rate and a mortality rate of idiopathic pulmonary fibrosis are increasing year by year, an average life expectancy after diagnosis is only 2.8 years, and the mortality rate is higher than that of most tumors, thus being called a "tumor-like disease". COVID-19 patients may also suffer from pulmonary fibrosis after being cured. At present, pirfenidone, nidanib, oxygen therapy, invasive/noninvasive mechanical ventilation and lung transplantation are commonly used in the treatment of pulmonary fibrosis. However, these methods have a high expense and a non-obvious curative effect, and their wide application is limited by a shortage of transplant donors or an immune rejection reaction, and poor medical compliance of the patients. Therefore, it is very important to actively explore the pathogenesis of the pulmonary fibrosis and develop a new intervention drug.

Vincamine is a monoterpenoid indole alkaloid found in Madagascar Periwinkle Herb, which can increase cerebral blood flow, oxygen consumption and glucose utilization rate, and improve dementia and memory impairment. Vinpocetine is a vincamine derivative, which selectively increases cerebral blood flow; and can enhance and improve the supply of oxygen to the brain, promote metabolism, enhance the deformability of red blood cells, reduce blood viscosity, inhibit platelet aggregation and improve brain tissue metabolism. Vinpocetine is mainly used to treat sequelae of cerebral infarction, cerebral hemorrhage and cerebral arteriosclerosis. Vinpocetine is also used to treat retinal arteriosclerosis and vasospasm, deafness and vertigo in the elderly. However, like many natural products, vincamine and vinpocetine are faced with problems such as poor water solubility, unstable metabolism and short action time. According to the previous work, the vincamine has the potential to treat diabetic complications and pulmonary fibrosis diseases. Therefore, it is of great significance to find novel vincamine/vinpocetine derivatives for the treatment of diabetic complications and pulmonary fibrosis.

Polyethylene Glycol (PEG) is a water-soluble polyether with low molecular weight, which is obtained by stepwise addition polymerization of ethylene oxide with water or ethylene glycol. The polyethylene glycol with low molecular weight is a colorless, odorless and hygroscopic viscous liquid with both ether chains and hydroxyl groups in molecules thereof, so the polyethylene glycol with low molecular weight has unique solubility and good biocompatibility, and has very important application prospects in the fields of medicine, materials and engineering.

SUMMARY

The technical problem to be solved by the invention is that PEG is connected with vinpocetine by utilizing the characteristics of no toxicity and easy combination of the PEG, so as to overcome the poor water solubility of vinpocetine. The present invention provides an indole alkaloid, a preparation method, a pharmaceutical composition and use thereof. The indole alkaloid of the present invention has stable structure and good water solubility, and has good therapeutic effects on diabetic peripheral neuropathy, diabetic foot and pulmonary fibrosis.

The present invention solves the above technical problem by the following technical solutions.

The present invention provides a compound represented by formula I, or a pharmaceutically acceptable salt thereof, a metabolic precursor thereof, a metabolite thereof, an isomer thereof or a prodrug thereof, wherein a structure of the compound is shown as follows:

I

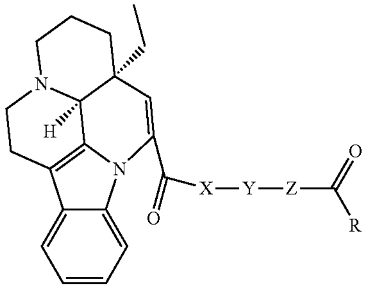

in the formula:

X is O or —NR$^1$;

R$^1$ is hydrogen, unsubstituted or R$^{1-1}$ substituted $C_{1-6}$ alkyl, $C_{6-10}$ aryl, $C_{3-10}$ cycloalkyl, 5-10 membered heteroaryl "containing 1 to 3 heteroatoms selected from one or more of N, O and S", or 4-10 membered heterocycloalkyl "containing 1 to 3 heteroatoms selected from one or more of N, O and S", and $C_{3-10}$ cycloalkyl-($C_{1-4}$ alkyl)- or $C_{6-12}$ aryl-($C_{1-4}$ alkyl)-;

R$^{1-1}$ is halogen or hydroxyl;

Y is —$(CH_2)$m-;

m is an integer from 1 to 6;

Z is a single bond,

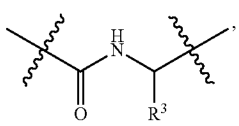,

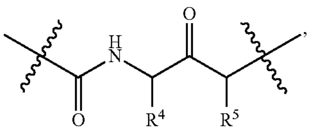,

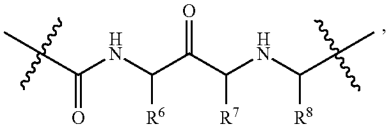,

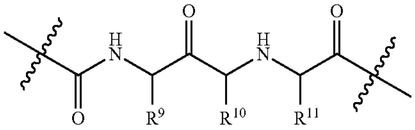

or

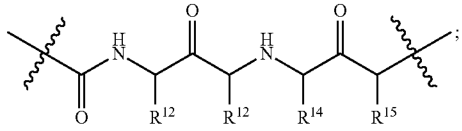;

R$^3$, R$^4$, R$^5$, R$^6$, R$^7$, R$^8$, R$^9$, R$^{10}$, R$^{11}$, R$^{12}$, R$^{13}$, R$^{14}$ and R$^{15}$ are each independently selected from hydrogen, unsubstituted or R$^{3-1}$ substituted $C_{1-6}$ alkyl, $C_{6-10}$ aryl, unsubstituted or R$^3$-2 substituted $C_{6-12}$ aryl-($C_{1-4}$ alkyl)-, heteroaryl, or heteroaryl-($C_{1-4}$ alkyl)-; and the heteroaryl is 5-10 membered heteroaryl "containing 1 to 3 heteroatoms selected from one or more of N, O and S";

R$^{3-1}$ is hydroxyl, carboxyl, amino, sulfhydryl, —(C═O)NR$^{3-1-1}$, or —NH(C═NH)$NH_2$;

R$^{3-1-1}$ is hydrogen or $C_{1-4}$ alkyl;

R$^{3-2}$ is halogen or hydroxyl;

R is hydrogen, $C_{1-6}$ alkoxy or

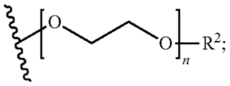;

R$^2$ is $C_{1-6}$ alkyl or hydrogen;

n is an integer from 0 to 500; and

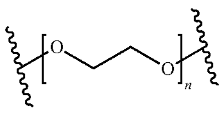

is polyethylene glycol with a linear, tree, star or hyperbranched structure comprising —$(OCH_2CH_2)_n$—.

I

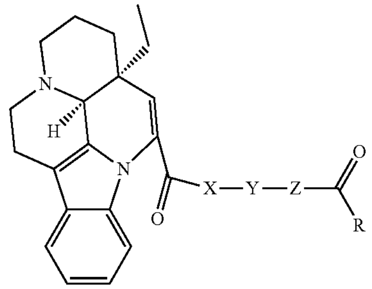

in the formula:

X is O or —NR$^1$;

R$^1$ is hydrogen, unsubstituted or R$^{1-1}$ substituted $C_{1-6}$ alkyl, $C_{6-10}$ aryl, $C_{3-10}$ cycloalkyl, 5-10 membered heteroaryl "containing 1 to 3 heteroatoms selected from one or more of N, O and S", or 4-10 membered heterocycloalkyl "containing 1 to 3 heteroatoms selected from one or more of N, O and S", and $C_{3-10}$ cycloalkyl-($C_{1-4}$ alkyl)- or $C_{6-12}$ aryl-($C_{1-4}$ alkyl)-;

R$^{1-1}$ is halogen or hydroxyl;

Y is —$(CH_2)$m-;

m is an integer from 1 to 6;

Z is a single bond,

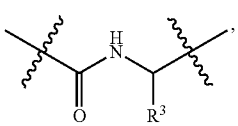,

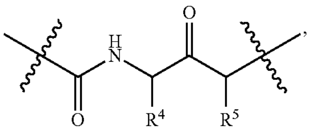,

-continued

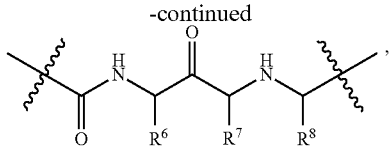

,

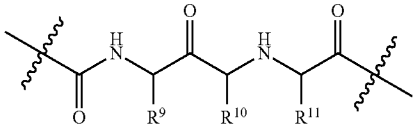

or

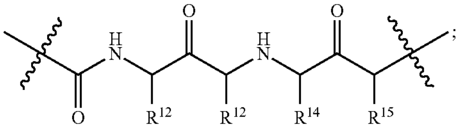

;

$R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from hydrogen, unsubstituted or $R^{3-1}$ substituted $C_{1-6}$ alkyl, $C_{6-10}$ aryl, unsubstituted or $R^3$-2 substituted $C_{6-12}$ aryl-($C_{1-4}$ alkyl)-, heteroaryl, or heteroaryl-($C_{1-4}$ alkyl)-; and the heteroaryl is 5-10 membered heteroaryl "containing 1 to 3 heteroatoms selected from one or more of N, O and S";

$R^{3-1}$ is hydroxyl, carboxyl, amino, sulfhydryl, —(C═O)$NR^{3-1-1}$, or —NH(C═NH)$NH_2$;

$R^{3-1-1}$ is hydrogen or $C_{1-4}$ alkyl;

$R^{3-2}$ is halogen or hydroxyl;

R is hydrogen, hydroxyl, $C_{1-6}$ alkoxy or

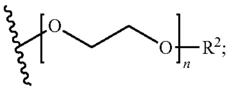

$R^2$ is $C_{1-6}$ alkyl or hydrogen;

n is an integer from 0 to 500; and

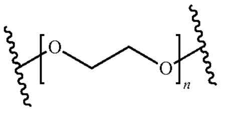

is polyethylene glycol with a linear, tree, star or hyperbranched structure comprising —$(OCH_2CH_2)_n$—.

In some embodiments, when $R^1$ is unsubstituted or $R^{1-1}$ substituted $C_{1-6}$ alkyl, the number of $R^{1-1}$ is one or more, and when more $R^{1-1}$ are provided, the $R^{1-1}$ may be the same or different.

In some embodiments, when $R^1$ is unsubstituted or $R^{1-1}$ substituted $C_{1-6}$ alkyl, the $C_{1-6}$ alkyl is $C_{1-4}$ alkyl.

In some embodiments, when $R^1$ is $C_{6-10}$ aryl, the $C_{6-10}$ aryl is phenyl.

In some embodiments, when $R^1$ is $C_{3-10}$ cycloalkyl, the $C_{3-10}$ cycloalkyl is $C_{3-6}$ cycloalkyl.

In some embodiments, when $R^1$ is $C_{6-12}$ aryl-($C_{1-4}$ alkyl)-, the $C_{6-12}$ aryl-($C_{1-4}$ alkyl)- is benzyl.

In some embodiments, when $R^1$ is $C_{3-10}$ cycloalkyl-($C_{1-4}$ alkyl)-, the $C_{3-10}$ cycloalkyl-($C_{1-4}$ alkyl)- is $C_{3-6}$ cycloalkyl-($C_{1-2}$ alkyl).

In some embodiments, when $R^{1-1}$ is halogen, the halogen is fluorine, chlorine, bromine or iodine.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{1-6}$ alkyl, the number of $R^{3-1}$ is one or more, and when more $R^{3-1}$ are provided, the $R^{3-1}$ may be the same or different.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{1-6}$ alkyl, the $C_{1-6}$ alkyl is $C_{1-4}$ alkyl.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-2}$ substituted $C_{6-12}$ aryl-($C_{1-4}$ alkyl)-, the number of $R^{3-2}$ is one or more, and when more $R^{3-2}$ are provided, the $R^{3-2}$ may be the same or different.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{6-12}$ aryl-($C_{1-4}$ alkyl)-, the $C_{6-12}$ aryl-($C_{1-4}$ alkyl)- is $C_{6-12}$ aryl-($C_{1-2}$ alkyl)-.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from 5-10 membered heteroaryl-($C_{1-4}$ alkyl)-"containing 1 to 3 heteroatoms selected from one or more of N, O and S", the 5-10 membered heteroaryl-($C_{1-4}$ alkyl)- is 5-9 membered heteroaryl-($CH_2$)—.

In some embodiments, when $R^{3-1-1}$ is $C_{1-4}$ alkyl, the $C_{1-4}$ alkyl is methyl, ethyl, n-propyl or isopropyl.

In some embodiments, m is an integer from 1 to 4.

In some embodiments, n is an integer from 0 to 400.

In some embodiments,

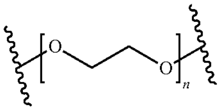

is polyethylene glycol with a linear structure comprising —$(OCH_2CH_2)_n$—.

In some embodiments, when $R^2$ is $C_{1-6}$ alkyl, the $C_{1-6}$ alkyl is $C_{1-4}$ alkyl.

In some embodiments, when R is $C_{1-6}$ alkoxy, the $C_{1-6}$ alkoxy is $C_{1-4}$ alkoxy.

In some embodiments, when $R^1$ is unsubstituted or $R^{1-1}$ substituted $C_{1-6}$ alkyl, the number of $R^{1-1}$ is 1, 2 or 3.

In some embodiments, when $R^1$ is unsubstituted or $R^{1-1}$ substituted $C_{1-6}$ alkyl, the $C_{1-6}$ alkyl is methyl, ethyl, n-propyl, isopropyl, n-butyl, isobutyl, sec-butyl or tertiary butyl.

In some embodiments, when $R^1$ is $C_{3-10}$ cycloalkyl, the $C_{3-10}$ cycloalkyl is cyclopropyl, cyclobutyl, cyclopentyl or cyclohexyl.

In some embodiments, when $R^1$ is $C_{3-10}$ cycloalkyl-($C_{1-4}$ alkyl)-, the $C_{3-10}$ cycloalkyl-($C_{1-4}$ alkyl)- is cyclopropylmethyl, cyclobutylmethyl, cyclopentylmethyl or cyclohexylmethyl.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{1-6}$ alkyl, the number of $R^{3-1}$ is 1, 2 or 3.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{1-6}$ alkyl, the $C_{1-6}$ alkyl is methyl, ethyl, n-propyl, isopropyl, n-butyl, sec-butyl or tertiary butyl.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-2}$ substituted $C_{6-12}$ aryl-($C_{1-4}$ alkyl)-, the number of $R^{3-2}$ is 1, 2 or 3.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-2}$ substituted $C_{6-12}$ aryl-($C_{1-4}$ alkyl)-, the $C_{6-12}$ aryl-($C_{1-4}$ alkyl)- is benzyl.

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from 5-10 membered heteroaryl-($C_{1-4}$ alkyl)-"containing 1 to 3 heteroatoms selected from one or more of N, O and S", the 5-10 membered heteroaryl-($C_{1-4}$ alkyl)- is indolylmethyl or imidazolylmethyl.

In some embodiments, m is an integer from 1 to 2.

In some embodiments, n is an integer from 0 to 100.

In some embodiments, when $R^2$ is $C_{1-6}$ alkyl, the $C_{1-6}$ alkyl is methyl, ethyl, n-propyl, isopropyl, n-butyl, isobutyl, sec-butyl or tertiary butyl.

In some embodiments, when R is $C_{1-6}$ alkoxy, the $C_{1-6}$ alkoxy is methoxy, ethoxy, n-propoxy, isopropoxy, n-butoxy, sec-butoxy, isobutoxy or tert-butoxy.

In some embodiments, when $R^1$ is $R^{1-1}$ substituted $C_{1-6}$ alkyl, the $R^{1-1}$ substituted $C_{1-6}$ alkyl is trifluoromethyl, or

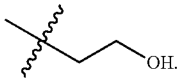 [SMILES: *CCO]

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from $R^{3-1}$ substituted $C_{1-6}$ alkyl, the $R^{3-1}$ substituted $C_{1-6}$ alkyl is

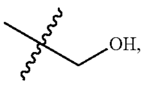 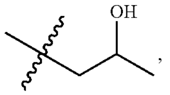, 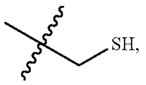

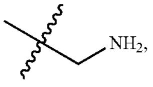 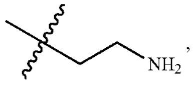,

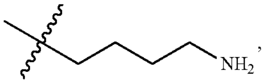, 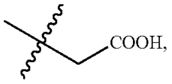

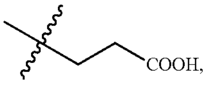 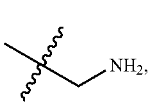

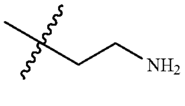 or 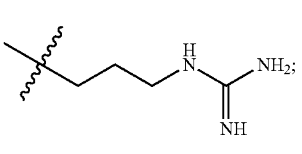

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from $R^{3-2}$ substituted $C_{6-12}$ aryl-($C_{1-4}$ alkyl)-, the $R^{3-2}$ substituted $C_{6-12}$ aryl-($C_{1-4}$ alkyl)- is

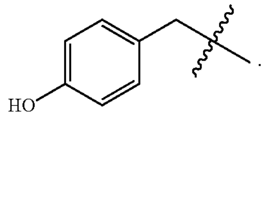 [SMILES: *Cc1ccc(O)cc1]

In some embodiments, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from 5-10 membered heteroaryl-($C_{1-4}$ alkyl)-"containing 1 to 3 heteroatoms selected from one or more of N, O and S", the 5-10 membered heteroaryl-($C_{1-4}$ alkyl)- is

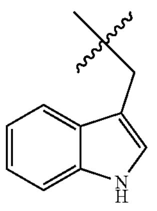 or 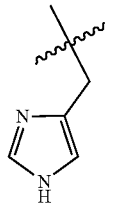.

In some embodiments, $R^1$ is hydrogen, unsubstituted or $R^{1-1}$ substituted $C_{1-6}$ alkyl or $C_{3-10}$ cycloalkyl.

In some embodiments, $R^{1-1}$ is hydroxyl.

In some embodiments, m is an integer from 1 to 2.

In some embodiments, Z is a single bond or

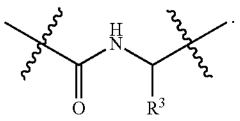

In some embodiments, $R^3$ is hydrogen, unsubstituted or $R^{3-1}$ substituted $C_{1-6}$ alkyl, unsubstituted or $R^{3-2}$ substituted $C_{6-12}$ aryl-($C_{1-4}$ alkyl)-, or heteroaryl-($C_{1-4}$ alkyl)-, and the heteroaryl is 5-10 membered heteroaryl "containing 1 to 3 heteroatoms selected from one or more of N, O and S".

In some embodiments, $R^{3-1}$ is hydroxyl, carboxyl, amino, sulfhydryl, —(C═O)$NR^{3-1-1}$, or —NH(C═NH)$NH_2$.

In some embodiments, $R^{3-1-1}$ is hydrogen.

In some embodiments, $R^{3-2}$ is hydroxyl.

In some embodiments, n is an integer from 0 to 400.

In some embodiments,

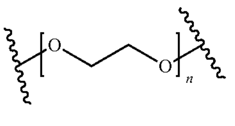

is polyethylene glycol with a linear structure comprising —$(OCH_2CH_2)_n$—.

In some embodiments, X is O or —$NR^1$;

$R^1$ is hydrogen, unsubstituted or $R^{1-1}$ substituted $C_{1-6}$ alkyl or $C_{3-10}$ cycloalkyl;

$R^{1-1}$ is hydroxyl;

Y is —$(CH_2)_m$—;

m is an integer from 1 to 2;

Z is a single bond or

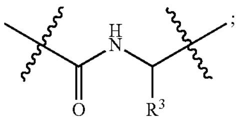

$R^3$ is hydrogen, unsubstituted or $R^{3-1}$ substituted $C_{1-6}$ alkyl, unsubstituted or $R^{3-2}$ substituted $C_{6-12}$ aryl-($C_{1-4}$ alkyl)-, or heteroaryl-($C_{1-4}$ alkyl)-, and the heteroaryl is 5-10 membered heteroaryl "containing 1 to 3 heteroatoms selected from one or more of N, O and S";

$R^{3-1}$ is hydroxyl, carboxyl, amino, sulfhydryl, —(C═O)$NR^{3-1-1}$, or —NH(C═NH)$NH_2$;

$R^{3-1-1}$ is hydrogen;

$R^{3-2}$ is hydroxyl;

R is hydrogen, $C_{1-6}$ alkoxy or

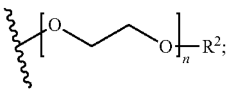

$R^2$ is $C_{1-6}$ alkyl or hydrogen;

n is an integer from 0 to 400; and

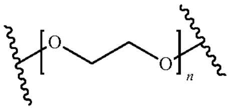

is polyethylene glycol with a linear structure comprising —$(OCH_2CH_2)_n$—.

In some embodiments, X is O or —$NR^1$;

$R^1$ is hydrogen, unsubstituted or $R^{1-1}$ substituted $C_{1-6}$ alkyl or $C_{3-10}$ cycloalkyl;

$R^{1-1}$ is hydroxyl;

Y is —$(CH_2)_m$—;

m is an integer from 1 to 2;

Z is a single bond or

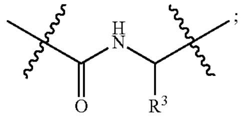

$R^3$ is hydrogen, unsubstituted or $R^{3-1}$ substituted $C_{1-6}$ alkyl, unsubstituted or $R^{3-2}$ substituted $C_{6-12}$ aryl-($C_{1-4}$ alkyl)-, or heteroaryl-($C_{1-4}$ alkyl)-, and the heteroaryl is 5-10 membered heteroaryl "containing 1 to 3 heteroatoms selected from one or more of N, O and S";

$R^{3-1}$ is hydroxyl, carboxyl, amino, sulfhydryl, —(C═O)$NR^{3-1-1}$, or —NH(C═NH)$NH_2$;

$R^{3-1-1}$ is hydrogen;

R is hydrogen, hydroxyl, $C_{1-6}$ alkoxy or

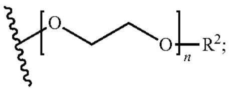

$R^2$ is $C_{1-6}$ alkyl or hydrogen;

n is an integer from 0 to 400; and

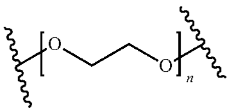

is polyethylene glycol with a linear structure comprising —$(OCH_2CH_2)_n$—.

In some embodiments, X is —$NR^1$;

$R^1$ is hydrogen;

Y is —$(CH_2)_m$—;

m is an integer from 1 to 2;

Z is a single bond or

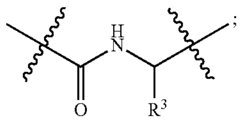

$R^3$ is hydrogen, or unsubstituted or $R^{3-1}$ substituted $C_{1-6}$ alkyl;

$R^{3-1}$ is hydroxyl, carboxyl, amino, sulfhydryl, —(C═O)$NR^{3-1-1}$, or —NH(C═NH)$NH_2$;

$R^{3-1-1}$ is hydrogen;

R is hydrogen, $C_{1-6}$ alkoxy or

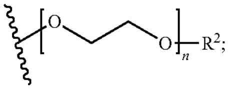

$R^2$ is $C_{1-6}$ alkyl or hydrogen;

n is an integer from 0 to 100; and

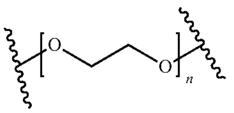

is polyethylene glycol with a linear structure comprising —$(OCH_2CH_2)_n$—.

In some embodiments, X is —$NR^1$;

$R^1$ is hydrogen;

Y is —$(CH_2)_m$—;

m is an integer from 1 to 2;

Z is a single bond or

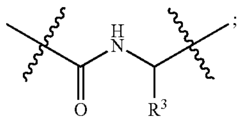

$R^3$ is hydrogen, or unsubstituted or $R^{3-1}$ substituted $C_{1-6}$ alkyl;

$R^{3-1}$ is hydroxyl, carboxyl, amino, sulfhydryl, —(C═O)$NR^{3-1-1}$, or —NH(C═NH)$NH_2$;

$R^{3-1-1}$ is hydrogen;

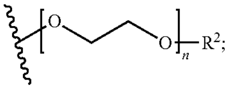

R is hydrogen, hydroxyl, $C_{1-6}$ alkoxy or
$R^2$ is $C_{1-6}$ alkyl or hydrogen;
n is an integer from 0 to 100; and
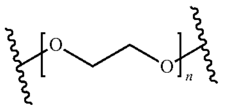
is polyethylene glycol with a linear structure comprising $-(OCH_2CH_2)_n-$.
In some embodiments, the compound represented by formula I is any one of the following compounds:
S1
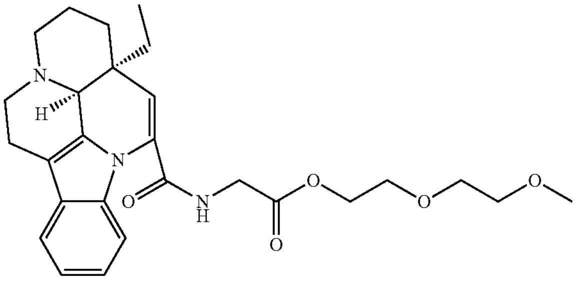
,
S2
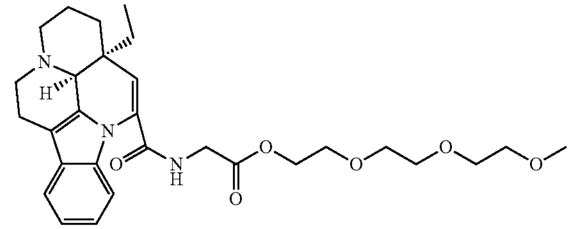
,
S3
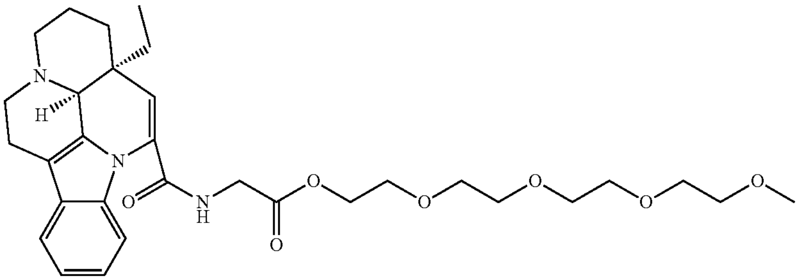
,
S4
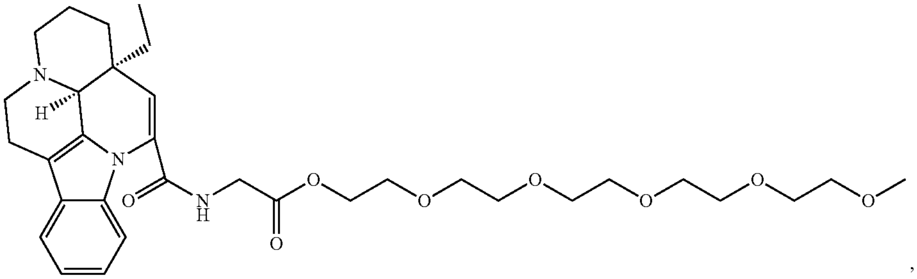
,
S5
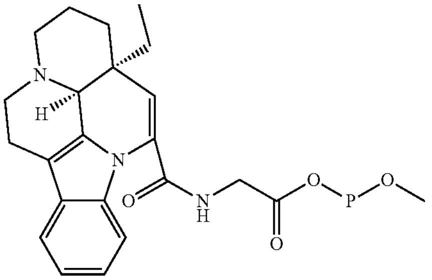
P = PEG-2000 ,
S6
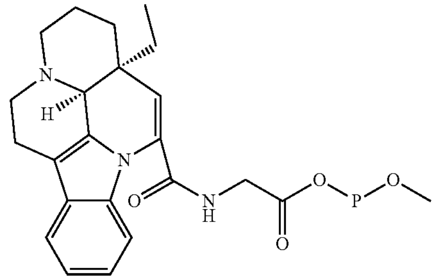
P = PEG-1000 , -continued
S7
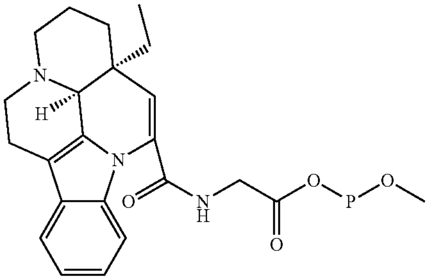
P = PEG-400 ,
S8
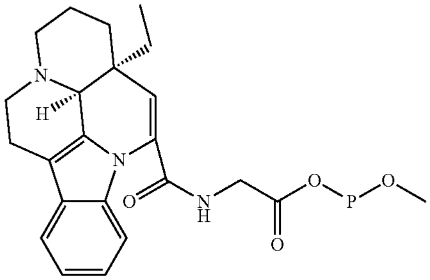
P = PEG-8000 ,
S9
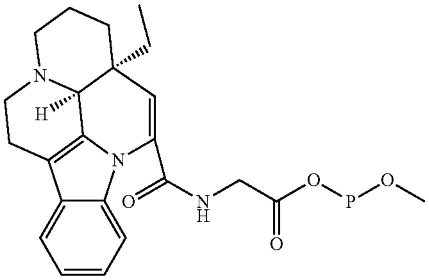
P = PEG-5000 ,
S10
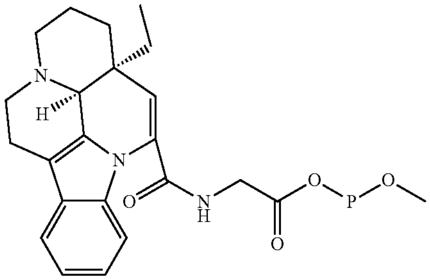
P = PEG-12000 ,
S11
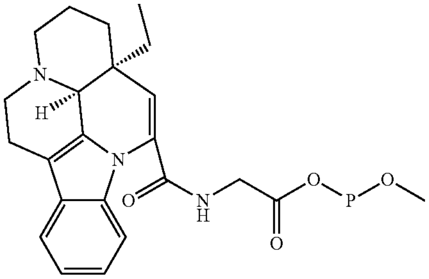
P = PEG-20000 ,
S12
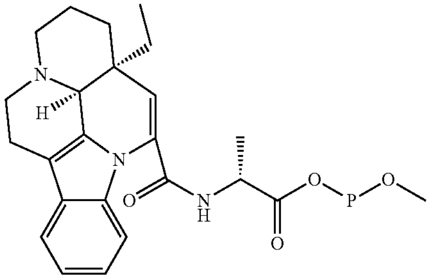
P = PEG-2000 ,
S13
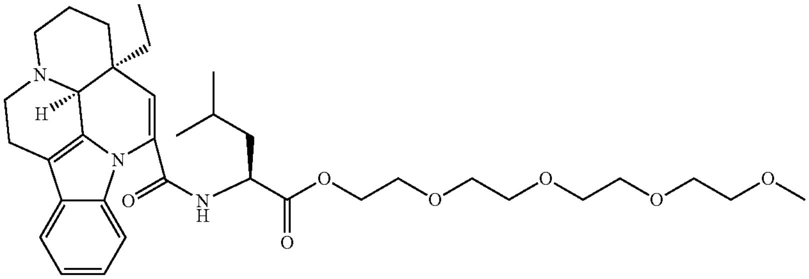
,
S14
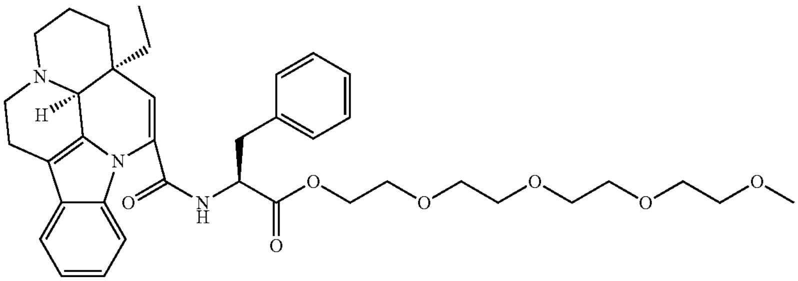
, -continued
S15
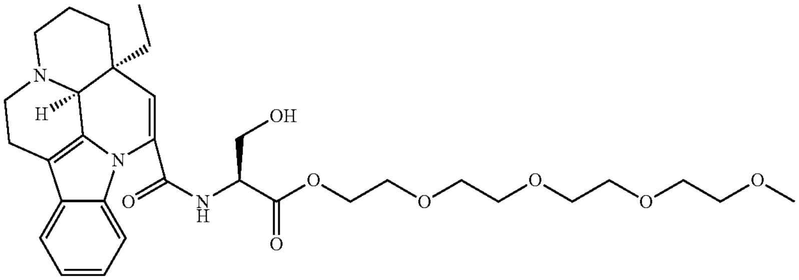
,
S16
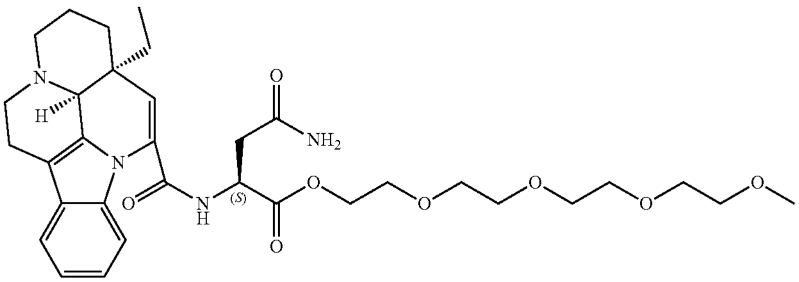
,
S17
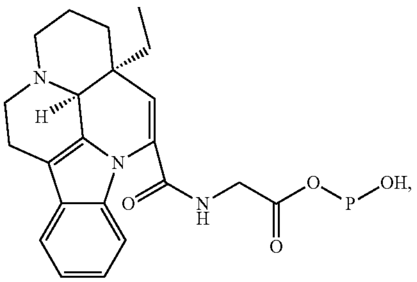
P = PEG-2000
S18
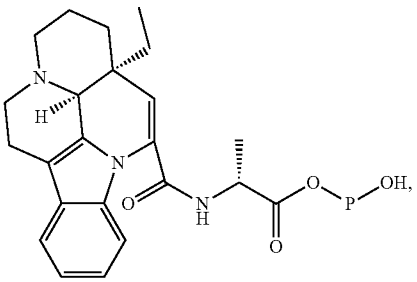
P = PEG-2000
S19
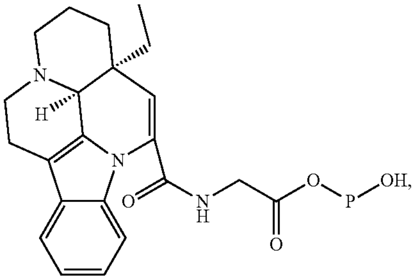
P = PEG-4000
S20
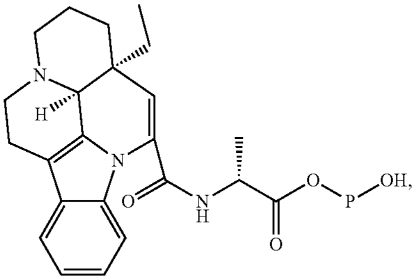
P = PEG-4000
S21
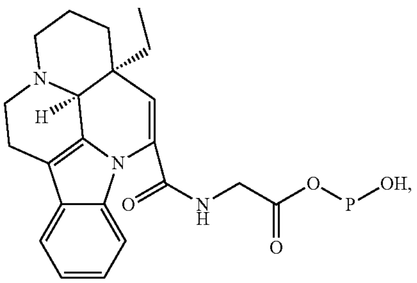
P = PEG-400
S22
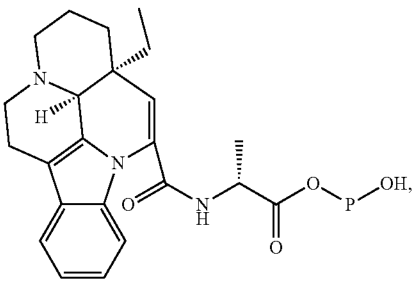
P = PEG-400

-continued
S23
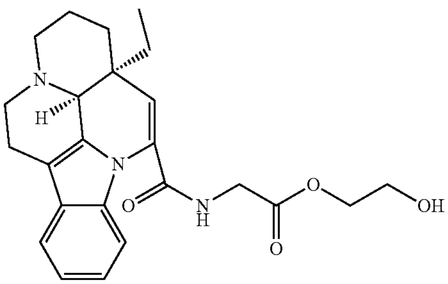
,
S24
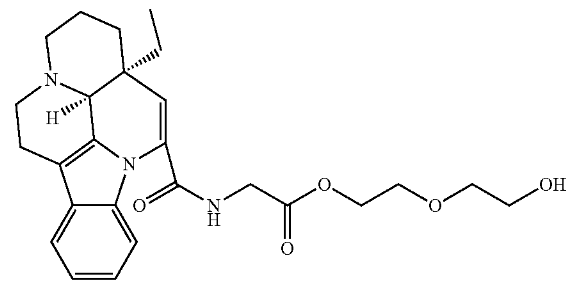
,
S25
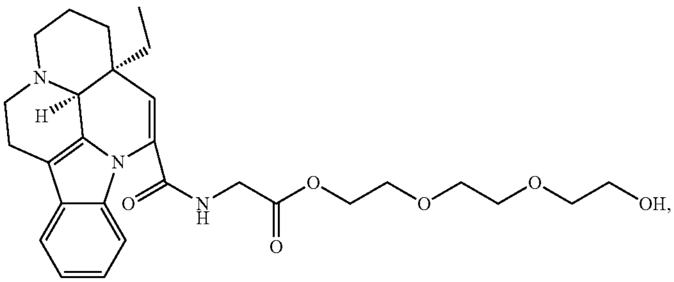
OH,
S26
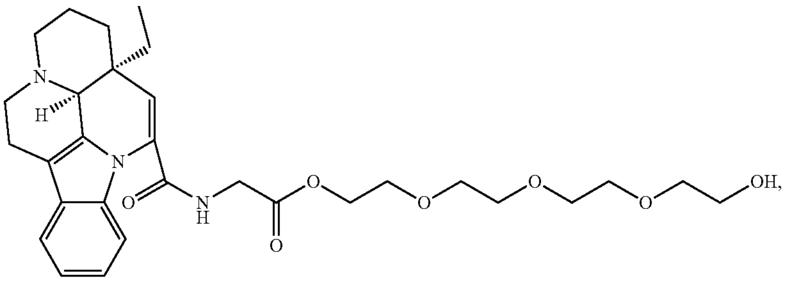
OH,
S27
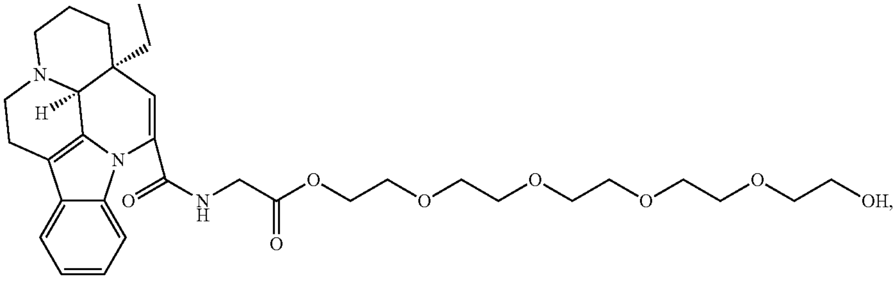
OH,
28
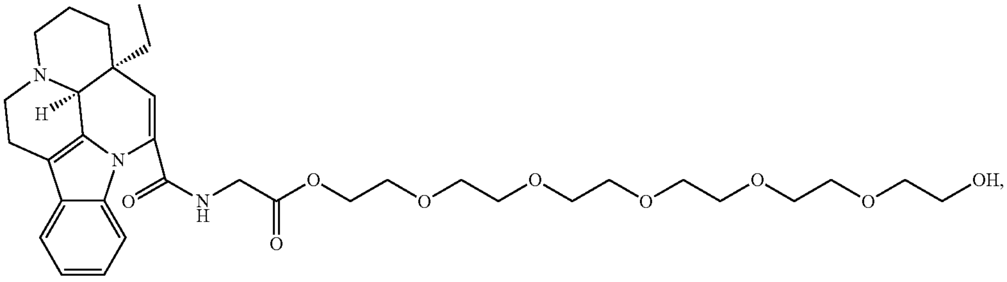
OH, -continued
S29
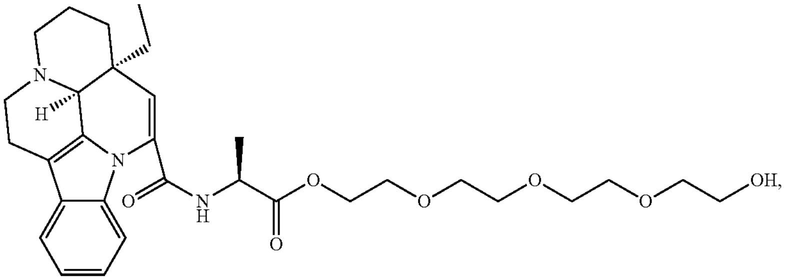
S30
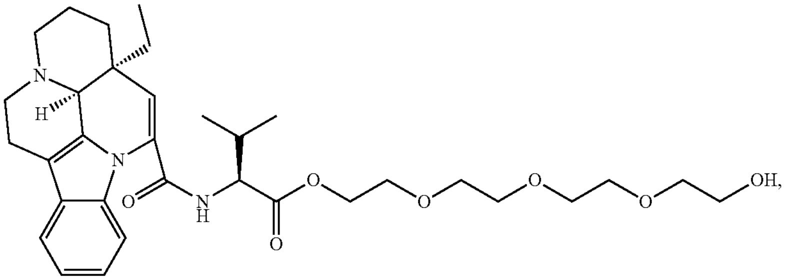
S31
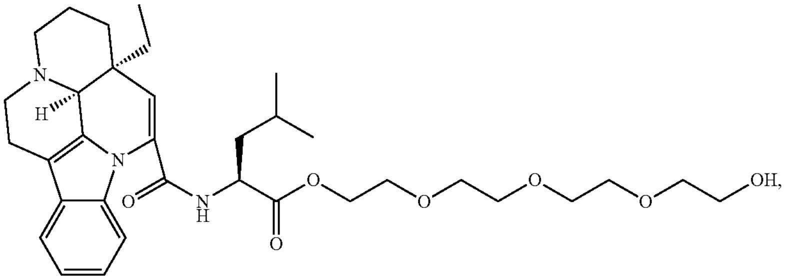
S32
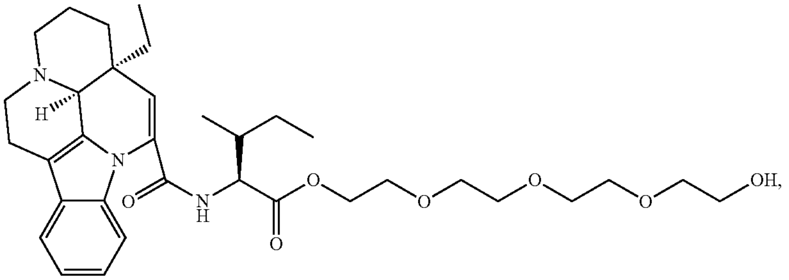
S33
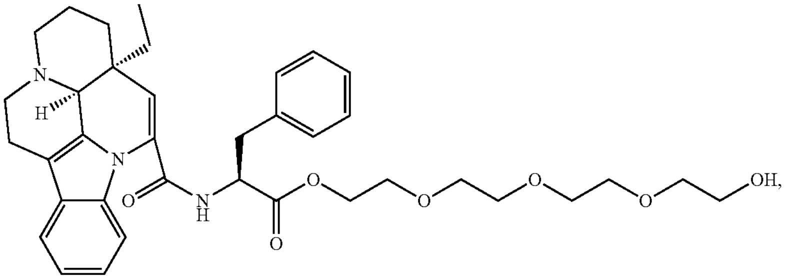

-continued
S34
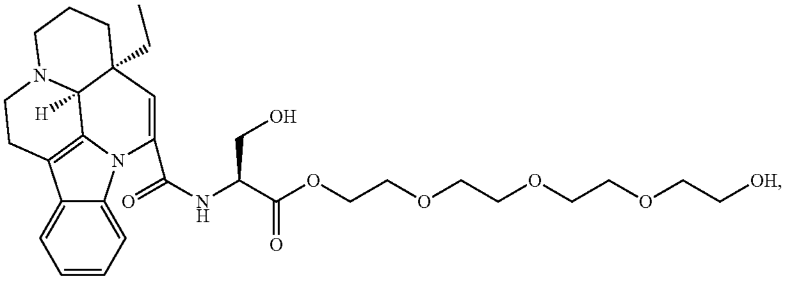
S35
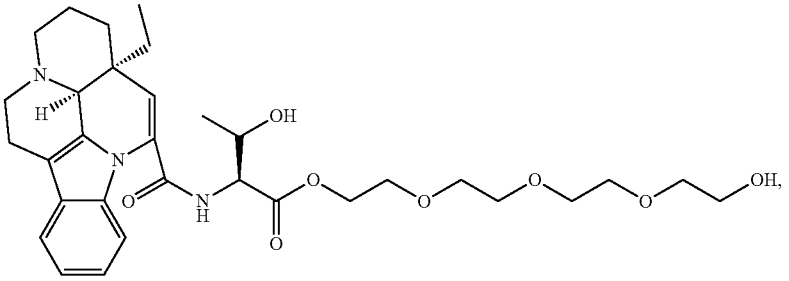
S36
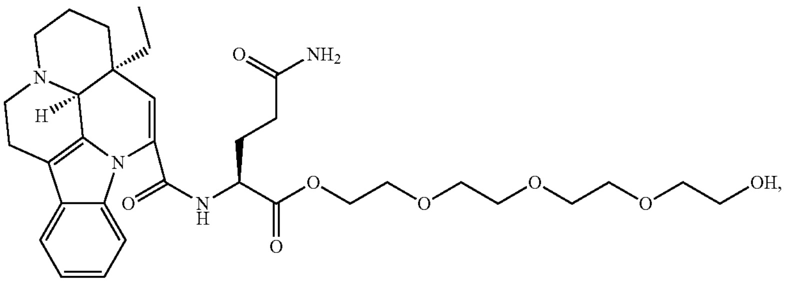
S37
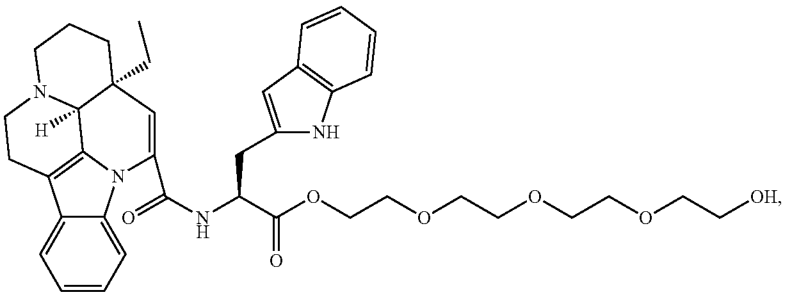
S38
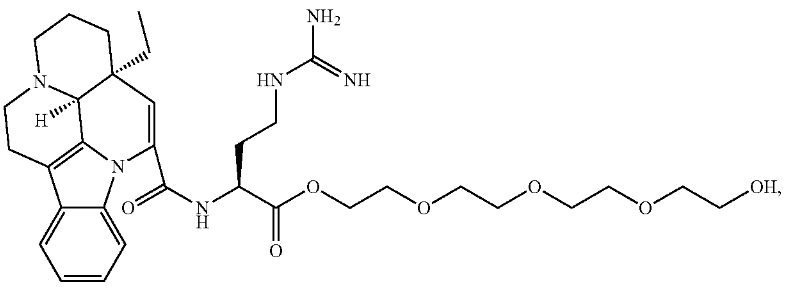

-continued
S39
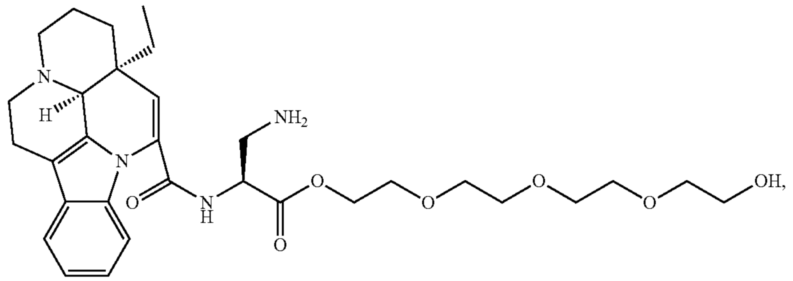
S40
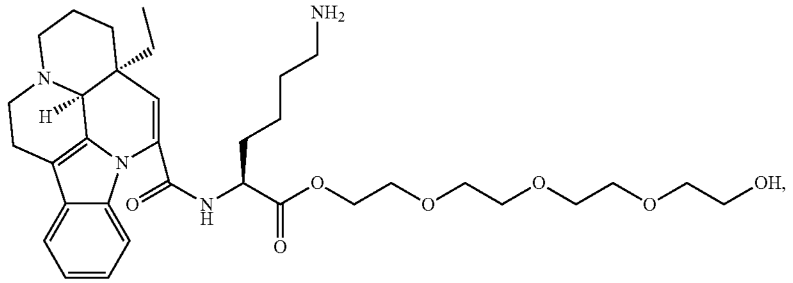
S41
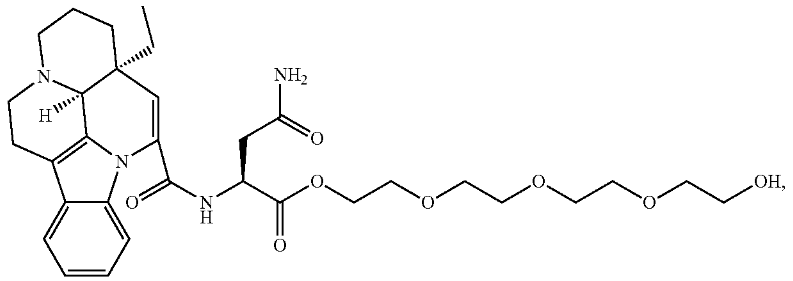
S42
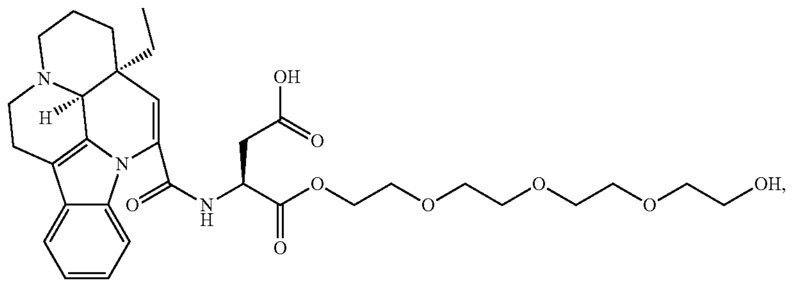
S43
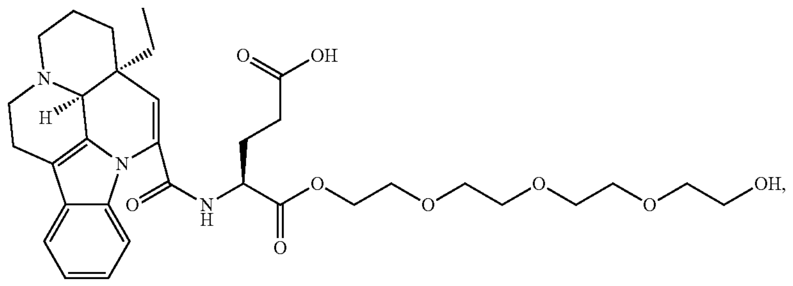

-continued
S44
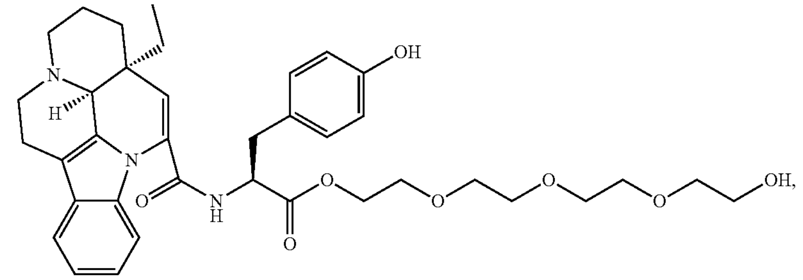
S45
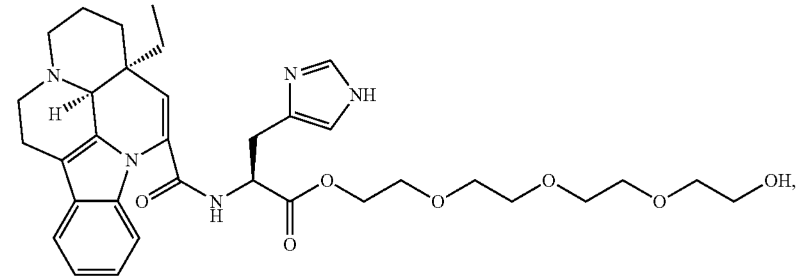
S46
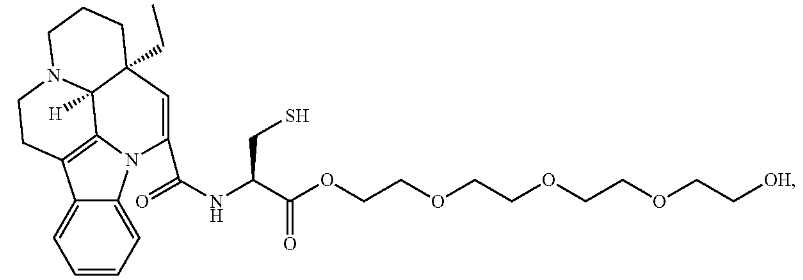
S47
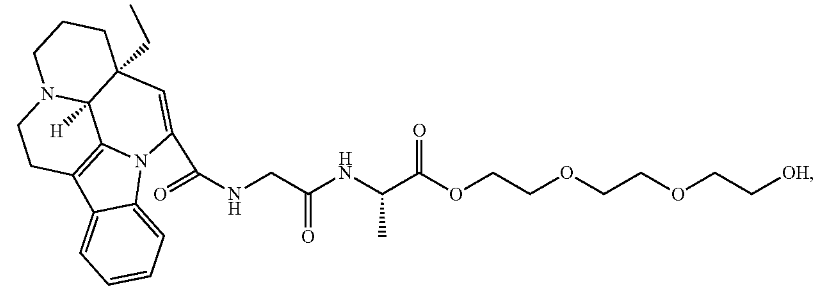
S48
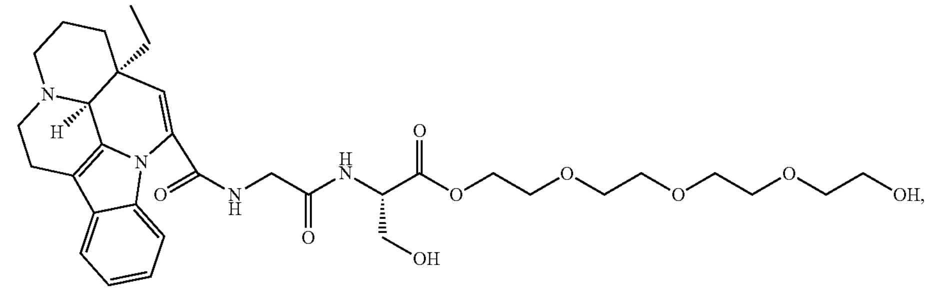

-continued
S49
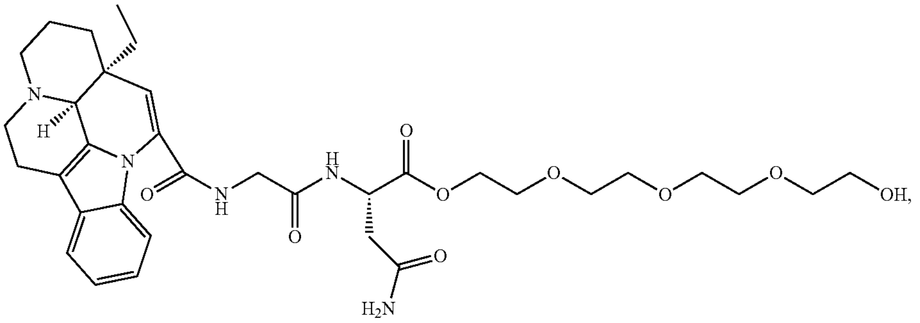
S50
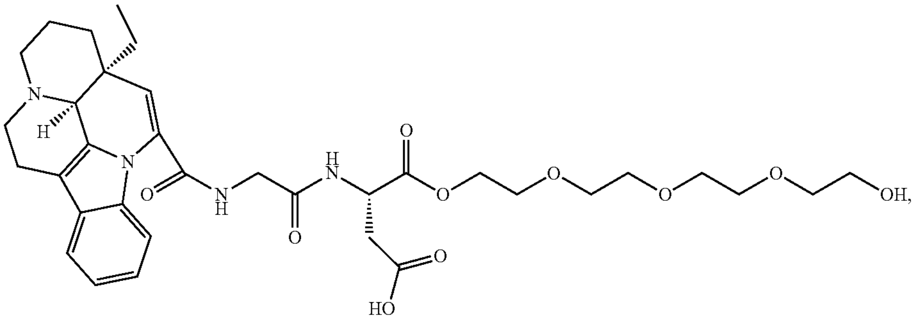
S51
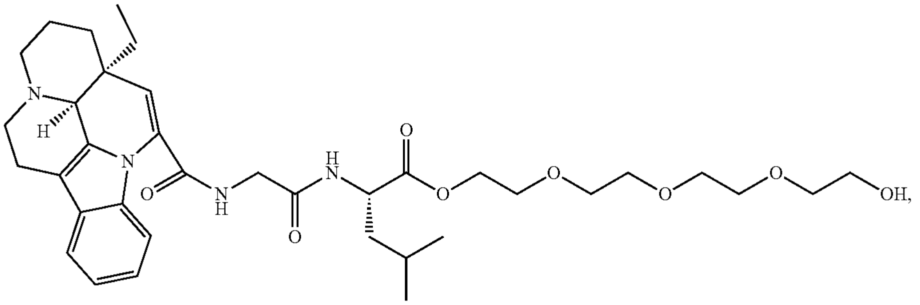
S52
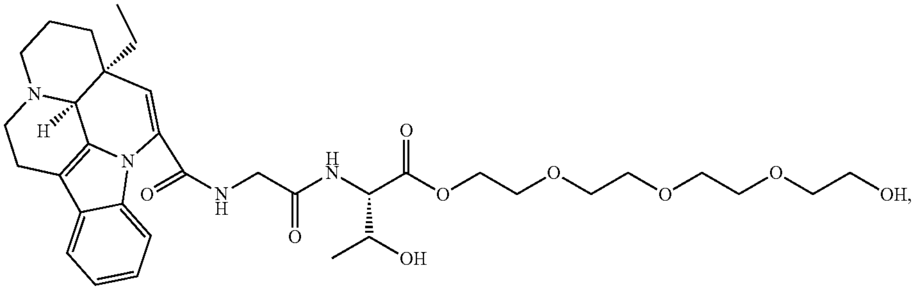
S53
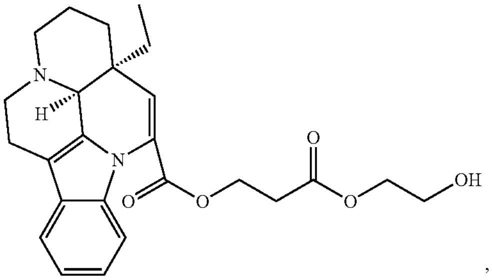
,
S54
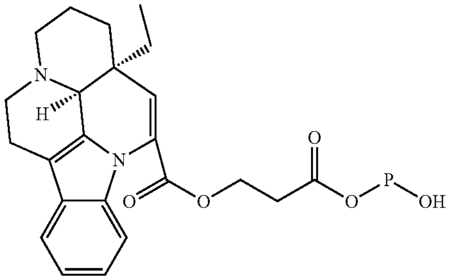
,
P = PEG-4000

-continued
S55
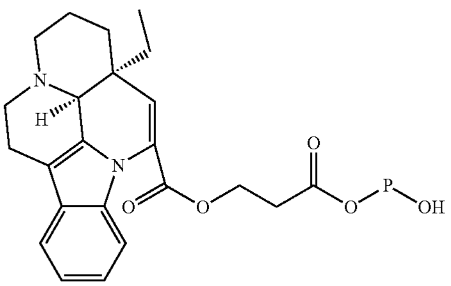
P = PEG-2000
,
S56
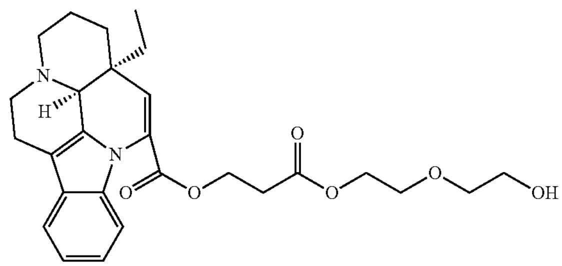
,
S57
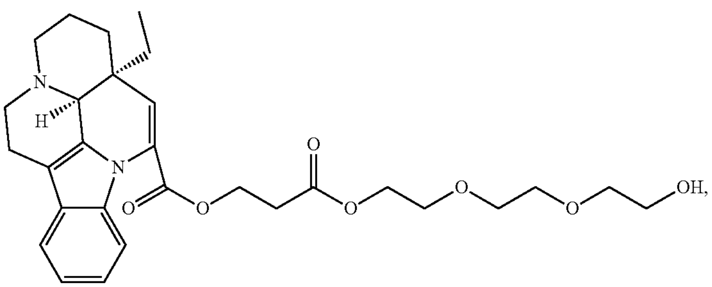
S58
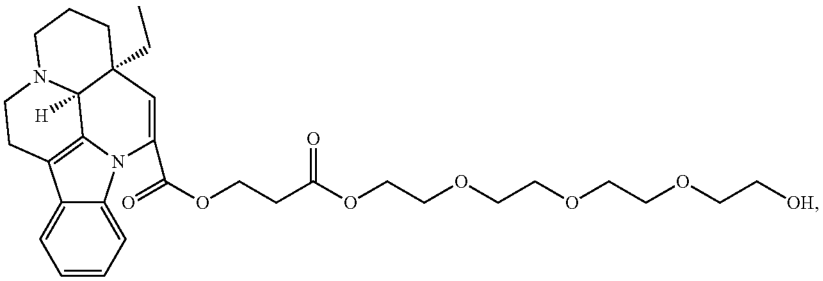
S59
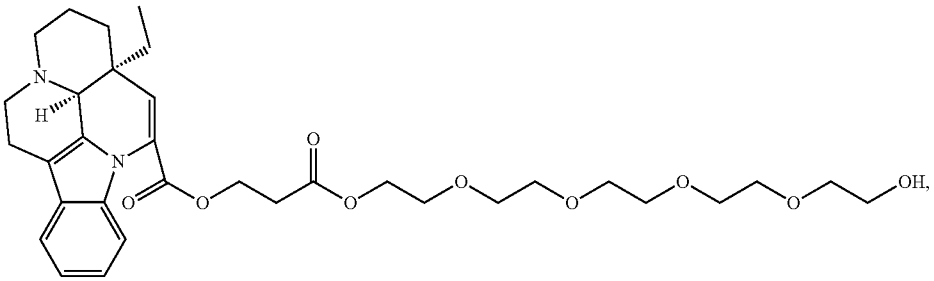
S60
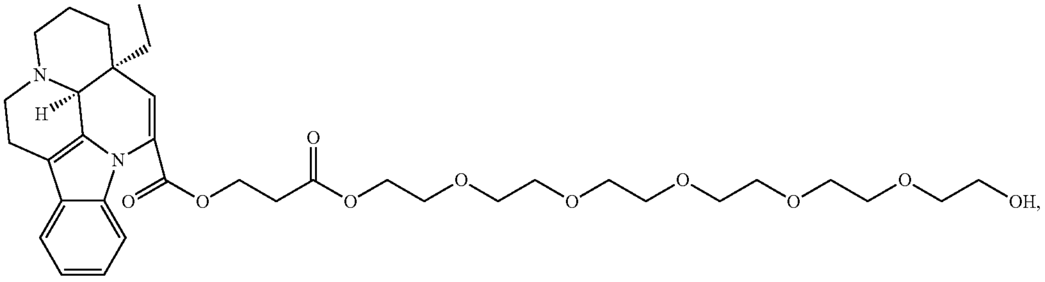

-continued
S61
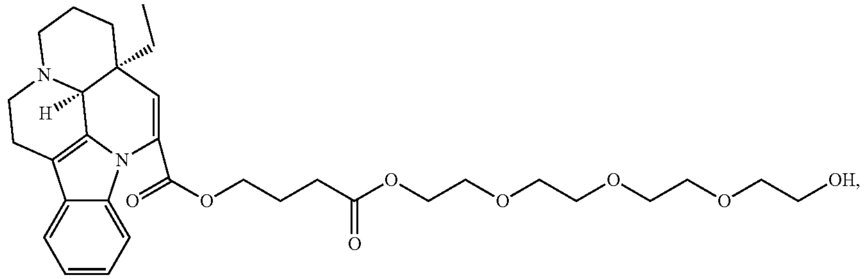
S62
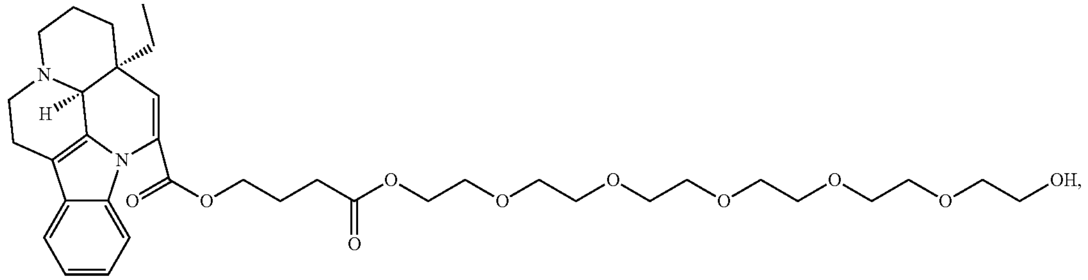
S63
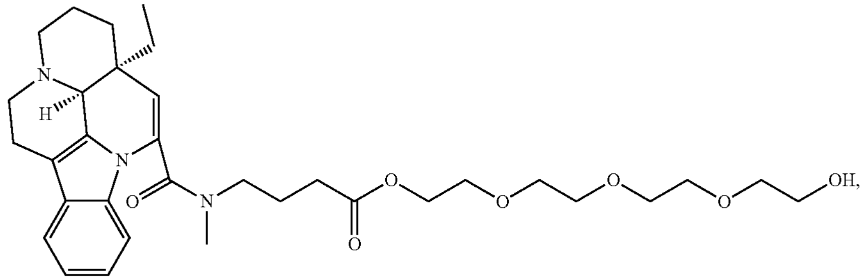
S64
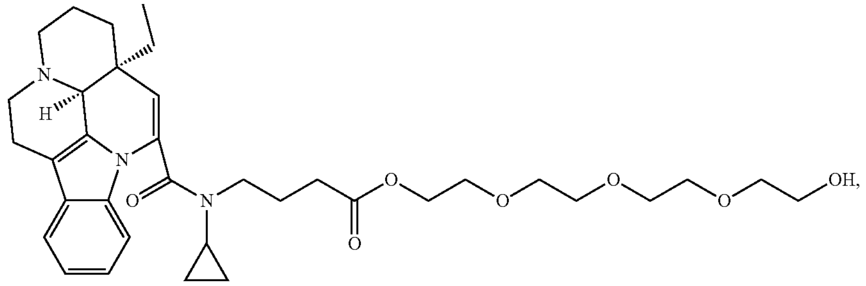
S65
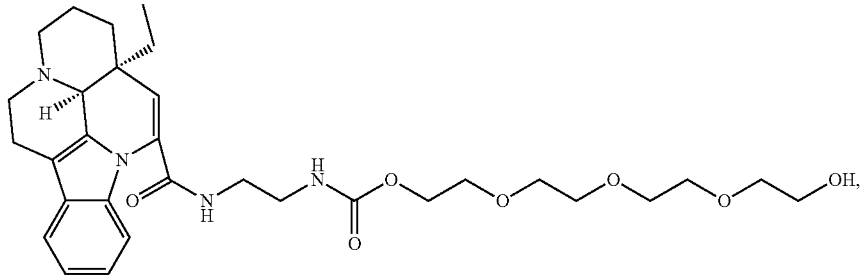

-continued
S66
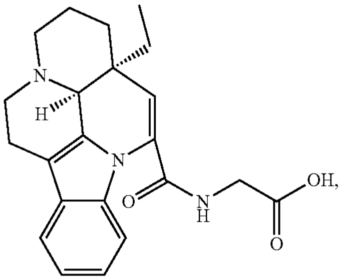
S67
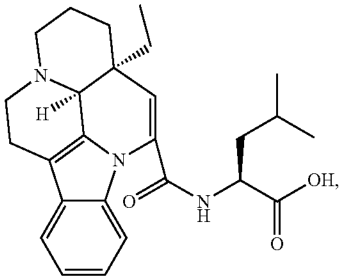
S68
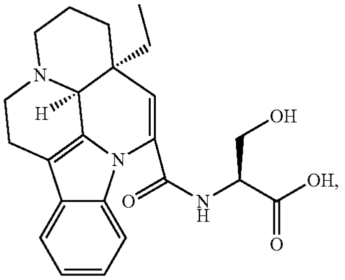
S69
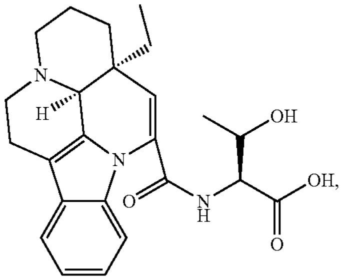
S70
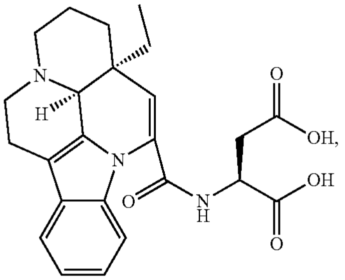
S71
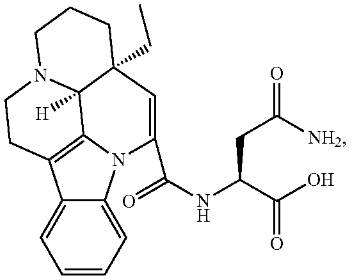
S72
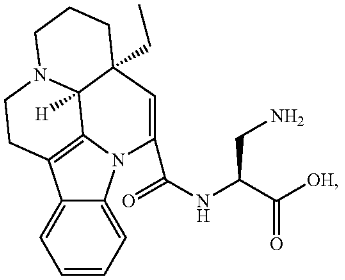
S73
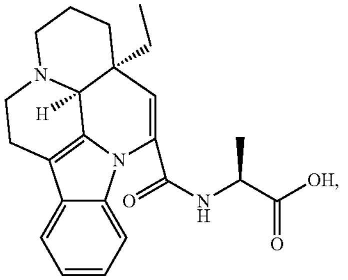
S74
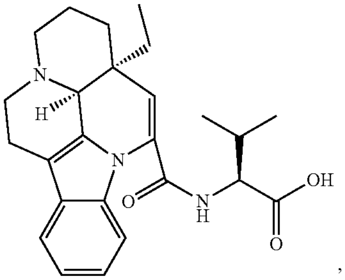
,
S75
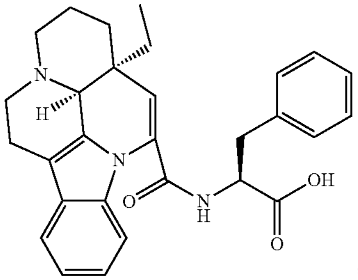
, -continued
S76
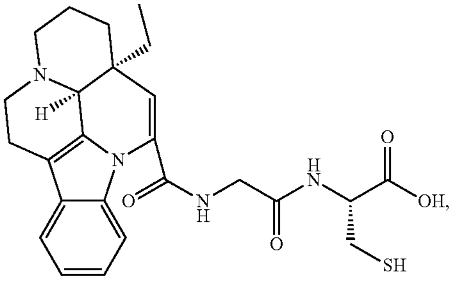
S77
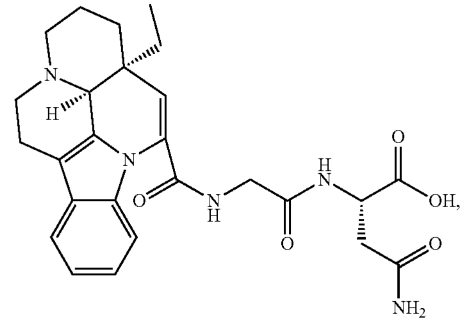
S78
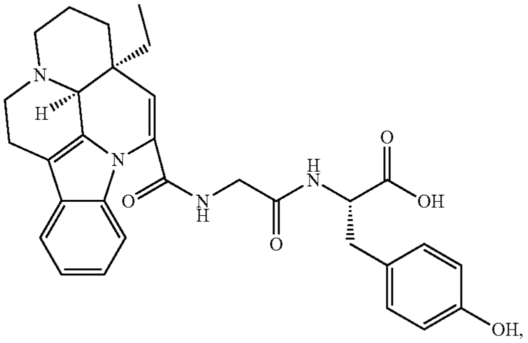
S79
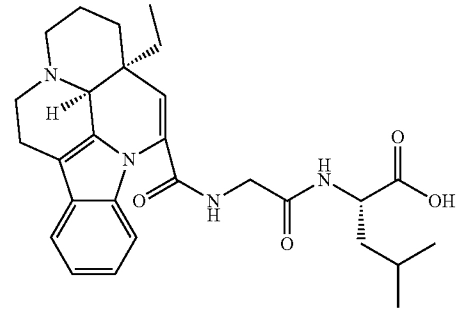
,
S80
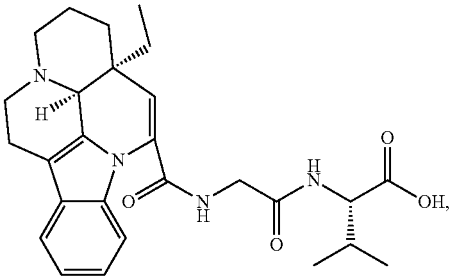
S81
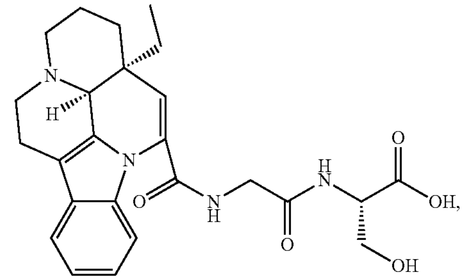
S82
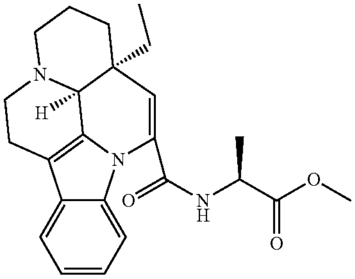
,
S83
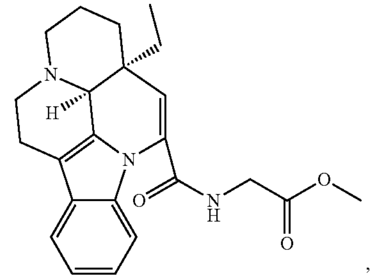
,
S84
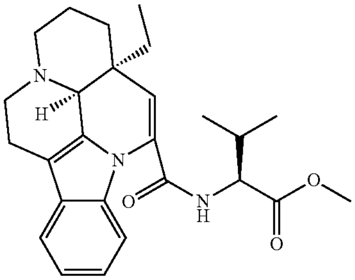
,
S85
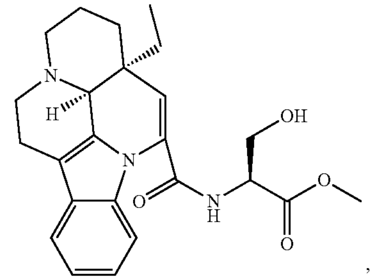
, -continued

S86

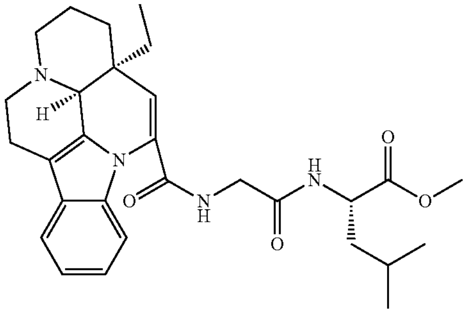

and

S87

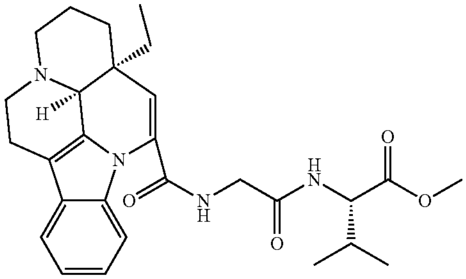

.

The present invention also provides a preparation method of the compound represented by formula I, wherein the synthesis comprises the following step of: in a solvent, under the action of a base and a condensing agent, subjecting a compound as shown in formula II and a compound as shown in formula III to a condensation reaction as shown below;

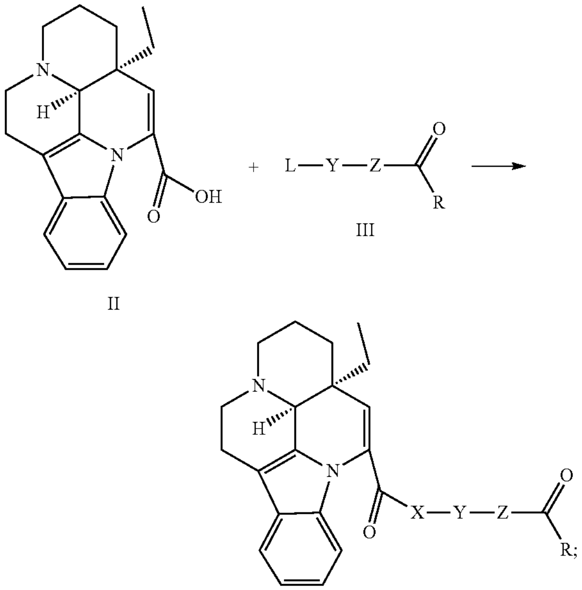

II III I wherein, L is —$NHR_1$, hydroxyl,

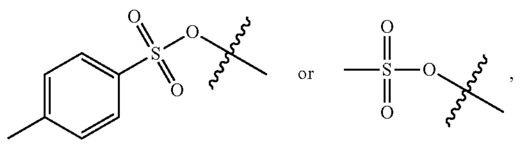

or , and $R^1$, X, Y, Z and R are defined as above.

The present invention also provides a preparation method of the compound represented by formula I, wherein the synthesis comprises the following step of: in a solvent, under the action of a base and a condensing agent, subjecting a compound as shown in formula II and a compound as shown in formula III to a condensation reaction as shown below;

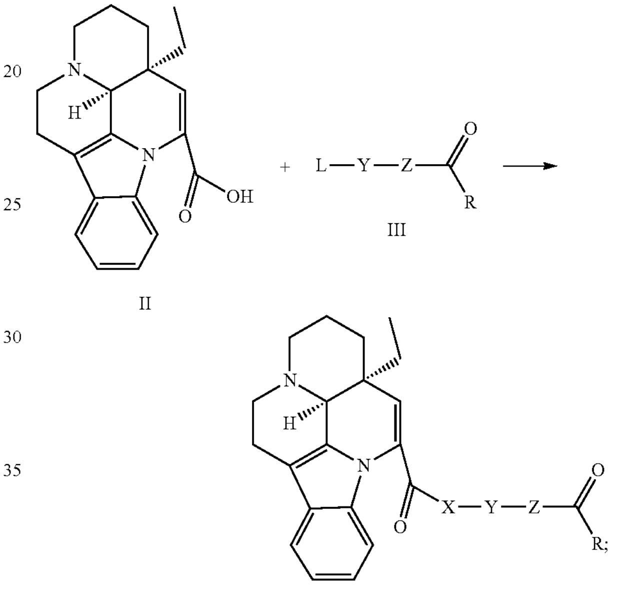

II III I wherein, L is —$NHR_1$, hydroxyl,

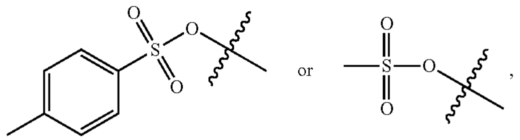

or , and $R^1$, X, Y, Z and R are defined as above.

In some embodiments, the solvent is an amide solvent or a halogenated alkane solvent.

In some embodiments, the base is an organic base or an inorganic base.

In some embodiments, the condensing agent is a carbodiimide, an organophosphorus salt or an onium salt.

In some embodiments, when the solvent is an amide solvent, the amide is N,N-dimethylformamide, N,N-dimethylacetamide or N-methylpyrrolidone.

In some embodiments, when the solvent is a halogenated alkane solvent, the halogenated alkane is dichloromethane.

In some embodiments, when the base is an organic base, the organic base is triethylamine, DIPEA or DMAP.

In some embodiments, when the base is an inorganic base, the inorganic base is potassium carbonate or caesium carbonate.

In some embodiments, when the condensing agent is a carbodiimide, the carbodiimide is DCC, DIC or EDCI.

In some embodiments, when the condensing agent is an organophosphorus salt, the organophosphorus salt is BOP or PyBOP.

In some embodiments, when the condensing agent is an onium salt, the onium salt is HATU, HBTU or TBTU.

The present invention further provides use of the compound represented by formula I, or the pharmaceutically acceptable salt thereof, the metabolic precursor thereof, the metabolite thereof, the isomer thereof or the prodrug thereof in preparing a drug for preventing and/or treating diabetic complications and pulmonary fibrosis.

The present invention further provides a pharmaceutical composition, which comprises the compound represented by formula I, or the pharmaceutically acceptable salt thereof, the metabolic precursor thereof, the metabolite thereof, the isomer thereof or the prodrug thereof, and a pharmaceutical excipient.

In the pharmaceutical composition, a dosage of the compound represented by formula I, or the pharmaceutically acceptable salt thereof, the metabolic precursor thereof, the metabolite thereof, the isomer thereof or the prodrug thereof may be a therapeutically effective amount.

The present invention further provides use of the pharmaceutical composition above in preparing a drug for preventing and/or treating diabetic complications and pulmonary fibrosis.

The pharmaceutical excipient may be those excipients widely used in the field of pharmaceutical production. The excipients are mainly used for providing a safe, stable and functional pharmaceutical composition, and may also provide a method, so that active ingredients are dissolved at a desired rate after a subject is administered, or the active ingredients are effectively absorbed after the subject receives the composition. The pharmaceutical excipient may be an inert filler, or provide a certain function, such as stabilizing the overall pH of the composition or preventing degradation of the active ingredients of the composition. The pharmaceutical excipient may comprise one or more of the following excipients: a binder, a suspending agent, an emulsifier, a diluent, a filler, a granulating agent, an adhesive, a disintegrant, a lubricant, an anti-sticking agent, a glidant, a wetting agent, a gelling agent, an absorption retarder, a dissolution inhibitor, a reinforcing agent, an adsorbent, a buffering agent, a chelating agent, a preservative, a colorant, a flavoring agent, and a sweetener.

The pharmaceutical composition of the present invention may be prepared according to the disclosed content using any method known to those skilled in the art, for example, conventional mixing, dissolution, granulation, emulsification, milling, encapsulation, embedding, or lyophilization processes.

The pharmaceutical composition of the present invention may be administered in any form, comprising injection (intravenous), mucosal, oral (solid and liquid formulations), inhalation, ocular, rectal, topical or parenteral (infusion, injection, implantation, subcutaneous, intravenous, intraarterial, intramuscular) administration. The pharmaceutical composition of the present invention may also be a controlled release or delayed release dosage form (for example, liposome or microsphere). Examples of solid oral formulations comprise, but are not limited to, powders, caplets, capsules, soft capsules, and tablets. Examples of liquid formulations for oral or mucosal administration comprise, but are not limited to, suspensions, emulsions, elixirs, and solutions. Examples of topical formulations comprise, but are not limited to, emulsions, gels, ointments, creams, patches, pastes, foams, lotions, drops or serum formulations. Examples of formulations for parenteral administration comprise, but are not limited to, injection solutions, dry powder formulations that may be dissolved or suspended in a pharmaceutically acceptable carrier, suspensions for injection, and emulsions for injection. Examples of other suitable formulations of the pharmaceutical composition comprise, but are not limited to, eye drops and other ophthalmic formulations; aerosols such as nasal sprays or inhalants; liquid dosage forms suitable for parenteral administration; and suppositories and lozenges.

The term “pharmaceutically acceptable salt” refers to a salt of the compound of the present invention, which is prepared from a compound having a specific substituent found in the present invention and a relatively nontoxic acid or base. When the compound of the present invention contains relatively acidic functional groups, a base addition salt can be obtained by contacting a free form of this compound with a sufficient amount of base in a pure solution or a suitable inert solvent. Pharmaceutically acceptable base addition salts comprise sodium, potassium, calcium, ammonium, organic ammonia, or magnesium salts or similar salts. When the compound of the present invention contains relatively basic functional group groups, an acid addition salt can be obtained by contacting a free form of this compound with a sufficient amount of acid in a pure solution or a suitable inert solvent. Examples of the pharmaceutically acceptable acid addition salts comprise inorganic acid salts, and the inorganic acid salts comprise, for example, hydrochloric acid, hydrobromic acid, nitric acid, carbonic acid (forming carbonate or bicarbonate), phosphoric acid (forming phosphate, monohydrogen phosphate, dihydrogen phosphate, sulfuric acid (forming sulfate or bisulfate), hydroiodic acid, phosphorous acid, and the like; and organic acid salts. The organic acids comprise acids such as acetic acid, propionic acid, isobutyric acid, maleic acid, malonic acid, benzoic acid, succinic acid, octanedioic acid, fumaric acid, lactic acid, mandelic acid, phthalic acid, benzenesulfonic acid, p-toluenesulfonic acid, citric acid, tartaric acid, and methanesulfonic acid. The organic acid salts further comprise a salt of an amino acid (such as, arginine, etc.), and a salt of an organic acid such as glucuronic acid. Certain specific compounds of the present invention contain basic and acidic functional groups, and thus can be converted to any base or acid addition salt. Preferably, the salt is contacted with a base or acid in a conventional manner, and the parent compound is then separated, whereby the free form of the compound is regenerated. The free form of the compound differs from the form of various salts thereof in certain physical properties, such as different solubility in polar solvents.

The “pharmaceutically acceptable salt” of the present invention may be synthesized by conventional chemical methods from parent compounds containing acid radicals or bases. In general, such salts are prepared by reacting these compounds in free acid or base form with a stoichiometric suitable base or acid in a mixture of water or an organic solvent or both. Generally, non-aqueous media such as ethers, ethyl acetate, ethanol, isopropanol, or acetonitrile are preferred.

The term “isomer” refers to a compound having the same chemical formula but having different atom arrangements.

The term “metabolite” refers to a pharmaceutically active product produced by metabolism of the compound represented by formula I or a salt thereof in vivo. Such product may be produced from, for example, oxidation, reduction, hydrolysis, amidation, deamidation, esterification, deesterification, glucuronic acidification, enzymatic cleavage, etc. of the administered compound. Therefore, the present invention comprises the metabolite of the compound of the present invention, and also comprises a compound that is produced by a method of bringing the compound of the present invention into contact with a mammal for a period of time sufficient to obtain the metabolite thereof.

The metabolite is typically identified by preparing radiolabeled isotopes of the compound of the present invention. The radiolabeled isotopes of the compound of the present invention are parenterally administered to animals, such as rats, mice, guinea pigs, monkeys, or humans at a detectable dose (e.g., more than about 0.5 mg/kg), which is given sufficient time for metabolism (typically about 30 seconds to 30 hours), and the transformation products thereof can be isolated from urine, blood or other biological samples. These products are easy to isolate because they are labeled (others are isolated by using antibodies that can bind to antigenic epitopes present in metabolites). The metabolite structure is determined in a conventional manner, for example, by MS, LC/MS or NMR analysis. Generally, the analysis of the metabolite is carried out in the same way as conventional drug metabolism research known to those skilled in the art. As long as the metabolite products are not otherwise undetectable in vivo, the metabolite products can be used in the assay of therapeutic dosage administration of the compound of the present invention. The compound of the present invention may contain an unnatural proportion of atomic isotopes on one or more atoms constituting the compound. For example, the compound may be labeled with radioisotopes, such as tritium ($^{3}H$), iodine-125 ($^{125}I$) or C-14 ($^{14}C$). Transformations of all isotopic compositions of the compound of the present invention, whether radioactive or not, are comprised in the scope of the present invention.

In addition to the salt form, the compound provided by the invention also exists in prodrug form. The prodrug of the compound described herein can easily undergo chemical changes under physiological conditions, thus being converted into the compound of the present invention. Any compound that can be transformed in vivo to a bioactive substance (i.e., the compound represented by formula I) is a prodrug within the scope and spirit of the present invention. For example, a compound containing a carboxyl may form a physiologically hydrolyzable ester, which acts as a prodrug by hydrolyzing in vivo to obtain the compound represented by formula I itself. The prodrug is preferably administered orally, because hydrolysis occurs mainly under the influence of digestive enzymes in many cases. Parenteral administration may be used when the ester itself is active or hydrolysis occurs in the blood.

It may be understood by those skilled in the art that according to the convention used in this field, the “” used in the structural formula of the group described in the present application means that the corresponding group is connected with other fragments and groups in the compound represented by formula I at this site.

The “substitution” in the present invention may be one or more, and when there are multiple “substitutions”, the “substitutions” may be the same or different.

The term “multiple” refers to 2, 3, 4 or 5.

The term “halogen” refers to fluorine, chlorine, bromine or iodine.

The term “alkyl” refers to a straight-chain or branched alkyl with a specified number of carbon atoms. Examples of alkyl comprise methyl, ethyl, n-propyl, isopropyl, n-butyl, tert-butyl, isobutyl, sec-butyl, n-pentyl, n-hexyl, n-heptyl, n-octyl and similar alkyl.

The term “cycloalkyl” refers to saturated monocyclic or polycyclic alkyl. The monocyclic cycloalkyl is preferably a monovalent saturated cyclic alkyl with 3-7 ring carbon atoms, more preferably 3-6 carbon atoms, such as cyclopropyl, cyclobutyl, cyclopentyl or cyclohexyl. Each ring of the polycyclic cycloalkyl is saturated and may be a bicyclic or tricyclic cycloalkyl with 4-10 carbon atoms.

The term “heterocycloalkyl” refers to a saturated monocyclic or polycyclic group with heteroatoms. The monocyclic ring preferably contains one, two or three 3-7 membered saturated monocyclic heterocycloalkyl independently selected from N, O and S, and examples thereof comprise, but are not limited to, pyrrolidinyl, tetrahydropyranyl, tetrahydropyranyl, tetrahydrothienyl, tetrahydropyridinyl, tetrahydropyrrolyl, azetidinyl, thiazolidinyl, oxazolidinyl, piperidinyl, morpholinyl, thiomorpholinyl, piperazinyl, azepanyl, diazepanyl, oxazepanyl, dioxolanyl, dioxanyl, and the like. The polycyclic ring is preferably an 8-10 membered saturated polycyclic heterocycloalkyl ring containing 1,2 or 3 rings independently selected from N, O and S, and may be bicyclic or tricyclic, examples of which comprise, but are not limited to octahydropyrrolo[1,2-a]pyrazinyl, (1R,5S)-3,8-diazabicyclo[3.2.1]octyl.

The term “aryl” refers to an aromatic group with a specified number of carbon atoms, preferably a monocyclic, bicyclic or tricyclic aromatic group. When the aryl is bicyclic or tricyclic, each ring satisfies the Huckel Rule. The $C_{6-10}$ aryl in the present invention refers to an aromatic group containing 6 to 10 carbon atoms, such as phenyl or naphthyl.

The term “heteroaryl” refers to an aromatic group containing heteroatoms, preferably containing one, two or three aromatic 5-6 membered monocyclic rings or 9-10 membered bicyclic rings independently selected from nitrogen, oxygen and sulfur. The 5-6 membered monocyclic ring comprises, but is not limited to, pyrrolyl, furyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazole, 1,2,5-oxadiazole, 1,3,4-oxadiazole, thiadiazolyl, dithiazolyl, tetrazolyl, pyridyl, pyranyl, thiapyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl, or tetrazinyl. The 9-10 membered bicyclic ring comprises, but is not limited to, benzimidazolyl, indolyl, indazolyl, benzofuranyl, benzothiazolyl, benzisothiazolyl, benzoxazolyl, benzisoxazolyl, quinolyl and isoquinolyl.

On the basis of not violating the common sense in the field, the above-mentioned preferred conditions may be arbitrarily combined to obtain the preferred examples of the present invention.

The reagents and raw materials used in the present invention are all available in the market.

The present invention has the positive progressive effects that:

(1) The indole alkaloid provided by the present invention has enhanced water solubility.

(2) The indole alkaloid provided by the present invention has good therapeutic effects on diabetic complications comprising diabetic peripheral neuropathy and diabetic foot.

(3) The indole alkaloid provided by the present invention has good therapeutic effects on pulmonary fibrosis.

DETAILED DESCRIPTION

Figure 1:
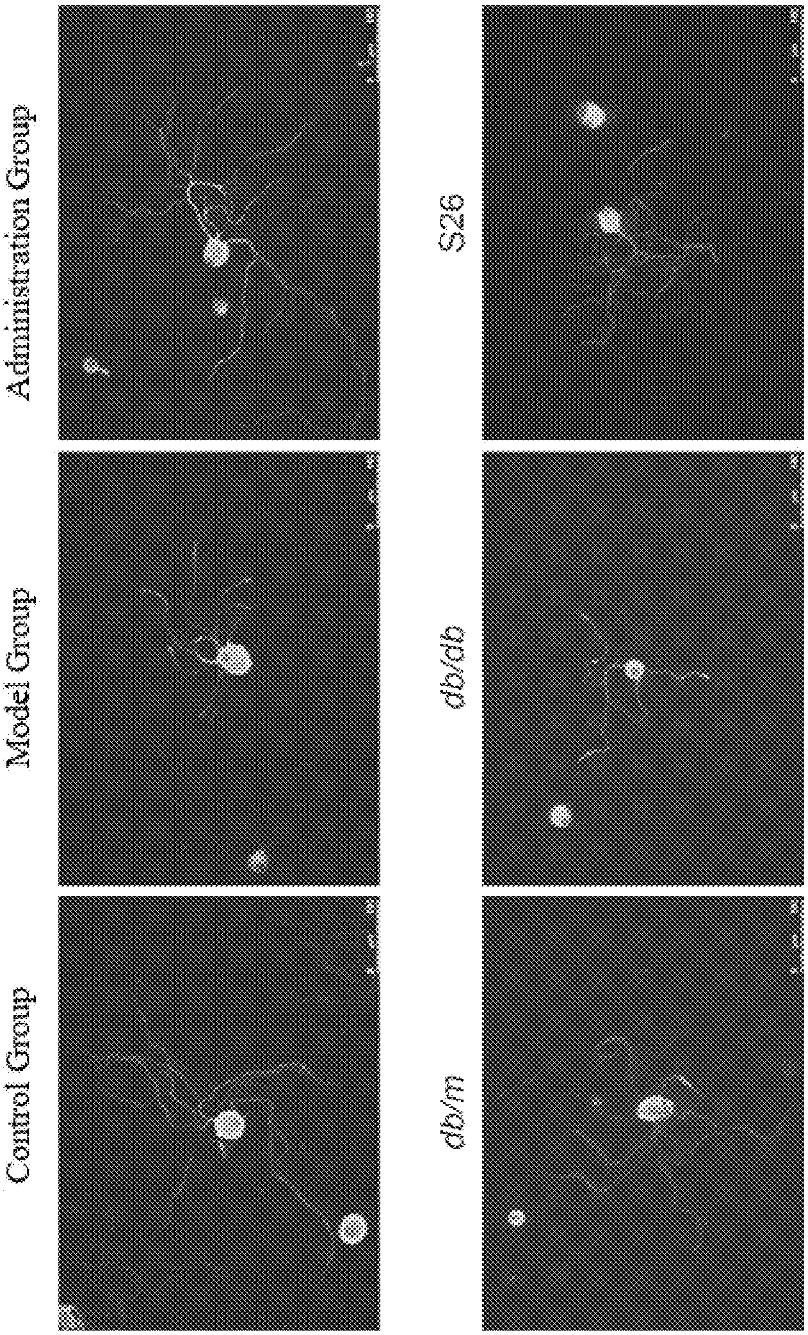
FIG. 1 is an immunofluorescence image showing that a vinpocetine derivative S26 can obviously promote axon growth of peripheral sensory neurons in mice with type 1 and type 2 diabetic peripheral neuropathy.

The present invention is further illustrated hereinafter with reference to the specific embodiments, but these embodiments should not be construed as limiting the present invention.

Example 1: Synthesis of Compound S1

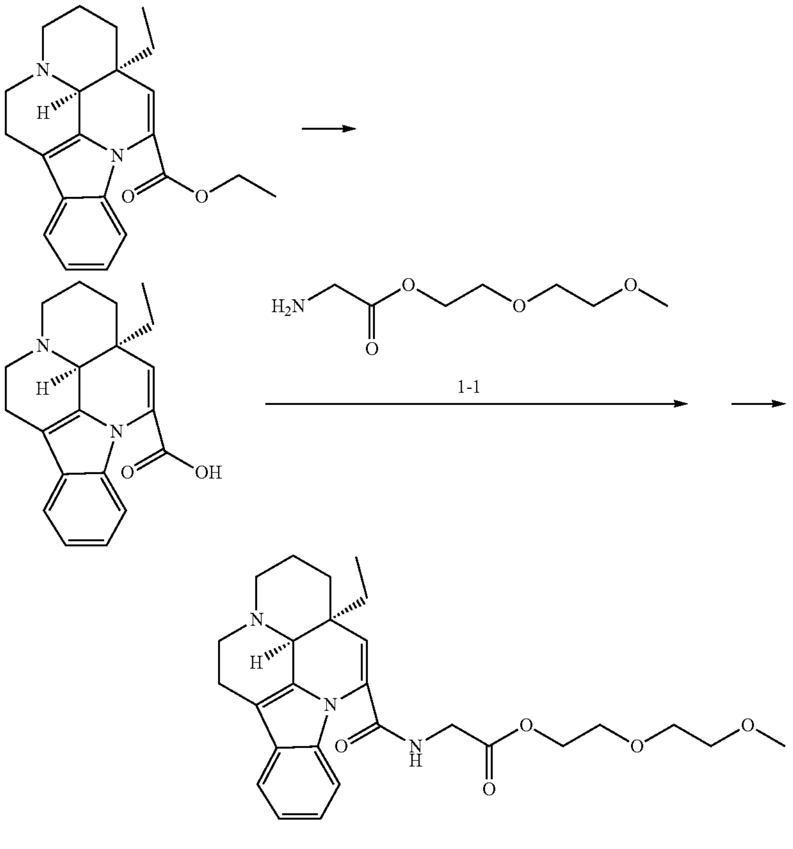

S1

Step 1: Synthesis of Vinpocetine Hydrolyzed Product

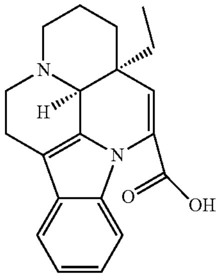

10 g (28.5 mmol) of vinpocetine were dissolved in ethanol, 60 mL of NaOH solution (1 mol/L) were added to the reaction solution above, then heated and refluxed. The solution was gradually clarified from turbid, and the reaction progress was detected by TLC. After the raw materials completely disappeared, the reaction solution was placed at 0° C., and the pH was adjusted to 3 using diluted hydrochloric acid. Then, the ethanol was removed under reduced pressure. The residual solution was filtered, and the filter cake was collected, and dried in vacuum to obtain a vinpocetine hydrolyzed crude product (9.0 g, 98%), which was directly used in next step.

$^1$H NMR (500 MHZ, DMSO-d6) δ 9.80 (s, 1H), 7.56 (ddd, J=19.5, 7.9, 1.2 Hz, 2H), 7.47 (ddd, J=7.9, 7.0, 1.2 Hz, 1H), 7.27 (ddd, J=8.1, 6.9, 1.3 Hz, 1H), 5.79 (s, 1H), 4.57 (s, 1H), 3.06 (ddd, J=11.9, 6.5, 4.2 Hz, 1H), 2.94 (ddd, J=15.6, 6.4, 4.2 Hz, 1H), 2.86-2.77 (m, 2H), 2.75 (ddd, J=12.1, 6.4, 4.2 Hz, 1H), 2.52-2.43 (m, 1H), 1.76-1.51 (m, 5H), 1.42 (dq, J=13.0, 7.2 Hz, 1H), 0.88 (t, J=7.2 Hz, 3H).

Step 2: Synthesis of Compound S1

S1

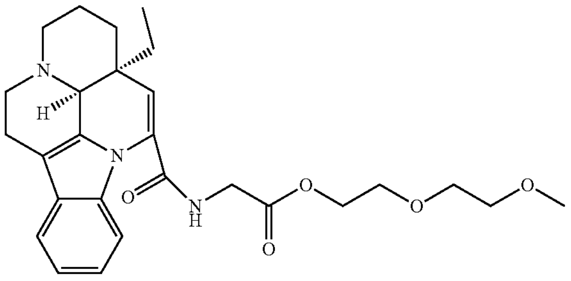

The vinpocetine hydrolyzed product (200 mg, 0.62 mmol), compound 1-1 (122 mg, 0.62 mmol), dicyclohexylcarbodiimide (DCC) (156 mg, 0.76 mmol) and 4-dimethylaminopyridine (DMAP) (8 mg, 0.1 mmol) were dissolved in dichloromethane (2 mL) at room temperature under an atmosphere of nitrogen, and reacted at room temperature for 12 hours. Insoluble materials were removed by suction filtration, and the filtrate was added with water, and extracted with dichloromethane (5 mL×3). The organic phases were combined, washed once with saturated salt water (2 mL), dried over anhydrous sodium sulfate, filtered, concentrated, and subjected to column chromatography separation (column eluent: dichloromethane:methanol=30:1) and purification to obtain a white solid S1 (214 mg, 72.0%).

$^1$H NMR (500 MHZ, DMSO-d$_6$) δ 8.62 (t, J=5.8 Hz, 1H), 7.54 (dd, J=7.8, 1.3 Hz, 2H), 7.46 (ddd, J=7.9, 7.0, 1.4 Hz, 1H), 7.26 (ddd, J=8.1, 6.9, 1.2 Hz, 1H), 5.82 (s, 1H), 4.54 (s, 2H), 4.37 (dt, J=12.4, 6.2 Hz, 1H), 4.13-4.01 (m, 2H), 3.94 (dd, J=17.6, 5.9 Hz, 1H), 3.78-3.42 (m, 6H), 3.39 (s, 2H), 3.09 (ddd, J=12.1, 6.4, 4.2 Hz, 1H), 2.94 (ddd, J=15.6, 6.4, 4.2 Hz, 1H), 2.90-2.75 (m, 2H), 2.72 (ddd, J=12.1, 6.4, 4.2 Hz, 1H), 2.39-2.30 (m, 1H), 1.77-1.68 (m, 3H), 1.72-1.65 (m, 1H), 1.60-1.41 (m, 2H), 0.85 (t, J=7.1 Hz, 3H). MS (ESI, m/z): 482 (M$^+$+1).

For the synthesis of the compounds S2-S52 in the following Examples 2-52, the synthesis of the vinpocetine deethyl ester product in step 1 was the same as that in Example 1, and the reaction process and reaction conditions in step 2 were the same as those in Example 1, and only the compound 1-1 needed to be replaced with a corresponding raw material.

Example 2: Synthesis of Compound S2

In Example 2, the compound 1-1 in Example 1 was replaced with a corresponding raw material 1-2, and a specific structural formula was

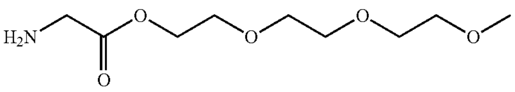

.

-continued

S2

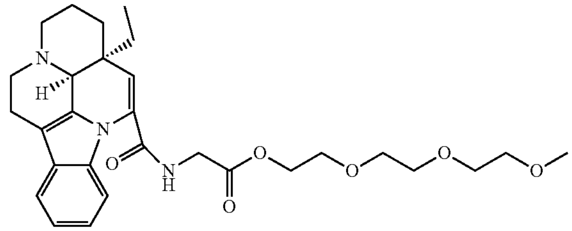

$^1$H NMR (500 MHZ, DMSO-d$_6$) δ 8.62 (t, J=5.8 Hz, 1H), 7.56 (ddd, J=18.4, 7.8, 1.3 Hz, 2H), 7.46 (ddd, J=8.0, 7.0, 1.3 Hz, 1H), 7.26 (ddd, J=8.0, 6.9, 1.3 Hz, 1H), 6.82 (s, 1H), 4.57 (s, 1H), 4.38 (dt, J=12.3, 6.2 Hz, 1H), 4.11-3.97 (m, 2H), 3.92 (dd, J=17.5, 5.8 Hz, 1H), 3.77-3.43 (m, 10H), 3.39 (s, 3H), 3.05 (ddd, J=11.9, 6.5, 4.2 Hz, 1H), 2.92 (ddd, J=15.6, 6.4, 4.3 Hz, 1H), 2.82 (ddd, J=15.4, 6.5, 4.3 Hz, 1H), 2.80-2.71 (m, 2H), 2.46 (ddd, J=12.8, 6.7, 4.8 Hz, 1H), 1.74-1.53 (m, 4H), 1.50-1.42 (m, 1H), 1.46-1.37 (m, 1H), 0.87 (t, J=7.1 Hz, 3H). MS (ESI, m/z): 526 (M$^+$+1).

Example 3: Synthesis of Compound S3

In Example 3, the compound 1-1 in Example 1 was replaced with a corresponding raw material 1-3, and a specific structural formula was

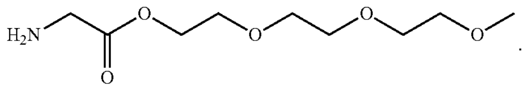

.

S3

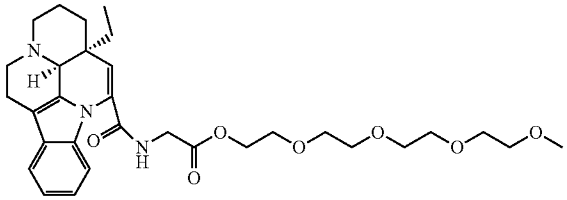

$^1$H NMR (500 MHZ, DMSO-d$_6$) δ 8.62 (t, J=5.8 Hz, 1H), 7.60 (dd, J=8.0, 1.3 Hz, 1H), 7.53 (dd, J=8.0, 1.3 Hz, 1H), 7.47 (ddd, J=8.0, 6.9, 1.3 Hz, 1H), 7.25 (ddd, J=8.0, 6.9, 1.2 Hz, 1H), 6.81 (s, 1H), 4.53 (s, 1H), 4.34 (dt, J=12.3, 6.2 Hz, 1H), 4.21 (dt, J=12.3, 6.2 Hz, 1H), 4.06 (dd, J=17.5, 5.8 Hz, 1H), 3.94 (dd, J=17.6, 5.7 Hz, 1H), 3.77-3.58 (m, 12H), 3.61-3.53 (m, 1H), 3.54-3.42 (m, 2H), 3.39 (s, 3H), 3.09 (ddd, J=12.1, 6.5, 4.2 Hz, 1H), 2.98-2.83 (m, 2H), 2.85-2.71 (m, 2H), 2.36 (ddd, J=11.9, 6.9, 4.7 Hz, 1H), 1.79-1.65 (m, 3H), 1.61-1.46 (m, 3H), 0.86 (t, J=7.2 Hz, 3H). MS (ESI, m/z): 570 (M$^+$+1).

Example 4: Synthesis of Compound S4

In Example 4, the compound 1-1 in Example 1 was replaced with a corresponding raw material 1-4, and a specific structural formula was

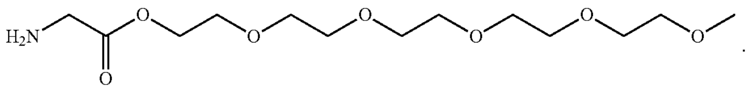

S4

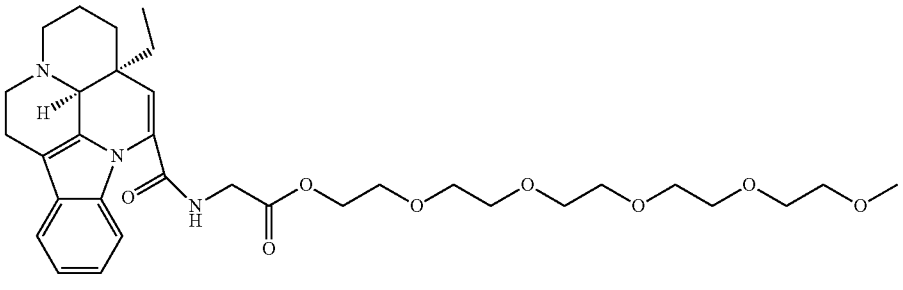

$^1$H NMR (500 MHZ, DMSO-$d_6$) δ 8.61 (t, J=5.8 Hz, 1H), 7.56 (ddd, J=19.9, 7.7, 1.2 Hz, 2H), 7.45 (ddd, J=8.0, 6.9, 1.3 Hz, 1H), 7.27 (ddd, J=8.0, 6.9, 1.3 Hz, 1H), 6.81 (s, 1H), 4.53 (s, 1H), 4.38 (dt, J=12.2, 6.1 Hz, 1H), 4.08 (dt, J=12.4, 6.2 Hz, 1H), 4.02 (dd, J=17.6, 5.9 Hz, 1H), 3.92 (dd, J=17.6, 5.9 Hz, 1H), 3.66 (s, 9H), 3.77-3.42 (m, 10H), 3.39 (s, 3H), 3.05 (ddd, J=12.1, 6.4, 4.3 Hz, 1H), 2.92 (ddd, J=15.4, 6.4, 4.3 Hz, 1H), 2.82 (ddd, J=15.6, 6.5, 4.4 Hz, 1H), 2.80-2.74 (m, 1H), 2.77-2.71 (m, 1H), 2.50-2.40 (m, 1H), 1.75-1.53 (m, 4H), 1.49-1.37 (m, 2H), 0.87 (t, J=7.2 Hz, 3H). MS (ESI, m/z): 614 ($M^+$+1).

Example 5: Synthesis of Compound S5

In Example 5, the compound 1-1 in Example 1 was replaced with a corresponding raw material 1-5, and a specific structural formula was

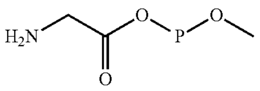

P = PEG-2000 .

S5

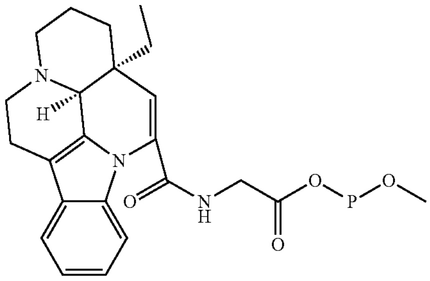

P = PEG-2000

$^1$H NMR (500 MHZ, DMSO-$d_6$) δ 8.56 (t, J=5.8 Hz, 1H), 7.56 (ddd, J=13.4, 7.9, 1.2 Hz, 2H), 7.44 (ddd, J=8.0, 6.9, 1.3 Hz, 1H), 7.26 (ddd, J=8.0, 6.9, 1.3 Hz, 1H), 6.82 (s, 1H), 4.54 (s, 1H), 4.01 (dd, J=17.5, 5.8 Hz, 1H), 3.92 (dd, J=17.6, 5.7 Hz, 1H), 3.51-3.17 (—$OCH_2CH_2$), 3.39 (s, 3H), 3.07 (ddd, J=11.2, 7.2, 4.2 Hz, 1H), 2.96-2.87 (m, 1H), 2.86-2.73 (m, 3H), 2.50 (ddd, J=12.0, 6.9, 4.8 Hz, 1H), 1.74-1.52 (m, 4H), 1.53-1.45 (m, 1H), 1.48-1.39 (m, 1H), 0.88 (t, J=7.1 Hz, 3H).

Example 6: Synthesis of Compound S6

In Example 6, the compound 1-1 in Example 1 was replaced with a corresponding raw material 1-6, and a specific structural formula was

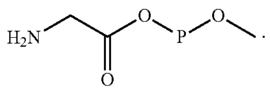

P = PEG-1000

S6

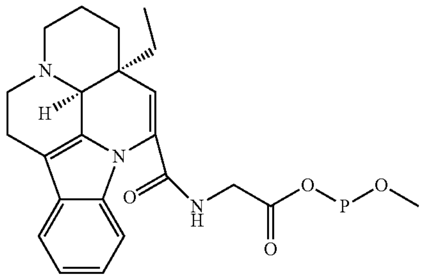

P = PEG-1000

$^1$H NMR (500 MHZ, DMSO-$d_6$) δ 8.56 (t, J=5.8 Hz, 1H), 7.56 (ddd, J=13.4, 7.9, 1.2 Hz, 2H), 7.44 (ddd, J=8.0, 6.9, 1.3 Hz, 1H), 7.26 (ddd, J=8.0, 6.9, 1.3 Hz, 1H), 6.82 (s, 1H), 4.54 (s, 1H), 4.01 (dd, J=17.5, 5.8 Hz, 1H), 3.92 (dd, J=17.6, 5.7 Hz, 1H), 3.51-1H), 2.86-2.73 (m, 3H), 2.50 (ddd, J=12.0, 6.9, 4.8 Hz, 1H), 1.74-1.52 (m, 4H), 1.53-1.45 (m, 1H), 1.48-1.39 (m, 1H), 0.88 (t, J=7.1 Hz, 3H).

Example 7: Synthesis of Compound S7

In Example 7, the compound 1-1 in Example 1 was replaced with a corresponding raw material 1-7, and a specific structural formula was

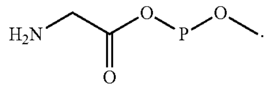

P = PEG-400

-continued

S7

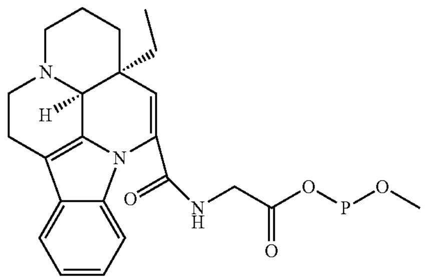

P = PEG-400

$^1$H NMR (500 MHz, DMSO-$d_6$) δ 8.56 (t, J=5.8 Hz, 1H), 7.56 (ddd, J=13.4, 7.9, 1.2 Hz, 2H), 7.44 (ddd, J=8.0, 6.9, 1.3 Hz, 1H), 7.26 (ddd, J=8.0, 6.9, 1.3 Hz, 1H), 6.82 (s, 1H), 4.54 (s, 1H), 4.01 (dd, J=17.5, 5.8 Hz, 1H), 3.92 (dd, J=17.6, 5.7 Hz, 1H), 3.51-3.17 ($-OCH_2CH_2$), 3.39 (s, 3H), 3.07 (ddd, J=11.2, 7.2, 4.2 Hz, 1H), 2.96-2.87 (m, 1H), 2.86-2.73 (m, 3H), 2.50 (ddd, J=12.0, 6.9, 4.8 Hz, 1H), 1.74-1.52 (m, 4H), 1.53-1.45 (m, 1H), 1.48-1.39 (m, 1H), 0.88 (t, J=7.1 Hz, 3H).

Example 8: Synthesis of Compound S8

In Example 8, the compound 1-1 in Example 1 was replaced with a corresponding raw material 1-8, and a specific structural formula was

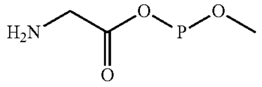

P = PEG-8000 .

S8

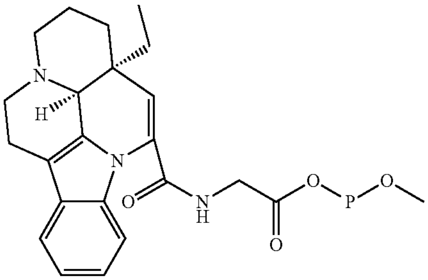

P = PEG-8000

$^1$H NMR (500 MHZ, DMSO-$d_6$) δ 8.56 (t, J=5.8 Hz, 1H), 7.56 (ddd, J=13.4, 7.9, 1.2 Hz, 2H), 7.44 (ddd, J=8.0, 6.9, 1.3 Hz, 1H), 7.26 (ddd, J=8.0, 6.9, 1.3 Hz, 1H), 6.82 (s, 1H), 4.54 (s, 1H), 4.01 (dd, J=17.5, 5.8 Hz, 1H), 3.92 (dd, J=17.6, 5.7 Hz, 1H), 3.51-3.17 ($-OCH_2CH_2$), 3.39 (s, 3H), 3.07 (ddd, J=11.2, 7.2, 4.2 Hz, 1H), 2.96-2.87 (m, 1H), 2.86-2.73 (m, 3H), 2.50 (ddd, J=12.0, 6.9, 4.8 Hz, 1H), 1.74-1.52 (m, 4H), 1.53-1.45 (m, 1H), 1.48-1.39 (m, 1H), 0.88 (t, J=7.1 Hz, 3H).

Example 9: Synthesis of Compound S9

In Example 9, the compound 1-1 in Example 1 was replaced with a corresponding raw material 1-9, and a specific structural formula was

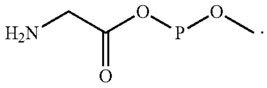

P = PEG-5000

S9

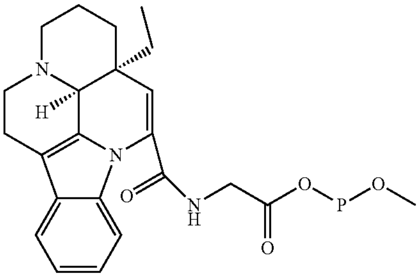

P = PEG-5000

$^1$H NMR (500 MHZ, DMSO-$d_6$) δ 8.56 (t, J=5.8 Hz, 1H), 7.56 (ddd, J=13.4, 7.9, 1.2 Hz, 2H), 7.44 (ddd, J=8.0, 6.9, 1.3 Hz, 1H), 7.26 (ddd, J=8.0, 6.9, 1.3 Hz, 1H), 6.82 (s, 1H), 4.54 (s, 1H), 4.01 (dd, J=17.5, 5.8 Hz, 1H), 3.92 (dd, J=17.6, 5.7 Hz, 1H), 3.51-1H), 2.86-2.73 (m, 3H), 2.50 (ddd, J=12.0, 6.9, 4.8 Hz, 1H), 1.74-1.52 (m, 4H), 1.53-1.45 (m, 1H), 1.48-1.39 (m, 1H), 0.88 (t, J=7.1 Hz, 3H).

Example 10: Synthesis of Compound S10

In Example 10, the compound 1-1 in Example 1 was replaced with a corresponding raw material 1-10, and a specific structural formula was

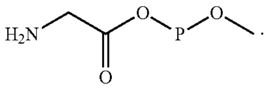

P = PEG-12000

S10

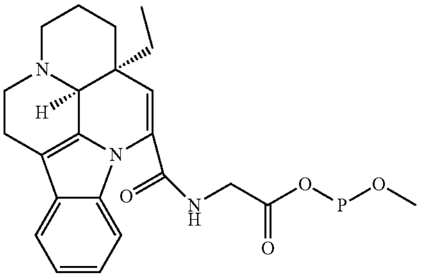

P = PEG-12000

$^1$H NMR (500 MHZ, DMSO-$d_6$) δ 8.56 (t, J=5.8 Hz, 1H), 7.56 (ddd, J=13.4, 7.9, 1.2 Hz, 2H), 7.44 (ddd, J=8.0, 6.9, 1.3 Hz, 1H), 7.26 (ddd, J=8.0, 6.9, 1.3 Hz, 1H), 6.82 (s, 1H), 4.54 (s, 1H), 4.01 (dd, J=17.5, 5.8 Hz, 1H), 3.92 (dd, J=17.6, 5.7 Hz, 1H), 3.51-3.17 ($-OCH_2CH_2$), 3.39 (s, 3H), 3.07 (ddd, J=11.2, 7.2, 4.2 Hz, 1H), 2.96-2.87 (m, 1H), 2.86-2.73 (m, 3H), 2.50 (ddd, J=12.0, 6.9, 4.8 Hz, 1H), 1.74-1.52 (m, 4H), 1.53-1.45 (m, 1H), 1.48-1.39 (m, 1H), 0.88 (t, J=7.1 Hz, 3H).

Example 11: Synthesis of Compound S11

In Example 11, the compound 1-1 in Example 1 was replaced with a corresponding raw material 1-11, and a specific structural formula was

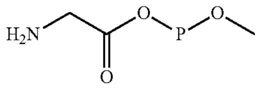

P = PEG-20000 .

S11

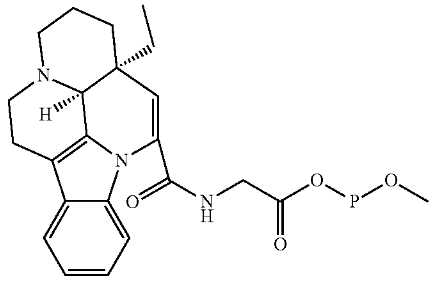

P = PEG-20000

$^1$H NMR (500 MHZ, DMSO-$d_6$) δ 8.56 (t, J=5.8 Hz, 1H), 7.56 (ddd, J=13.4, 7.9, 1.2 Hz, 2H), 7.44 (ddd, J=8.0, 6.9, 1.3 Hz, 1H), 7.26 (ddd, J=8.0, 6.9, 1.3 Hz, 1H), 6.82 (s, 1H), 4.54 (s, 1H), 4.01 (dd, J=17.5, 5.8 Hz, 1H), 3.92 (dd, J=17.6, 5.7 Hz, 1H), 3.51-3.17 ($-OCH_2CH_2$), 3.39 (s, 3H), 3.07 (ddd, J=11.2, 7.2, 4.2 Hz, 1H), 2.96-2.87 (m, 1H), 2.86-2.73 (m, 3H), 2.50 (ddd, J=12.0, 6.9, 4.8 Hz, 1H), 1.74-1.52 (m, 4H), 1.53-1.45 (m, 1H), 1.48-1.39 (m, 1H), 0.88 (t, J=7.1 Hz, 3H).

Example 12: Synthesis of Compound S12

In Example 12, the compound 1-1 in Example 1 was replaced with a corresponding raw material 1-12, and a specific structural formula was

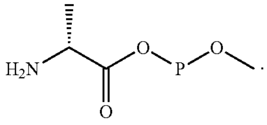

P = PEG-2000

S12

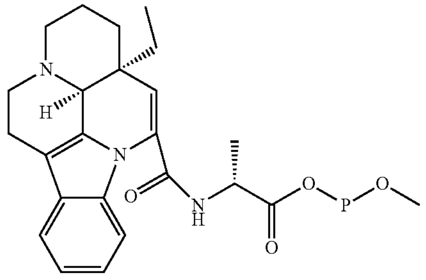

P = PEG-2000

$^1$H NMR (500 MHZ, DMSO-$d_6$) δ 8.66 (d, J=9.3 Hz, 1H), 7.52 (ddd, J=16.6, 7.8, 1.3 Hz, 2H), 7.45 (ddd, J=7.9, 6.8, 1.3 Hz, 1H), 7.26 (ddd, J=8.0, 6.8, 1.3 Hz, 1H), 6.83 (s, 1H), 4.54 (s, 1H), 4.24 (m, 1H), 3.51-3.17 ($-OCH_2CH_2$), 3.39 (s, 3H), 3.06 (ddd, J=12.1, 6.4, 4.3 Hz, 1H), 2.92 (ddd, J=15.6, 6.4, 4.3 Hz, 1H), 2.87-2.79 (m, 1H), 2.82-2.71 (m, 2H), 2.46 (ddd, J=11.9, 7.0, 4.7 Hz, 1H), 1.79-1.52 (m, 5H), 1.45 (dq, J=13.0, 7.2 Hz, 1H), 1.32 (d, J=6.8 Hz, 3H), 0.87 (t, J=7.2 Hz, 3H).

Example 13: Synthesis of Compound S13

In Example 13, the compound 1-1 in Example 1 was replaced with a corresponding raw material 1-13, and a specific structural formula was

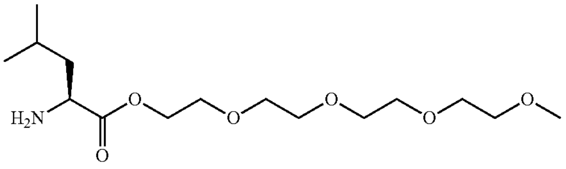

S13

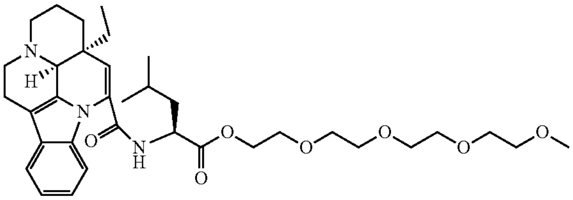

$^1$H NMR (500 MHZ, DMSO-$d_6$) δ 8.58 (d, J=9.3 Hz, 1H), 7.59-7.48 (m, 3H), 7.27 (ddd, J=8.1, 6.8, 1.5 Hz, 1H), 6.82 (s, 1H), 4.53 (s, 1H), 4.45 (dt, J=12.3, 6.1 Hz, 1H), 4.31-4.17 (m, 2H), 3.75-3.63 (m, 8H), 3.67-3.58 (m, 2H), 3.62-3.47 (m, 4H), 3.50-3.42 (m, 1H), 3.39 (s, 3H), 3.07 (ddd, J=11.9, 6.5, 4.3 Hz, 1H), 2.94 (ddd, J=15.4, 6.3, 4.2 Hz, 1H), 2.87-2.72 (m, 3H), 2.51-2.42 (m, 1H), 1.80-1.52 (m, 8H), 1.42 (dq, J=13.0, 7.2 Hz, 1H), 0.96-0.88 (m, 3H), 0.91-0.84 (m, 6H). MS (ESI, m/z): 626 ($M^+$+1).

Example 14: Synthesis of Compound S14

In Example 14, the compound 1-1 in Example 1 was replaced with a corresponding raw material 1-14, and a specific structural formula was

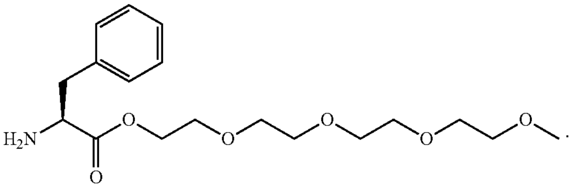

S14

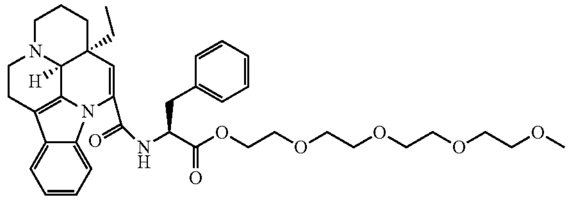

$^1$H NMR (500 MHZ, DMSO-$d_6$) δ 8.83 (d, J=9.3 Hz, 1H), 7.81 (dd, J=8.0, 1.3 Hz, 1H), 7.56 (dd, J=8.0, 1.3 Hz, 1H), 7.50 (ddd, J=7.9, 7.1, 1.3 Hz, 1H), 7.31-7.18 (m, 6H), 6.82 (s, 1H), 4.56 (s, 1H), 4.53-4.33 (m, 3H), 3.67 (s, 4H), 3.75-3.58 (m, 6H), 3.58-3.42 (m, 4H), 3.39 (s, 3H), 3.14-3.04 (m, 2H), 3.06-2.91 (m, 2H), 2.92-2.83 (m, 1H), 2.81 (ddd, J=15.6, 6.5, 4.2 Hz, 1H), 2.73 (ddd, J=11.9, 6.5, 4.2 Hz, 1H), 2.40-2.31 (m, 1H), 1.77-1.66 (m, 3H), 1.61-1.51 (m, 1H), 1.54-1.40 (m, 2H), 0.86 (t, J=7.2 Hz, 3H). MS (ESI, m/z): 660 ($M^+$+1).

Example 15: Synthesis of Compound S15

In Example 15, the compound 1-1 in Example 1 was replaced with a corresponding raw material 1-15, and a specific structural formula was

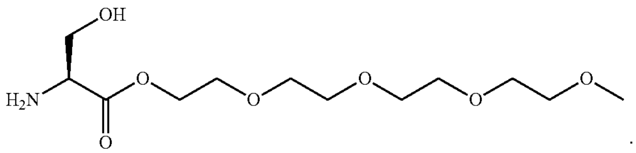

.

S15

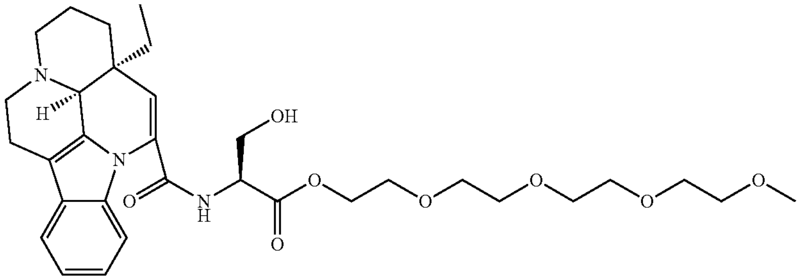

$^1$H NMR (500 MHz, DMSO-$d_6$) δ 8.96 (d, J=9.3 Hz, 1H), 7.64 (dd, J=8.0, 1.3 Hz, 1H), 7.58-7.47 (m, 2H), 7.26 (ddd, J=7.9, 6.9, 1.2 Hz, 1H), 6.82 (s, 1H), 4.55-4.44 (m, 3H), 4.38 (dt, J=12.4, 6.2 Hz, 1H), 4.00-3.91 (m, 1H), 3.91-3.80 (m, 2H), 3.77-3.68 (m, 1H), 3.72-3.62 (m, 8H), 3.65-3.57 (m, 3H), 3.58-3.42 (m, 3H), 3.39 (s, 2H), 3.06 (ddd, J=12.1, 6.5, 4.3 Hz, 1H), 2.93 (ddd, J=15.4, 6.3, 4.2 Hz, 1H), 2.87-2.76 (m, 2H), 2.79-2.72 (m, 1H), 2.48 (ddd, J=11.9, 6.9, 4.8 Hz, 1H), 1.75-1.50 (m, 5H), 1.44 (dq, J=13.0, 7.2 Hz, 1H), 0.88 (t, J=7.2 Hz, 3H). MS (ESI, m/z): 600 ($M^+$+1).

Example 16: Synthesis of Compound S16

In Example 16, the compound 1-1 in Example 1 was replaced with a corresponding raw material 1-16, and a specific structural formula was

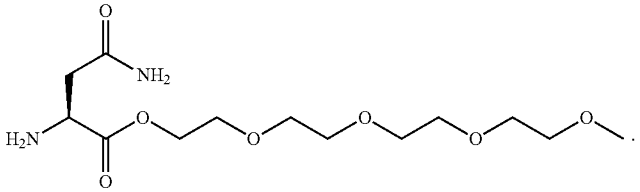

.

S16

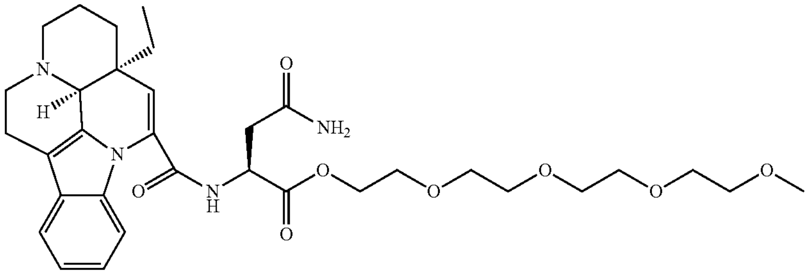

$^1$H NMR (500 MHZ, DMSO-$d_6$) δ 9.15 (d, J=9.3 Hz, 1H), 7.54 (dt, J=7.8, 1.4 Hz, 2H), 7.45 (ddd, J=8.0, 6.9, 1.1 Hz, 1H), 7.27 (ddd, J=8.1, 6.9, 1.3 Hz, 1H), 7.07 (s, 1H), 6.78 (s, 1H), 4.65 (dt, J=9.3, 7.3 Hz, 1H), 4.45 (dt, J=12.4, 6.2 Hz, 1H), 4.27 (dt, J=12.2, 6.2 Hz, 1H), 4.14 (s, 1H), 3.73-3.60 (m, 10H), 3.61 (dd, J=4.0, 2.3 Hz, 1H), 3.59-3.42 (m, 4H), 3.39 (s, 3H), 3.14 (ddd, J=12.1, 6.4, 4.2 Hz, 1H), 3.01 (ddd, J=12.1, 6.5, 4.1 Hz, 1H), 2.92 (ddd, J=15.6, 6.5, 4.2 Hz, 1H), 2.86-2.73 (m, 3H), 2.69 (dd, J=16.9, 7.4 Hz, 1H), 2.53 (ddd, J=12.0, 6.8, 4.7 Hz, 1H), 1.77-1.63 (m, 3H), 1.63-1.44 (m, 3H), 0.85 (t, J=7.2 Hz, 3H). MS (ESI, m/z): 627 ($M^+$+1).

Example 17: Synthesis of Compound S17

In Example 17, the compound 1-1 in Example 1 was replaced with a corresponding raw material 1-17, and a specific structural formula was

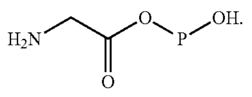

P = PEG-2000

S17

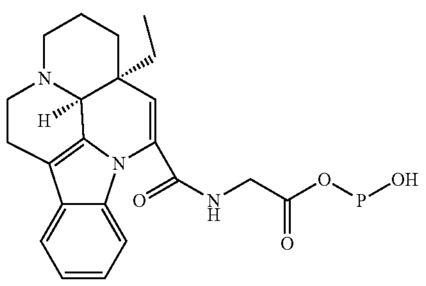

P = PEG-2000

$^1$H NMR (500 MHZ, DMSO-$d_6$) δ 8.64 (t, J=5.8 Hz, 1H), 7.61 (dd, J=7.8, 1.3 Hz, 1H), 7.58-7.49 (m, 2H), 7.26 (ddd, J=8.0, 6.9, 1.3 Hz, 1H), 6.87 (s, 1H), 4.54 (s, 1H), 4.02 (dd, J=17.6, 5.7 Hz, 1H), 3.94 (dd, J=17.6, 5.9 Hz, 1H), 3.51-3.17 (—$OCH_2CH_2$), 3.22 (t, J=6.6 Hz, 1H), 3.08 (ddd, J=11.9, 6.5, 4.2 Hz, 1H), 2.97 (ddd, J=15.6, 6.5, 4.2 Hz, 1H), 2.87-2.76 (m, 2H), 2.73 (ddd, J=12.1, 6.4, 4.2 Hz, 1H), 2.48-2.39 (m, 1H), 1.79-1.40 (m, 6H), 0.85 (t, J=7.2 Hz, 3H).

Example 18: Synthesis of Compound S18

In Example 18, the compound 1-1 in Example 1 was replaced with a corresponding raw material 1-18, and a specific structural formula was

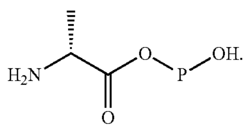

P = PEG-2000

S18

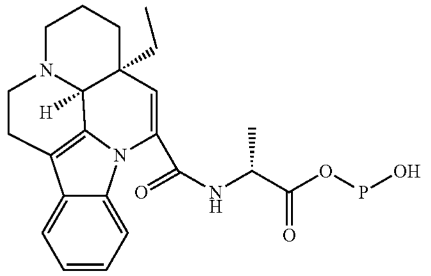

P = PEG-2000

$^1$H NMR (500 MHZ, DMSO-$d_6$) δ 8.60 (d, J=9.2 Hz, 1H), 7.55-7.50 (m, 1H), 7.52-7.41 (m, 2H), 7.26 (ddd, J=8.1, 6.8, 1.5 Hz, 1H), 6.88 (s, 1H), 4.54 (s, 1H), 4.26 (dq, J=9.2, 6.8 Hz, 1H), 3.51-3.17 (—$OCH_2CH_2$), 3.06 (ddd, J=12.1, 6.5, 4.2 Hz, 1H), 2.93 (ddd, J=15.6, 6.4, 4.2 Hz, 1H), 2.86-2.78 (m, 1H), 2.81-2.71 (m, 2H), 2.61 (t, J=6.6 Hz, 1H), 2.48 (ddd, J=11.8, 6.9, 4.8 Hz, 1H), 1.76-1.56 (m, 5H), 1.60-1.52 (m, 1H), 1.43 (dq, J=12.8, 7.2 Hz, 1H), 1.27 (d, J=6.8 Hz, 3H), 0.88 (t, J=7.2 Hz, 3H).

Example 19: Synthesis of Compound S19

In Example 19, the compound 1-1 in Example 1 was replaced with a corresponding raw material 1-19, and a specific structural formula was

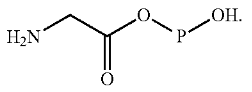

P = PEG-4000

S19

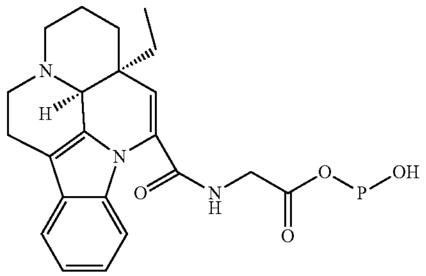

P = PEG-4000

$^1$H NMR (500 MHZ, DMSO-$d_6$) δ 8.64 (t, J=5.8 Hz, 1H), 7.61 (dd, J=7.8, 1.3 Hz, 1H), 7.58-7.49 (m, 2H), 7.26 (ddd, J=8.0, 6.9, 1.3 Hz, 1H), 6.87 (s, 1H), 4.54 (s, 1H), 4.02 (dd, J=17.6, 5.7 Hz, 1H), 3.94 (dd, J=17.6, 5.9 Hz, 1H), 3.51-3.17 (—$OCH_2CH_2$), 3.22 (t, J=6.6 Hz, 1H), 3.08 (ddd, J=11.9, 6.5, 4.2 Hz, 1H), 2.97 (ddd, J=15.6, 6.5, 4.2 Hz, 1H), 2.87-2.76 (m, 2H), 2.73 (ddd, J=12.1, 6.4, 4.2 Hz, 1H), 2.48-2.39 (m, 1H), 1.79-1.40 (m, 6H), 0.85 (t, J=7.2 Hz, 3H).

Example 20: Synthesis of Compound S20

In Example 20, the compound 1-1 in Example 1 was replaced with a corresponding raw material 1-20, and a specific structural formula was

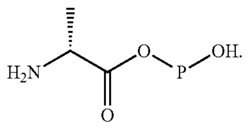

P = PEG-4000

S20

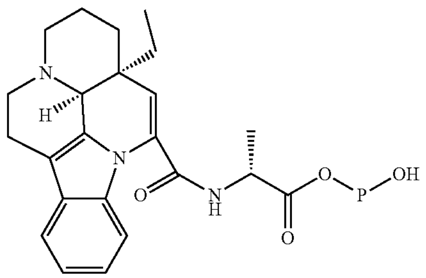

P = PEG-4000

$^1$H NMR (500 MHZ, DMSO-$d_6$) δ 8.60 (d, J=9.2 Hz, 1H), 7.55-7.50 (m, 1H), 7.52-7.41 (m, 2H), 7.26 (ddd, J=8.1, 6.8, 1.5 Hz, 1H), 6.88 (s, 1H), 4.54 (s, 1H), 4.26 (dq, J=9.2, 6.8 Hz, 1H), 3.51-3.17 (—$OCH_2CH_2$), 3.06 (ddd, J=12.1, 6.5, 4.2 Hz, 1H), 2.93 (ddd, J=15.6, 6.4, 4.2 Hz, 1H), 2.86-2.78 (m, 1H), 2.81-2.71 (m, 2H), 2.61 (t, J=6.6 Hz, 1H), 2.48 (ddd, J=11.8, 6.9, 4.8 Hz, 1H), 1.76-1.56 (m, 5H), 1.60-1.52 (m, 1H), 1.43 (dq, J=12.8, 7.2 Hz, 1H), 1.27 (d, J=6.8 Hz, 3H), 0.88 (t, J=7.2 Hz, 3H).

Example 21: Synthesis of Compound S21

In Example 21, the compound 1-1 in Example 1 was replaced with a corresponding raw material 1-21, and a specific structural formula was

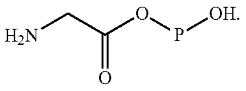

P = PEG-400

S21

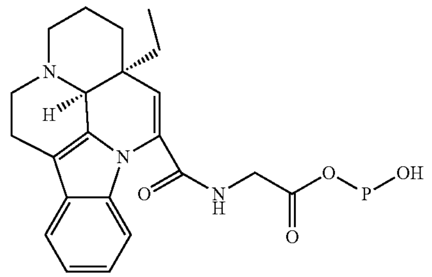

P = PEG-400

$^1$H NMR (500 MHz, DMSO-$d_6$) δ 8.64 (t, J=5.8 Hz, 1H), 7.61 (dd, J=7.8, 1.3 Hz, 1H), 7.58-7.49 (m, 2H), 7.26 (ddd, J=8.0, 6.9, 1.3 Hz, 1H), 6.87 (s, 1H), 4.54 (s, 1H), 4.02 (dd, J=17.6, 5.7 Hz, 1H), 3.94 (dd, J=17.6, 5.9 Hz, 1H), 3.51-3.17 (—$OCH_2CH_2$), 3.22 (t, J=6.6 Hz, 1H), 3.08 (ddd, J=11.9, 6.5, 4.2 Hz, 1H), 2.97 (ddd, J=15.6, 6.5, 4.2 Hz, 1H), 2.87-2.76 (m, 2H), 2.73 (ddd, J=12.1, 6.4, 4.2 Hz, 1H), 2.48-2.39 (m, 1H), 1.79-1.40 (m, 6H), 0.85 (t, J=7.2 Hz, 3H).

Example 22: Synthesis of Compound S22

In Example 22, the compound 1-1 in Example 1 was replaced with a corresponding raw material 1-22, and a specific structural formula was

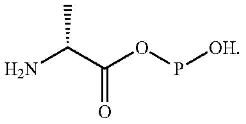

P = PEG-400

-continued

S22

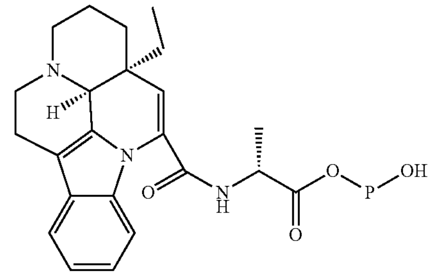

P = PEG-400

$^1$H NMR (500 MHZ, DMSO-$d_6$) δ 8.60 (d, J=9.2 Hz, 1H), 7.55-7.50 (m, 1H), 7.52-7.41 (m, 2H), 7.26 (ddd, J=8.1, 6.8, 1.5 Hz, 1H), 6.88 (s, 1H), 4.54 (s, 1H), 4.26 (dq, J=9.2, 6.8 Hz, 1H), 3.51-3.17 (—$OCH_2CH_2$), 3.06 (ddd, J=12.1, 6.5, 4.2 Hz, 1H), 2.93 (ddd, J=15.6, 6.4, 4.2 Hz, 1H), 2.86-2.78 (m, 1H), 2.81-2.71 (m, 2H), 2.61 (t, J=6.6 Hz, 1H), 2.48 (ddd, J=11.8, 6.9, 4.8 Hz, 1H), 1.76-1.56 (m, 5H), 1.60-1.52 (m, 1H), 1.43 (dq, J=12.8, 7.2 Hz, 1H), 1.27 (d, J=6.8 Hz, 3H), 0.88 (t, J=7.2 Hz, 3H).

Example 23: Synthesis of Compound S23

In Example 23, the compound 1-1 in Example 1 was replaced with a corresponding raw material 1-23, and a specific structural formula was

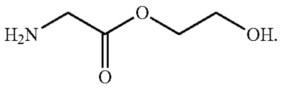

S23

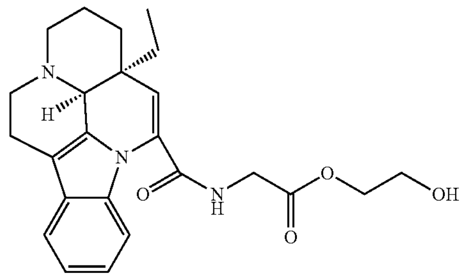

$^1$H NMR (500 MHZ, DMSO-$d_6$) δ 8.65 (t, J=5.8 Hz, 1H), 7.56 (ddd, J=16.1, 7.8, 1.2 Hz, 2H), 7.45 (ddd, J=7.9, 7.0, 1.2 Hz, 1H), 7.26 (ddd, J=8.1, 6.9, 1.3 Hz, 1H), 6.82 (s, 1H), 4.54 (s, 1H), 4.34 (dt, J=12.2, 6.5 Hz, 1H), 4.11 (dt, J=12.1, 6.5 Hz, 1H), 3.99 (dd, J=17.5, 5.8 Hz, 1H), 3.89 (dd, J=17.6, 5.9 Hz, 1H), 3.85-3.74 (m, 2H), 3.06 (ddd, J=12.1, 6.4, 4.2 Hz, 1H), 2.92 (ddd, J=15.6, 6.4, 4.3 Hz, 1H), 2.88-2.71 (m, 4H), 2.51-2.42 (m, 1H), 1.75-1.48 (m, 5H), 1.42 (dq, J=13.0, 7.2 Hz, 1H), 0.87 (t, J=7.2 Hz, 3H). MS (ESI, m/z): 424 ($M^+$+1).

Example 24: Synthesis of Compound S24

In Example 24, the compound 1-1 in Example 1 was replaced with a corresponding raw material 1-24, and a specific structural formula was

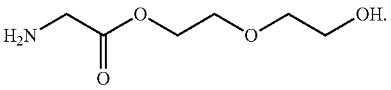

S24

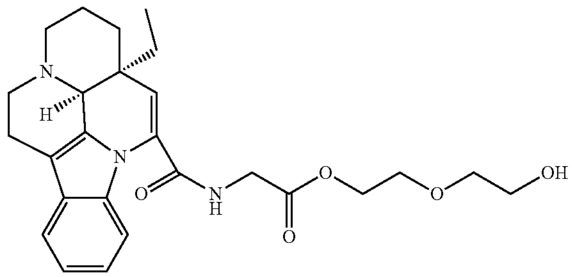

$^1$H NMR (500 MHZ, DMSO-$d_6$) δ 8.61 (t, J=5.8 Hz, 1H), 7.56-7.50 (m, 1H), 7.51-7.42 (m, 2H), 7.26 (ddd, J=8.1, 6.4, 1.9 Hz, 1H), 6.82 (s, 1H), 4.54 (s, 1H), 4.25 (dt, J=12.3, 6.1 Hz, 1H), 4.10 (dt, J=12.3, 6.2 Hz, 1H), 3.97 (dd, J=17.5, 5.8 Hz, 1H), 3.90 (dd, J=17.5, 5.8 Hz, 1H), 3.84-3.49 (m, 6H), 3.44 (dt, J=12.3, 6.3 Hz, 1H), 3.06 (ddd, J=11.9, 6.5, 4.2 Hz, 1H), 2.93 (ddd, J=15.4, 6.4, 4.2 Hz, 1H), 2.86-2.71 (m, 3H), 2.48 (ddd, J=11.9, 6.9, 4.7 Hz, 1H), 1.75-1.51 (m, 5H), 1.43 (dq, J=13.0, 7.2 Hz, 1H), 0.87 (t, J=7.2 Hz, 3H). MS (ESI, m/z): 468 ($M^+$+1).

Example 25: Synthesis of Compound S25

In Example 25, the compound 1-1 in Example 1 was replaced with a corresponding raw material 1-25, and a specific structural formula was

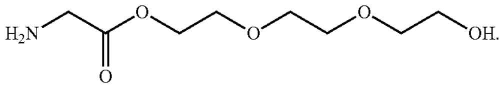

S25

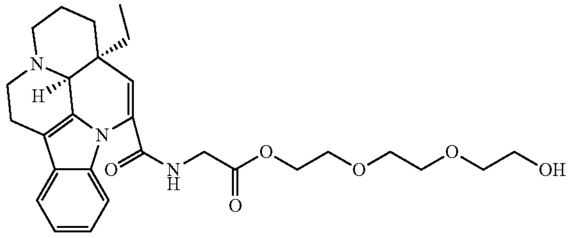

$^1$H NMR (500 MHZ, DMSO-$d_6$) δ 8.62 (t, J=5.8 Hz, 1H), 7.66-7.60 (m, 1H), 7.53 (dd, J=7.6, 1.2 Hz, 1H), 7.47 (ddd, J=8.0, 6.9, 1.3 Hz, 1H), 7.26 (ddd, J=7.9, 6.9, 1.2 Hz, 1H), 6.82 (s, 1H), 4.54 (s, 1H), 4.31 (dt, J=12.3, 6.1 Hz, 1H), 4.14 (dt, J=12.3, 6.1 Hz, 1H), 4.01 (dd, J=17.5, 5.8 Hz, 1H), 3.91 (dd, J=17.6, 5.7 Hz, 1H), 3.84-3.70 (m, 3H), 3.73-3.66 (m, 3H), 3.69-3.61 (m, 2H), 3.65-3.54 (m, 2H), 3.48 (dt, J=12.4, 6.3 Hz, 1H), 3.06 (ddd, J=12.1, 6.4, 4.3 Hz, 1H), 2.90 (ddd, J=15.4, 6.2, 4.2 Hz, 1H), 2.87-2.70 (m, 3H), 2.44 (ddd, J=12.0, 6.9, 4.8 Hz, 1H), 1.76-1.42 (m, 6H), 0.87 (t, J=7.2 Hz, 3H). MS (ESI, m/z): 512 ($M^+$+1).

Example 26: Synthesis of Compound S26

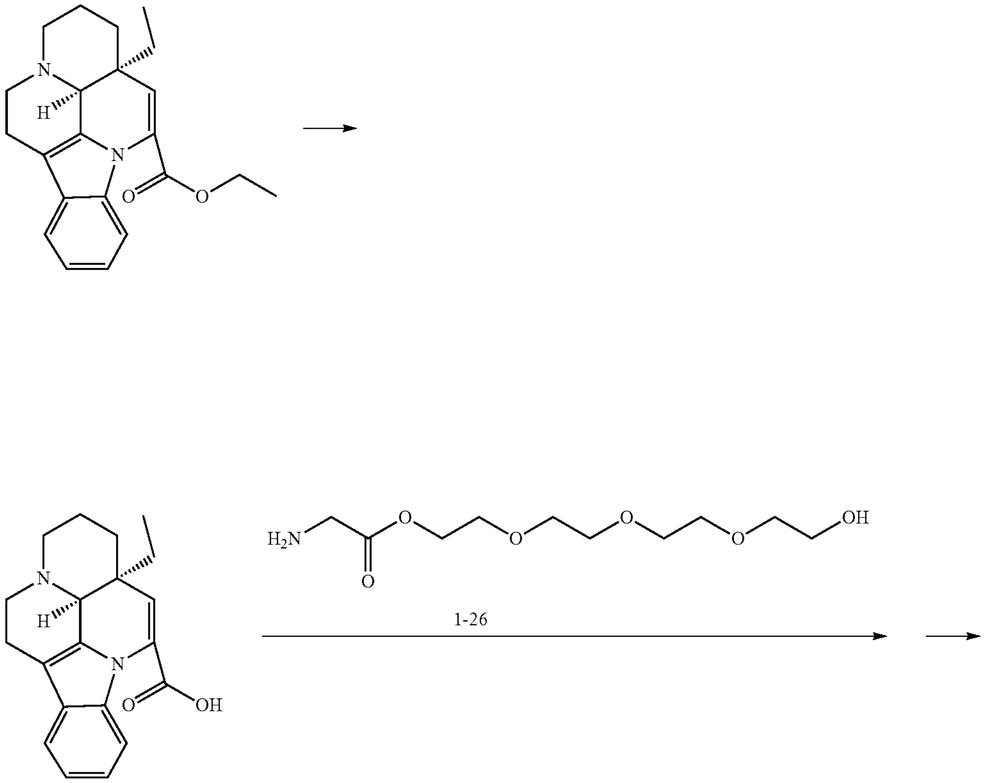

-continued

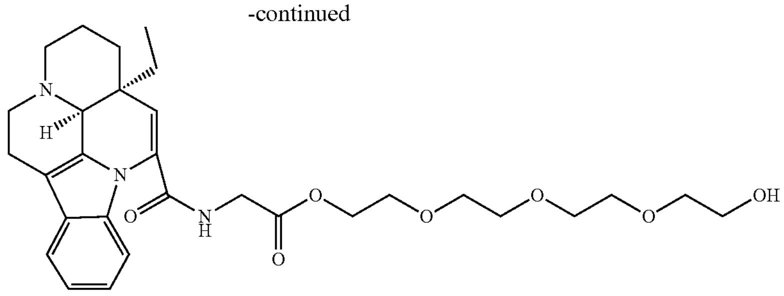

S26

Step 1: Synthesis of Vinpocetine Hydrolyzed Product

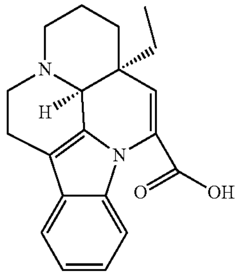

10 g (28.5 mmol) of vinpocetine were dissolved in ethanol, 60 mL of NaOH solution (1 mol/L) were added to the reaction solution above, then heated and refluxed. The solution was gradually clarified from turbid, and a reaction progress was detected by TLC. After the raw materials completely disappeared, the reaction solution was placed at 0° C., and the pH was adjusted to 3 with diluted hydrochloric acid, and then the ethanol was removed under reduced pressure. The residual solution was filtered, and then filter cake was collected, and dried in vacuum to obtain a vinpocetine crude hydrolyzed product (9.0 g, 98%), which was directly used in next step.

$^1$H NMR (500 MHZ, DMSO-$d_6$) δ 9.80 (s, 1H), 7.56 (ddd, J=19.5, 7.9, 1.2 Hz, 2H), 7.47 (ddd, J=7.9, 7.0, 1.2 Hz, 1H), 7.27 (ddd, J=8.1, 6.9, 1.3 Hz, 1H), 5.79 (s, 1H), 4.57 (s, 1H), 3.06 (ddd, J=11.9, 6.5, 4.2 Hz, 1H), 2.94 (ddd, J=15.6, 6.4, 4.2 Hz, 1H), 2.86-2.77 (m, 2H), 2.75 (ddd, J=12.1, 6.4, 4.2 Hz, 1H), 2.52-2.43 (m, 1H), 1.76-1.51 (m, 5H), 1.42 (dq, J=13.0, 7.2 Hz, 1H), 0.88 (t, J=7.2 Hz, 3H).

Step 2: Synthesis of Compound S26

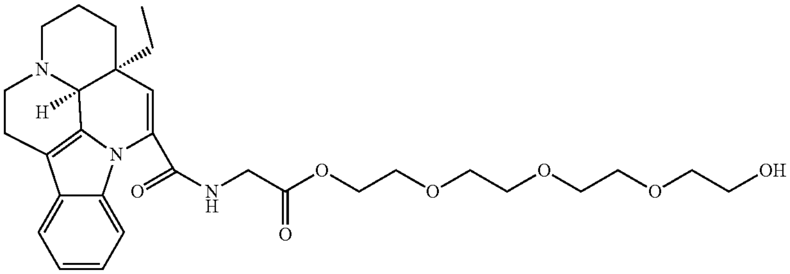

S26

The vinpocetine hydrolyzed product (200 mg, 0.62 mmol), compound 1-26 (155 mg, 0.62 mmol), DCC (156 mg, 0.76 mmol) and DMAP (8 mg, 0.1 mmol) were dissolved in 2 mL of dichloromethane at room temperature under an atmosphere of nitrogen, and reacted at room temperature for 12 hours. Insoluble materials were removed by suction filtration, the filtrate was added with water, and extracted with dichloromethane (5 mL×3). The organic phases were combined, washed once with saturated salt water (2 mL), dried over anhydrous sodium sulfate, filtered, concentrated, and subjected to chromatography separation (column dichloromethane:methanol=30:1) and purification to obtain a white solid S26 (278 mg, 81.0%). 1H NMR (500 MHZ, DMSO-$d_6$) δ 8.61 (t, J=5.8 Hz, 1H), 7.52 (dt, J=7.8, 0.9 Hz, 1H), 7.51-7.42 (m, 2H), 7.26 (ddd, J=8.1, 6.1, 2.0 Hz, 1H), 6.81 (s, 1H), 4.33 (dt, J=12.2, 6.1 Hz, 1H), 4.12 (dt, J=12.4, 6.3 Hz, 1H), 4.06-3.87 (m, 3H), 3.84-3.72 (m, 2H), 3.76-3.66 (m, 6H), 3.70-3.57 (m, 6H), 3.51 (dt, J=11.8, 6.6 Hz, 1H), 3.14 (ddd, J=12.1, 6.4, 4.2 Hz, 1H), 3.01 (ddd, J=12.1, 6.4, 4.2 Hz, 1H), 2.91 (ddd, J=15.4, 6.4, 4.1 Hz, 1H), 2.86-2.73 (m, 2H), 2.56 (ddd, J=12.0, 7.1, 4.8 Hz, 1H), 1.78-1.64 (m, 3H), 1.61-1.49 (m, 1H), 1.51-1.40 (m, 2H), 0.88 (t, J=7.2 Hz, 3H). MS (ESI, m/z): 556 ($M^+$+1).

Example 27: Synthesis of Compound S27

In Example 27, the compound 1-1 in Example 1 was replaced with a corresponding raw material 1-27, and a specific structural formula was

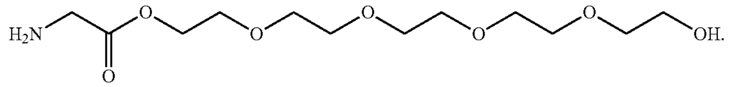

S27

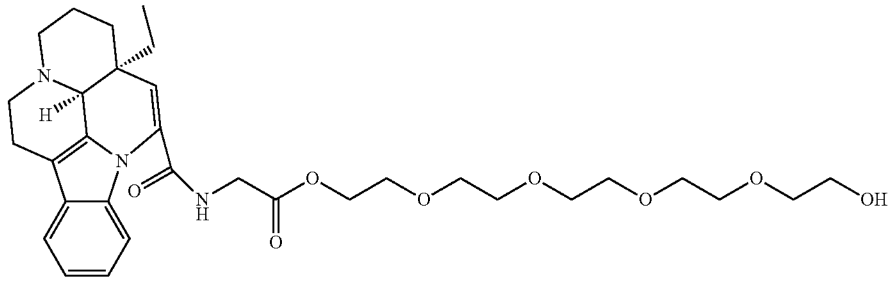

$^1H$ NMR (500 MHZ, DMSO-$d_6$) δ 8.67 (t, J=5.8 Hz, 1H), 7.62 (dd, J=7.8, 1.3 Hz, 1H), 7.53 (dd, J=8.0, 1.3 Hz, 1H), 7.43 (ddd, J=8.0, 7.0, 1.3 Hz, 1H), 7.26 (ddd, J=8.1, 6.9, 1.3 Hz, 1H), 6.81 (s, 1H), 4.53 (s, 1H), 4.38 (dt, J=12.2, 6.1 Hz, 1H), 4.13 (dt, J=12.4, 6.2 Hz, 1H), 4.00 (dd, J=17.5, 5.8 Hz, 1H), 3.94 (dd, J=17.6, 5.9 Hz, 1H), 3.83-3.74 (m, 1H), 3.77-3.70 (m, 3H), 3.74-3.57 (m, 16H), 3.46 (dt, J=12.1, 6.5 Hz, 1H), 3.05 (ddd, J=12.1, 6.4, 4.2 Hz, 1H), 2.85-2.70 (m, 2H), 2.51-2.42 (m, 1H), 1.75-1.41 (m, 6H), 0.85 (t, J=7.2 Hz, 3H). MS (ESI, m/z): 660 ($M^+$+1).

Example 28: Synthesis of Compound S28

In Example 28, the compound 1-1 in Example 1 was replaced with a corresponding raw material 1-28, and a specific structural formula was

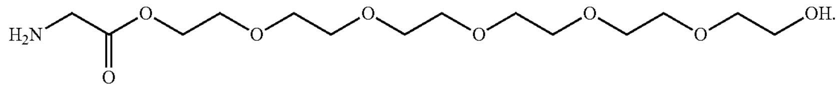

28

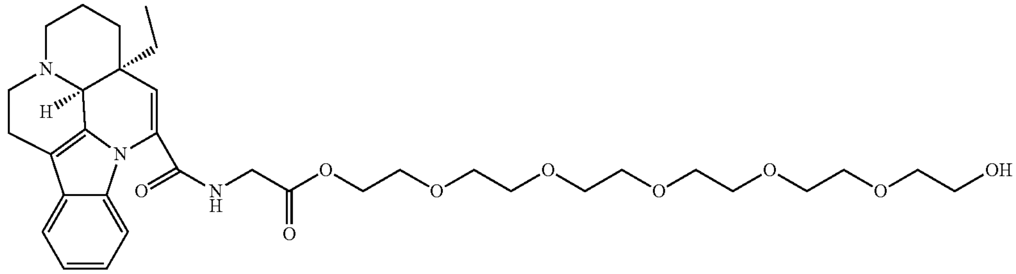

$^1H$ NMR (500 MHZ, DMSO-$d_6$) δ 8.62 (t, J=5.8 Hz, 1H), 7.62 (dd, J=7.8, 1.3 Hz, 1H), 7.54 (dd, J=7.9, 1.2 Hz, 1H), 7.42 (ddd, J=7.8, 6.9, 1.2 Hz, 1H), 7.25 (ddd, J=8.1, 7.0, 1.3 Hz, 1H), 4.40 (dt, J=12.3, 6.1 Hz, 1H), 4.15-3.99 (m, 3H), 3.96 (dd, J=17.6, 5.7 Hz, 1H), 3.83-3.54 (m, 24H), 3.12 (ddd, J=12.1, 6.4, 4.2 Hz, 1H), 3.00 (ddd, J=12.1, 6.6, 4.2 Hz, 1H), 2.90 (ddd, J=15.4, 6.5, 4.2 Hz, 1H), 2.84-2.72 (m, 2H), 2.63 (ddd, J=12.0, 7.0, 4.8 Hz, 1H), 1.80-1.67 (m, 2H), 1.63-1.39 (m, 4H), 0.87 (t, J=7.2 Hz, 3H). MS (ESI, m/z): 644 ($M^+$+1).

Example 29: Synthesis of Compound S29

In Example 29, the compound 1-1 in Example 1 was replaced with a corresponding raw material 1-29, and a specific structural formula was

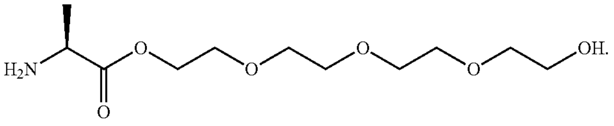

S29

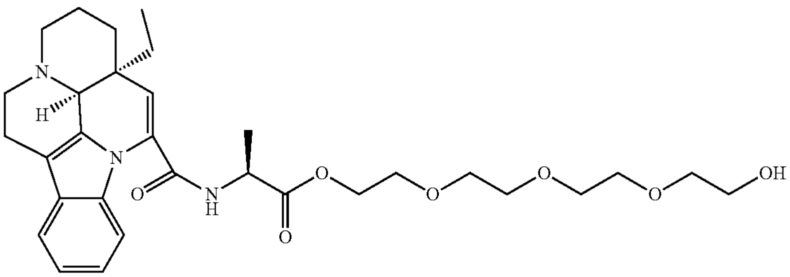

$^1$H NMR (500 MHZ, DMSO-$d_6$) δ 8.66 (d, J=9.2 Hz, 1H), 7.55 (ddd, J=11.9, 7.9, 1.3 Hz, 2H), 7.47 (ddd, J=8.0, 6.9, 1.2 Hz, 1H), 7.25 (ddd, J=8.0, 6.9, 1.2 Hz, 1H), 6.82 (s, 1H), 4.53 (s, 1H), 4.45 (dt, J=12.3, 6.1 Hz, 1H), 4.30-4.21 (m, 2H), 3.84-3.44 (m, 16H), 3.06 (ddd, J=12.1, 6.5, 4.3 Hz, 1H), 2.93 (ddd, J=15.6, 6.4, 4.3 Hz, 1H), 2.82 (ddd, J=15.6, 6.4, 4.2 Hz, 1H), 2.82-2.75 (m, 1H), 2.79-2.72 (m, 1H), 2.51-2.42 (m, 1H), 1.74-1.49 (m, 5H), 1.41 (dq, J=12.8, 7.2 Hz, 1H), 1.29 (d, J=6.8 Hz, 2H), 0.87 (t, J=7.2 Hz, 3H). MS (ESI, m/z): 570 ($M^+$+1).

Example 30: Synthesis of Compound S30

In Example 30, the compound 1-1 in Example 1 was replaced with a corresponding raw material 1-30, and a specific structural formula was

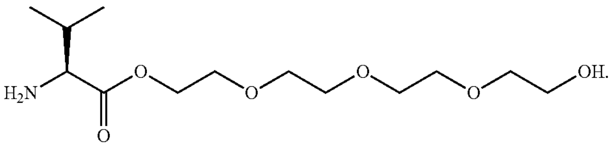

S30

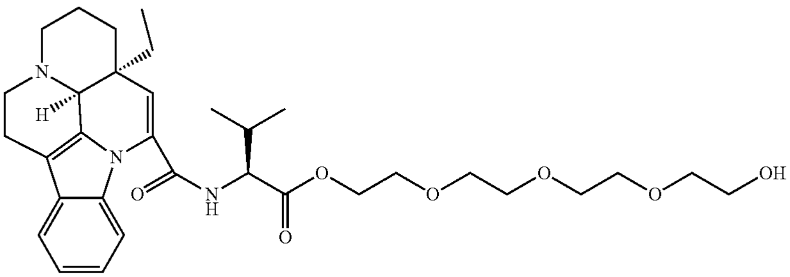

$^1$H NMR (500 MHZ, DMSO-$d_6$) δ 8.70 (d, J=9.1 Hz, 1H), 7.55 (ddd, J=12.1, 7.8, 1.2 Hz, 2H), 7.45 (ddd, J=8.0, 6.9, 1.3 Hz, 1H), 7.27 (ddd, J=8.0, 6.9, 1.3 Hz, 1H), 6.82 (s, 1H), 4.53 (s, 1H), 4.38 (dt, J=12.2, 6.1 Hz, 1H), 4.21-4.11 (m, 2H), 3.83-3.43 (m, 15H), 3.07 (ddd, J=12.1, 6.4, 4.2 Hz, 1H), 2.93 (ddd, J=15.6, 6.4, 4.3 Hz, 1H), 2.87-2.72 (m, 3H), 2.51-2.42 (m, 1H), 2.15-2.02 (m, J=6.6 Hz, 1H), 1.74-1.52 (m, 5H), 1.41 (dq, J=13.0, 7.2 Hz, 1H), 0.95 (dd, J=25.0, 6.7 Hz, 6H), 0.87 (t, J=7.2 Hz, 3H). MS (ESI, m/z): 598 ($M^+$+1).

Example 31: Synthesis of Compound S31

In Example 31, the compound 1-1 in Example 1 was replaced with a corresponding raw material 1-31, and a specific structural formula was

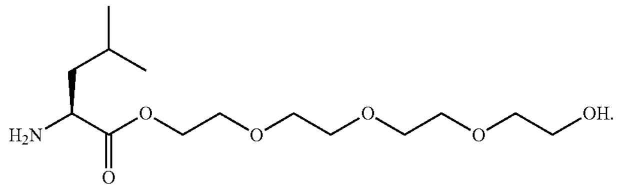

S31

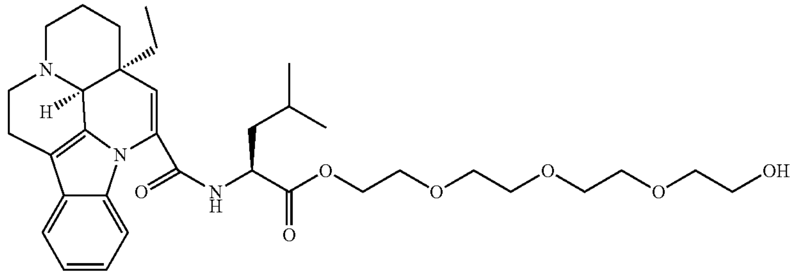

$^1$H NMR (500 MHZ, DMSO-$d_6$) δ 8.59 (d, J=9.3 Hz, 1H), 7.53 (dt, J=7.8, 0.8 Hz, 1H), 7.50-7.41 (m, 2H), 7.27 (ddd, J=8.1, 5.8, 2.5 Hz, 1H), 6.82 (s, 1H), 4.55-4.37 (m, 3H), 4.29 (dt, J=12.2, 6.1 Hz, 1H), 3.83-3.50 (m, 15H), 3.06 (ddd, J=12.1, 6.4, 4.2 Hz, 1H), 2.93 (ddd, J=15.6, 6.4, 4.3 Hz, 1H), 2.86-2.71 (m, 3H), 2.46 (ddd, J=11.8, 6.8, 4.8 Hz, 1H), 1.81 (dt, J=13.6, 6.8 Hz, 1H), 1.77-1.51 (m, 7H), 1.41 (dq, J=13.0, 7.2 Hz, 1H), 0.95-0.85 (m, 9H). MS (ESI, m/z): 612 ($M^+$+1).

Example 32: Synthesis of Compound S32

In Example 32, the compound 1-1 in Example 1 was replaced with a corresponding raw material 1-32, and a specific structural formula was

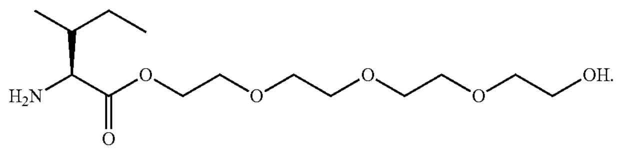

S32

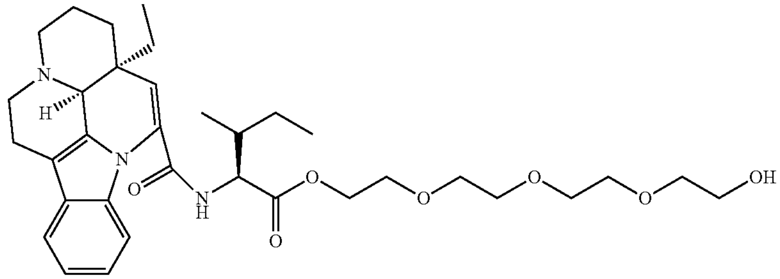

$^1$H NMR (500 MHZ, DMSO-$d_6$) δ 8.51 (d, J=9.1 Hz, 1H), 7.53 (dd, J=8.0, 1.3 Hz, 1H), 7.45 (ddd, J=8.1, 6.9, 1.3 Hz, 1H), 7.39 (dd, J=7.8, 1.4 Hz, 1H), 7.27 (ddd, J=8.0, 6.9, 1.4 Hz, 1H), 6.82 (s, 1H), 4.29 (dd, J=9.0, 6.6 Hz, 1H), 4.22 (dt, J=12.3, 6.1 Hz, 1H), 4.17-4.08 (m, 2H), 3.83-3.55 (m, 14H), 3.48 (ddt, J=13.1, 12.1, 6.4 Hz, 2H), 3.12 (dt, J=12.1, 5.3 Hz, 1H), 2.96 (ddd, J=12.1, 5.9, 4.7 Hz, 1H), 2.95-2.84 (m, 2H), 2.86-2.77 (m, 1H), 2.57 (ddd, J=11.7, 6.9, 4.6 Hz, 1H), 1.83-1.46 (m, 7H), 1.40-1.28 (m, 1H), 0.94-0.82 (m, 9H). MS (ESI, m/z): 612 ($M^+$+1).

Example 33: Synthesis of Compound S33

In Example 33, the compound 1-1 in Example 1 was replaced with a corresponding raw material 1-33, and a specific structural formula was

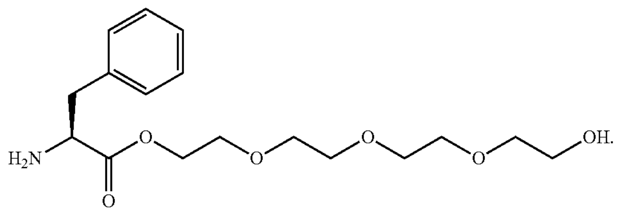

S33

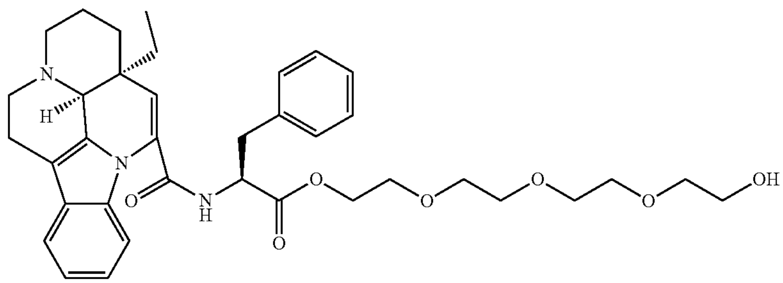

$^1$H NMR (500 MHz, DMSO-$d_6$) δ 8.74 (d, J=9.3 Hz, 1H), 7.60-7.54 (m, 1H), 7.48-7.39 (m, 2H), 7.31-7.18 (m, 6H), 6.82 (s, 1H), 4.59 (dt, J=9.3, 7.7 Hz, 1H), 4.55-4.44 (m, 2H), 4.27 (dt, J=12.4, 6.2 Hz, 1H), 3.78 (ddt, J=12.8, 7.5, 6.5 Hz, 1H), 3.75-3.64 (m, 6H), 3.68-3.61 (m, 3H), 3.64-3.43 (m, 5H), 3.11-2.99 (m, 2H), 3.01-2.90 (m, 2H), 2.88-2.72 (m, 3H), 2.51-2.42 (m, 1H), 1.75-1.48 (m, 5H), 1.41 (dq, J=12.8, 7.2 Hz, 1H), 0.86 (t, J=7.2 Hz, 3H). MS (ESI, m/z): 646 ($M^+$+1).

Example 34: Synthesis of Compound S34

In Example 34, the compound 1-1 in Example 1 was replaced with a corresponding raw material 1-34, and a specific structural formula was

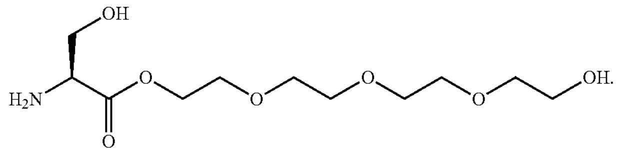

S34

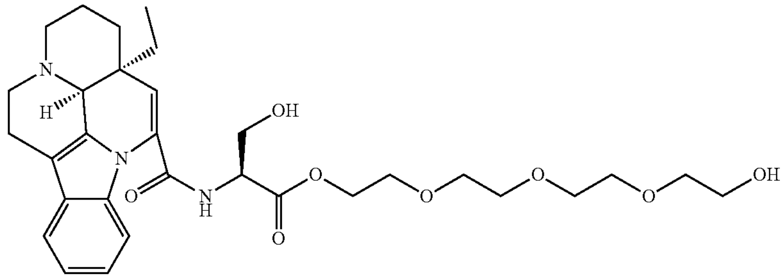

$^1$H NMR (500 MHz, DMSO-$d_6$) δ 9.05 (d, J=9.3 Hz, 1H), 7.57-7.51 (m, 2H), 7.44 (ddd, J=8.0, 7.0, 1.3 Hz, 1H), 7.27 (ddd, J=8.1, 7.0, 1.3 Hz, 1H), 6.82 (s, 1H), 4.55-4.47 (m, 2H), 4.46 (dd, J=12.3, 6.1 Hz, 1H), 4.28 (dt, J=12.4, 6.2 Hz, 1H), 3.96-3.87 (m, 1H), 3.89-3.50 (m, 18H), 3.05-2.96 (m, 1H), 2.96-2.83 (m, 3H), 2.86-2.73 (m, 1H), 2.50-2.41 (m, 1H), 1.75-1.54 (m, 5H), 1.42 (dq, J=12.8, 7.2 Hz, 1H), 0.88 (t, J=7.1 Hz, 3H). MS (ESI, m/z): 586 ($M^+$+1).

Example 35: Synthesis of Compound S35

In Example 35, the compound 1-1 in Example 1 was replaced with a corresponding raw material 1-35, and a specific structural formula was

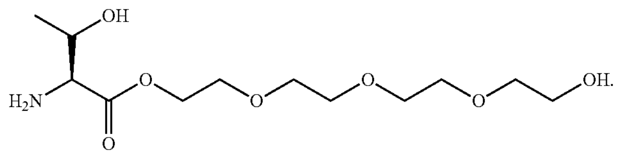

S35

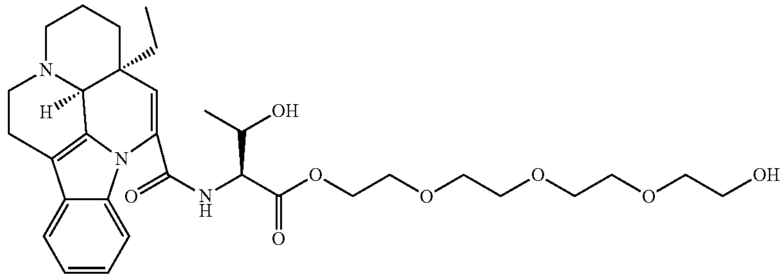

$^1$H NMR (500 MHZ, DMSO-$d_6$) δ 8.81 (d, J=9.1 Hz, 1H), 7.55 (td, J=8.1, 1.3 Hz, 2H), 7.43 (ddd, J=8.0, 6.9, 1.3 Hz, 1H), 7.26 (ddd, J=8.1, 7.0, 1.3 Hz, 1H), 6.82 (s, 1H), 4.46 (h, J=6.5 Hz, 1H), 4.31 (dd, J=9.0, 7.0 Hz, 1H), 4.16 (td, J=6.3, 1.6 Hz, 2H), 4.09 (s, 1H), 3.99 (d, J=6.3 Hz, 1H), 3.83-3.74 (m, 1H), 3.77-3.69 (m, 1H), 3.72-3.64 (m, 7H), 3.68-3.57 (m, 3H), 3.55 (dq, J=12.3, 6.2 Hz, 2H), 3.53-3.44 (m, 1H), 3.13 (ddd, J=12.1, 6.4, 4.2 Hz, 1H), 3.01 (ddd, J=12.1, 6.4, 4.2 Hz, 1H), 2.90 (ddd, J=15.4, 6.5, 4.2 Hz, 1H), 2.86-2.74 (m, 2H), 2.60 (ddd, J=12.0, 7.0, 4.8 Hz, 1H), 1.73-1.43 (m, 6H), 1.13 (d, J=6.6 Hz, 3H), 0.84 (t, J=7.2 Hz, 3H). MS (ESI, m/z): 600 ($M^+$+1).

Example 36: Synthesis of Compound S36

In Example 36, the compound 1-1 in Example 1 was replaced with a corresponding raw material 1-36, and a specific structural formula was

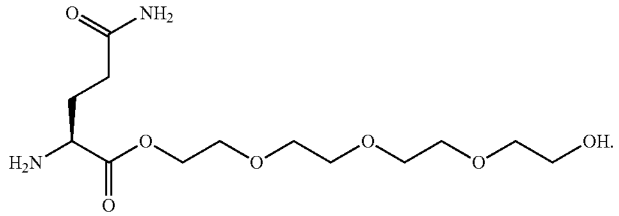

S36

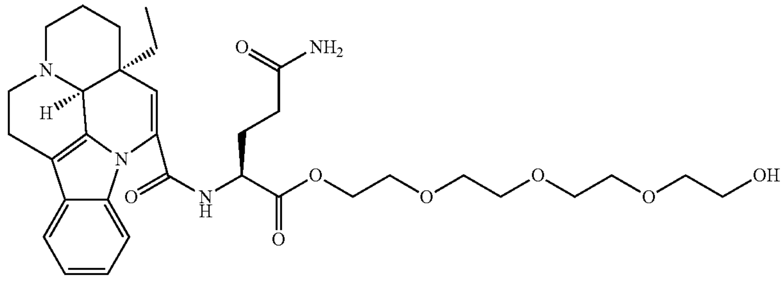

$^1$H NMR (500 MHZ, DMSO-$d_6$) δ 8.53 (d, J=9.3 Hz, 1H), 7.59-7.47 (m, 3H), 7.27 (ddd, J=8.1, 5.9, 2.5 Hz, 1H), 6.92 (s, 2H), 6.84 (s, 1H), 4.38-4.24 (m, 2H), 4.16 (dt, J=9.3, 6.0 Hz, 1H), 4.03 (s, 1H), 3.83-3.71 (m, 1H), 3.74-3.66 (m, 6H), 3.69-3.58 (m, 5H), 3.61-3.50 (m, 3H), 3.14 (ddd, J=12.1, 6.4, 4.2 Hz, 1H), 3.02 (ddd, J=12.3, 6.5, 4.3 Hz, 1H), 2.95 (ddd, J=15.4, 6.6, 4.2 Hz, 1H), 2.87-2.74 (m, 2H), 2.66-2.57 (m, 1H), 2.34 (dt, J=15.7, 7.8 Hz, 1H), 2.26 (dt, J=15.9, 8.0 Hz, 1H), 1.97-1.80 (m, 2H), 1.77-1.64 (m, 3H), 1.64-1.53 (m, 1H), 1.54-1.41 (m, 2H), 0.88 (t, J=7.2 Hz, 3H). MS (ESI, m/z): 627 ($M^+$+1).

Example 37: Synthesis of Compound S37

In Example 37, the compound 1-1 in Example 1 was replaced with a corresponding raw material 1-37, and a specific structural formula was

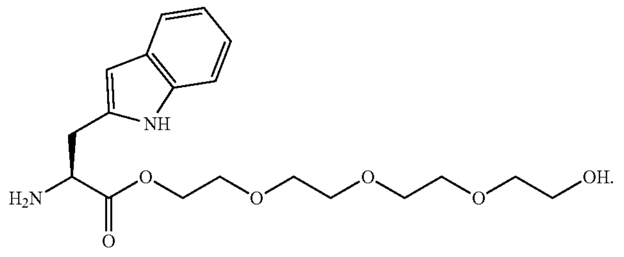
S37
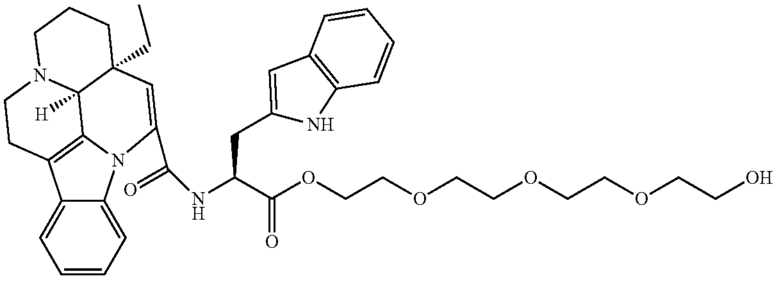
$^1H$ NMR (500 MHZ, DMSO-$d_6$) δ 9.44 (d, J=9.3 Hz, 1H), 9.07 (s, 1H), 7.68-7.62 (m, 1H), 7.52 (dd, J=7.8, 1.3 Hz, 1H), 7.42 (ddd, J=8.0, 7.0, 1.3 Hz, 1H), 7.36-7.28 (m, 1H), 7.28-7.20 (m, 2H), 7.16-7.07 (m, 2H), 6.84 (d, J=1.8 Hz, 1H), 6.78 (s, 1H), 4.67 (dt, J=9.3, 7.8 Hz, 1H), 4.56 (s, 1H), 4.48 (dt, J=12.4, 6.2 Hz, 1H), 4.28 (dt, J=12.2, 6.2 Hz, 1H), 3.83-3.73 (m, 1H), 3.76-3.69 (m, 1H), 3.72-3.62 (m, 7H), 3.65-3.57 (m, 3H), 3.59-3.50 (m, 2H), 3.46-3.37 (m, 1H), 3.17-3.07 (m, 2H), 3.04-2.93 (m, 2H), 2.90-2.75 (m, 3H), 2.54-2.45 (m, 1H), 1.76-1.67 (m, 1H), 1.67 (ddd, J=9.1, 4.6, 2.0 Hz, 2H), 1.67-1.57 (m, 2H), 1.60-1.52 (m, 1H), 1.44 (dq, J=13.0, 7.2 Hz, 1H), 0.87 (t, J=7.2 Hz, 3H). MS (ESI, m/z): 685 ($M^+$+1).
Example 38: Synthesis of Compound S38
In Example 38, the compound 1-1 in Example 1 was replaced with a corresponding raw material 1-38, and a specific structural formula was
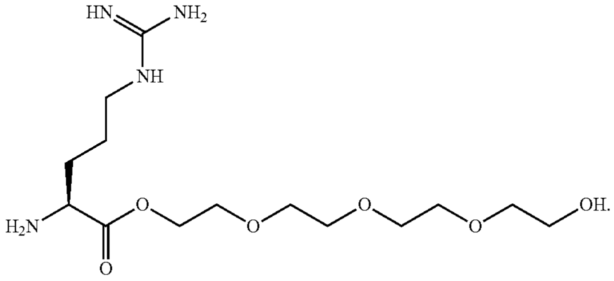
S38
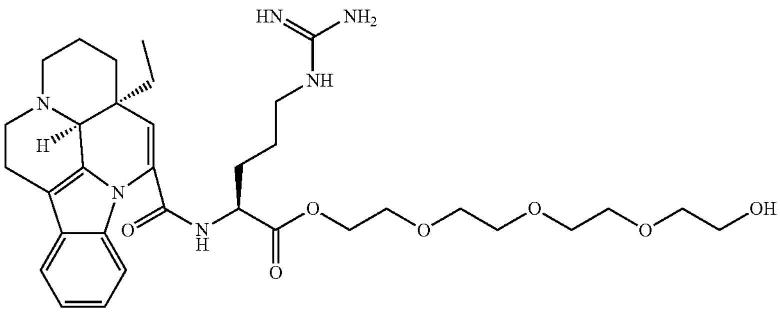

$^1$H NMR (500 MHZ, DMSO-$d_6$) δ 8.70 (d, J=9.1 Hz, 1H), 7.68 (dd, J=8.0, 1.3 Hz, 1H), 7.53 (dd, J=7.9, 1.3 Hz, 1H), 7.42 (ddd, J=8.0, 6.9, 1.3 Hz, 1H), 7.31-7.21 (m, 2H), 6.82 (s, 1H), 5.97 (t, J=4.4 Hz, 1H), 5.69 (d, J=6.8 Hz, 1H), 5.45 (d, J=6.8 Hz, 1H), 4.50 (dt, J=12.3, 6.2 Hz, 1H), 4.43 (dt, J=9.3, 6.0 Hz, 1H), 4.33-4.24 (m, 2H), 3.78 (ddt, J=12.3, 7.7, 6.6 Hz, 1H), 3.75-3.66 (m, 6H), 3.69-3.57 (m, 5H), 3.60-3.48 (m, 3H), 3.45 (dtd, J=14.3, 5.7, 4.3 Hz, 1H), 3.33 (dtd, J=14.3, 5.8, 4.3 Hz, 1H), 3.09 (ddd, J=11.9, 6.4, 4.3 Hz, 1H), 2.99-2.90 (m, 2H), 2.87 (ddd, J=12.1, 6.6, 4.4 Hz, 1H), 2.80 (ddd, J=15.2, 6.4, 4.3 Hz, 1H), 2.47 (ddd, J=11.9, 7.1, 4.7 Hz, 1H), 2.16-1.99 (m, 2H), 1.81-1.63 (m, 2H), 1.63-1.43 (m, 4H), 0.88 (t, J=7.2 Hz, 3H). MS (ESI, m/z): 641 ($M^+$+1).

Example 39: Synthesis of Compound S39

In Example 39, the compound 1-1 in Example 1 was replaced with a corresponding raw material 1-39, and a specific structural formula was

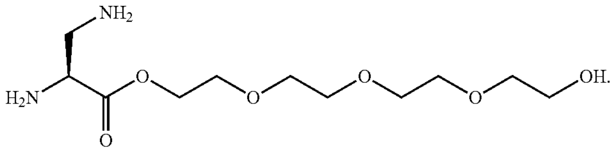

S39

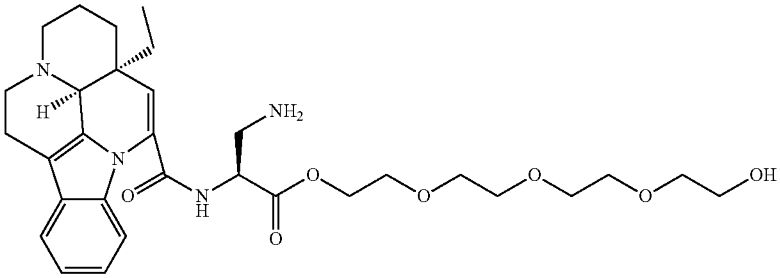

$^1$H NMR (500 MHZ, DMSO-$d_6$) δ 8.74 (d, J=9.3 Hz, 1H), 7.56-7.49 (m, 2H), 7.46 (ddd, J=7.9, 6.8, 1.3 Hz, 1H), 7.27 (ddd, J=8.1, 6.9, 1.4 Hz, 1H), 6.82 (s, 1H), 4.52-4.40 (m, 2H), 4.25 (dt, J=12.4, 6.2 Hz, 1H), 4.02 (s, 1H), 3.85-3.69 (m, 3H), 3.72-3.66 (m, 2H), 3.67 (ddd, J=7.0, 3.1, 1.3 Hz, 6H), 3.67-3.57 (m, 3H), 3.61-3.48 (m, 2H), 3.48-3.39 (m, 1H), 3.18-3.08 (m, 2H), 3.01 (ddd, J=12.3, 6.6, 4.2 Hz, 1H), 2.96-2.88 (m, 1H), 2.91-2.84 (m, 1H), 2.80-2.70 (m, 3H), 2.58 (ddd, J=11.8, 6.8, 4.7 Hz, 1H), 1.77-1.59 (m, 4H), 1.59-1.39 (m, 2H), 0.88 (t, J=7.2 Hz, 3H). MS (ESI, m/z): 585 ($M^+$+1).

Example 40: Synthesis of Compound S40

In Example 40, the compound 1-1 in Example 1 was replaced with a corresponding raw material 1-40, and a specific structural formula was

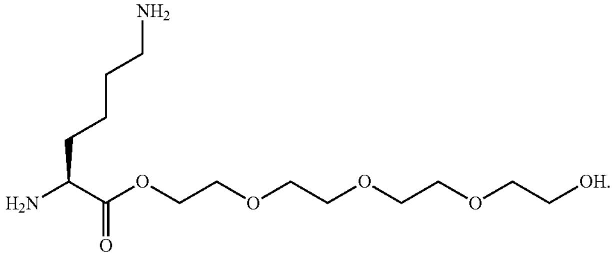

-continued

S40

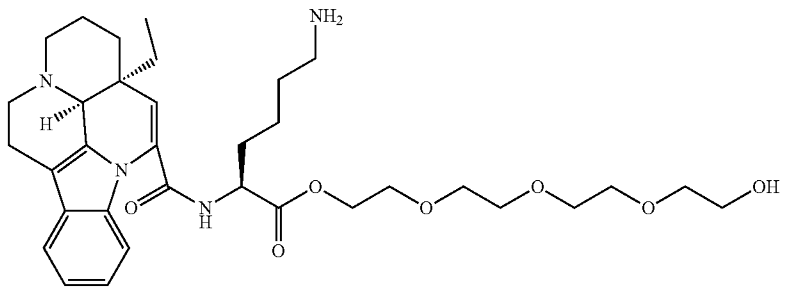

$^1H$ NMR (500 MHZ, DMSO-$d_6$) δ 8.70 (d, J=9.3 Hz, 1H), 7.60-7.48 (m, 3H), 7.27 (ddd, J=8.1, 6.9, 1.4 Hz, 1H), 6.82 (s, 1H), 4.55-4.44 (m, 2H), 4.32-4.22 (m, 2H), 3.83-3.44 (m, 15H), 3.06 (ddd, J=12.1, 6.4, 4.2 Hz, 1H), 2.93 (ddd, J=15.6, 6.4, 4.2 Hz, 1H), 2.86-2.64 (m, 4H), 2.57-2.40 (m, 2H), 1.80-1.70 (m, 1H), 1.74-1.63 (m, 2H), 1.66-1.55 (m, 3H), 1.53 (t, J=6.1 Hz, 2H), 1.48-1.22 (m, 5H), 1.10 (dp, J=13.2, 6.6 Hz, 1H), 0.87 (t, J=7.2 Hz, 3H). MS (ESI, m/z): 627 ($M^+$+1).

Example 41: Synthesis of Compound S41

In Example 41, the compound 1-1 in Example 1 was replaced with a corresponding raw material 1-41, and a specific structural formula was

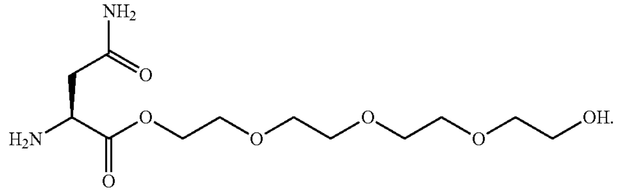

S41

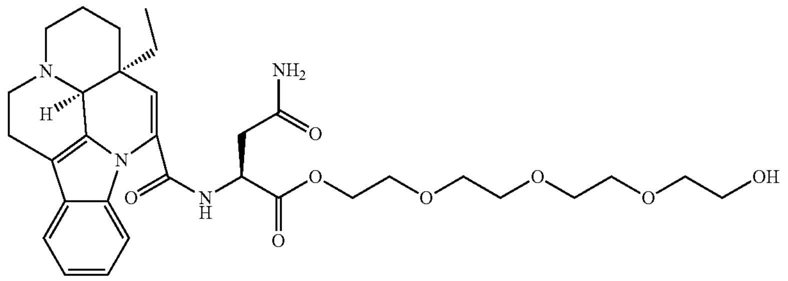

$^1H$ NMR (500 MHZ, DMSO-$d_6$) δ 9.11 (d, J=9.1 Hz, 1H), 7.63 (dd, J=7.8, 1.4 Hz, 1H), 7.60-7.49 (m, 2H), 7.27 (ddd, J=8.1, 7.0, 1.3 Hz, 1H), 7.05 (s, 2H), 6.78 (s, 1H), 4.60 (dt, J=9.3, 7.3 Hz, 1H), 4.53 (s, 1H), 4.28 (ddt, J=24.5, 12.3, 6.2 Hz, 2H), 3.83-3.45 (m, 14H), 3.10 (ddd, J=11.9, 6.5, 4.2 Hz, 1H), 3.02 (ddd, J=15.4, 6.5, 4.2 Hz, 1H), 2.89-2.66 (m, 5H), 2.46 (ddd, J=11.8, 6.8, 4.6 Hz, 1H), 1.75-1.67 (m, 1H), 1.71-1.62 (m, 2H), 1.66-1.41 (m, 4H), 0.85 (t, J=7.2 Hz, 3H). MS (ESI, m/z): 613 ($M^+$+1).

Example 42: Synthesis of Compound S42

In Example 42, the compound 1-1 in Example 1 was replaced with a corresponding raw material 1-42, and a specific structural formula was

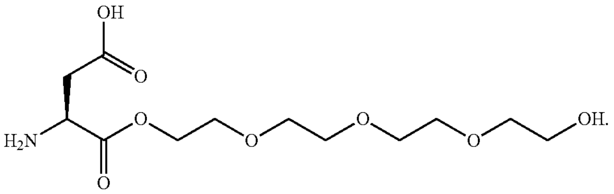

S42

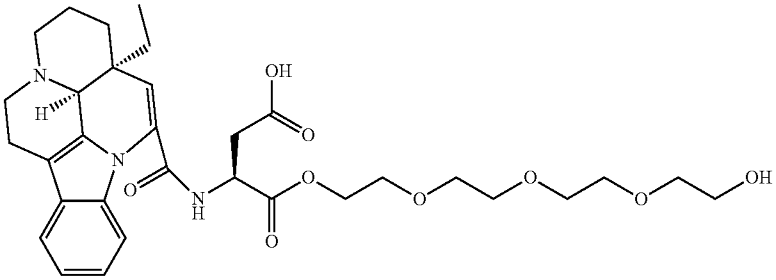

$^1$H NMR (500 MHZ, DMSO-$d_6$) δ 9.33 (d, J=9.3 Hz, 1H), 7.53 (dd, J=8.0, 1.3 Hz, 1H), 7.45 (ddd, J=8.1, 6.9, 1.3 Hz, 1H), 7.40 (dd, J=7.8, 1.5 Hz, 1H), 7.27 (ddd, J=8.1, 6.9, 1.5 Hz, 1H), 6.78 (s, 1H), 4.80-4.72 (m, 2H), 4.32 (dt, J=12.4, 6.1 Hz, 1H), 4.30-4.21 (m, 2H), 3.86 (dt, J=12.3, 6.6 Hz, 1H), 3.83-3.72 (m, 1H), 3.76-3.62 (m, 9H), 3.66-3.58 (m, 1H), 3.52 (h, J=6.1 Hz, 2H), 3.40 (dt, J=12.3, 6.5 Hz, 1H), 3.14-3.06 (m, 1H), 3.01-2.86 (m, 3H), 2.87-2.75 (m, 2H), 2.74 (dd, J=16.3, 7.3 Hz, 1H), 2.62-2.53 (m, 1H), 1.77-1.46 (m, 7H), 0.85 (t, J=7.2 Hz, 3H). MS (ESI, m/z): 614 ($M^+$+1).

Example 43: Synthesis of Compound S43

In Example 43, the compound 1-1 in Example 1 was replaced with a corresponding raw material 1-43, and a specific structural formula was

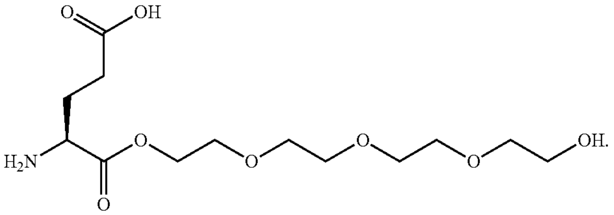

S43

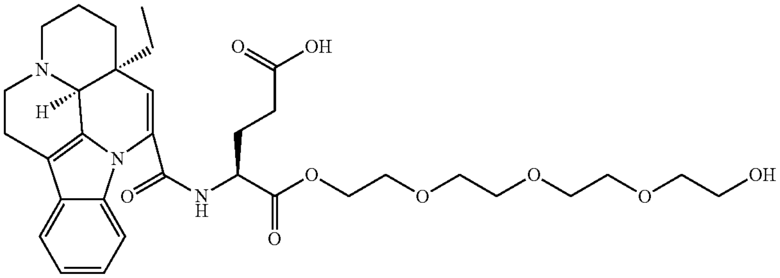

$^1$H NMR (500 MHz, DMSO-$d_6$) δ 8.53 (d, J=9.3 Hz, 1H), 7.52 (dt, J=7.9, 0.9 Hz, 1H), 7.49-7.42 (m, 2H), 7.27 (ddd, J=8.1, 4.9, 3.3 Hz, 1H), 6.84 (s, 1H), 4.53 (s, 1H), 4.48-4.38 (m, 2H), 4.36-4.22 (m, 2H), 3.83-3.75 (m, 1H), 3.79-3.73 (m, 1H), 3.77-3.66 (m, 3H), 3.70-3.59 (m, 6H), 3.63-3.55 (m, 1H), 3.54-3.44 (m, 2H), 3.06 (ddd, J=11.9, 6.5, 4.2 Hz, 1H), 2.95-2.83 (m, 2H), 2.80 (ddd, J=15.6, 6.4, 4.2 Hz, 1H), 2.70 (ddd, J=12.1, 6.4, 4.2 Hz, 1H), 2.39-2.17 (m, 4H), 2.11 (dtd, J=12.8, 8.1, 5.9 Hz, 1H), 1.77-1.63 (m, 3H), 1.57 (dtt, J=13.2, 7.0, 4.8 Hz, 1H), 1.49 (ddd, J=12.1, 7.4, 4.9 Hz, 1H), 1.41 (dq, J=12.8, 7.2 Hz, 1H), 0.85 (t, J=7.2 Hz, 3H). MS (ESI, m/z): 628 ($M^+$+1).

Example 44: Synthesis of Compound S44

In Example 44, the compound 1-44 in Example 1 was replaced with a corresponding raw material 1-44, and a specific structural formula was

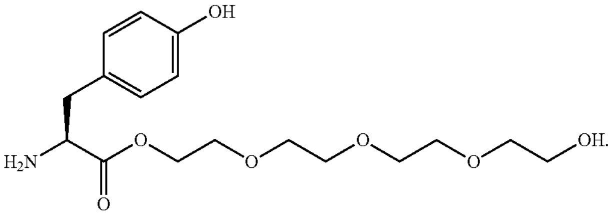

S44

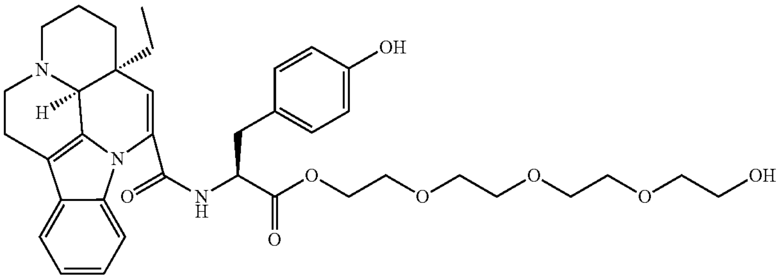

$^1$H NMR (500 MHZ, DMSO-$d_6$) δ 8.63 (d, J=9.3 Hz, 1H), 7.70 (s, 1H), 7.58 (ddd, J=14.4, 7.9, 1.3 Hz, 2H), 7.50 (ddd, J=8.0, 6.9, 1.3 Hz, 1H), 7.25 (ddd, J=8.0, 6.9, 1.3 Hz, 1H), 6.98 (dt, J=8.7, 1.0 Hz, 2H), 6.82 (s, 1H), 6.70-6.64 (m, 2H), 4.75 (dt, J=9.3, 7.7 Hz, 1H), 4.56 (s, 1H), 4.30 (td, J=6.1, 1.6 Hz, 2H), 3.83-3.73 (m, 1H), 3.76-3.70 (m, 1H), 3.73-3.63 (m, 8H), 3.67-3.47 (m, 5H), 3.14-3.05 (m, 2H), 3.03 (ddt, J=13.9, 7.7, 1.1 Hz, 1H), 2.93 (ddd, J=15.6, 6.4, 4.3 Hz, 1H), 2.89-2.78 (m, 2H), 2.72 (ddd, J=11.9, 6.4, 4.3 Hz, 1H), 2.41-2.33 (m, 1H), 1.74-1.48 (m, 6H), 0.87 (t, J=7.2 Hz, 3H). MS (ESI, m/z): 662 ($M^+$+1).

Example 45: Synthesis of Compound S45

In Example 45, the compound 1-1 in Example 1 was replaced with a corresponding raw material 1-45, and a specific structural formula was

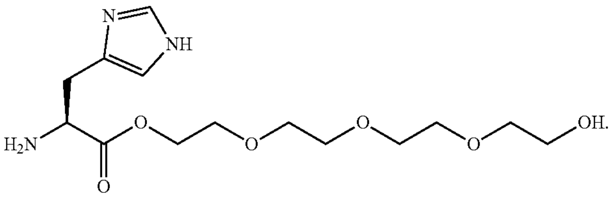

S45

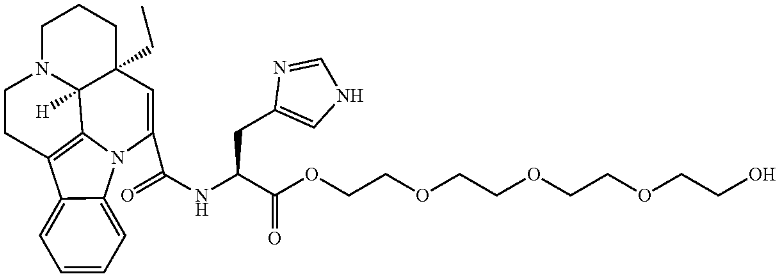

$^1$H NMR (500 MHZ, DMSO-$d_6$) δ 8.70 (d, J=9.3 Hz, 1H), 8.35 (dd, J=2.0, 1.1 Hz, 1H), 7.67 (dd, J=7.6, 1.4 Hz, 1H), 7.59 (dd, J=7.7, 1.2 Hz, 1H), 7.50 (ddd, J=8.0, 6.9, 1.3 Hz, 1H), 7.32 (t, J=2.0 Hz, 1H), 7.25 (ddd, J=8.1, 7.0, 1.3 Hz, 1H), 6.83 (s, 1H), 4.73 (dt, J=9.3, 7.8 Hz, 1H), 4.55-4.44 (m, 2H), 4.28 (dt, J=12.4, 6.2 Hz, 1H), 3.83-3.43 (m, 15H), 3.22-3.13 (m, 1H), 3.07 (ddd, J=11.9, 6.5, 4.2 Hz, 1H), 3.03-2.92 (m, 2H), 2.85 (ddd, J=15.6, 6.4, 4.2 Hz, 1H), 2.83-2.73 (m, 2H), 2.52-2.43 (m, 1H), 1.75-1.51 (m, 6H), 1.43 (dq, J=12.8, 7.2 Hz, 1H), 0.87 (t, J=7.1 Hz, 3H). MS (ESI, m/z): 636 ($M^+$+1).

Example 46: Synthesis of Compound S46

In Example 46, the compound 1-1 in Example 1 was replaced with a corresponding raw material 1-46, and a specific structural formula was

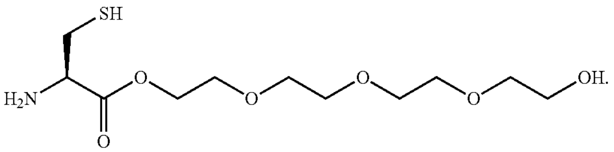

S46

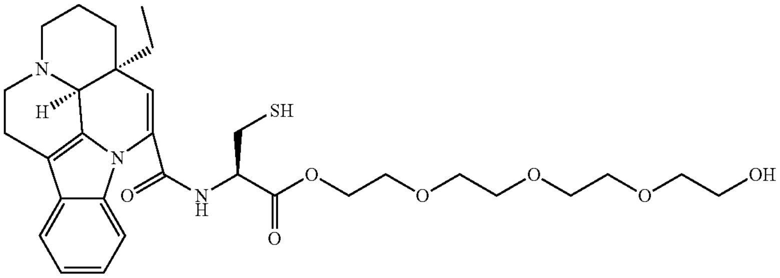

$^1$H NMR (500 MHZ, DMSO-$d_6$) δ 8.93 (d, J=9.3 Hz, 1H), 7.54 (ddd, J=7.6, 4.2, 1.2 Hz, 2H), 7.46 (ddd, J=7.9, 7.0, 1.2 Hz, 1H), 7.26 (ddd, J=8.1, 6.9, 1.3 Hz, 1H), 6.82 (s, 1H), 4.60-4.51 (m, 2H), 4.45 (dt, J=12.2, 6.1 Hz, 1H), 4.26 (dt, J=12.2, 6.1 Hz, 1H), 3.78 (ddt, J=12.8, 7.5, 6.5 Hz, 1H), 3.75-3.44 (m, 14H), 3.12-3.01 (m, 2H), 2.98-2.87 (m, 2H), 2.87-2.74 (m, 3H), 2.54-2.45 (m, 1H), 1.86-1.80 (m, 1H), 1.74-1.53 (m, 5H), 1.44 (dq, J=13.0, 7.2 Hz, 1H), 0.86 (t, J=7.2 Hz). MS (ESI, m/z): 602 ($M^+$+1).

Example 47: Synthesis of Compound S47

In Example 47, the compound 1-1 in Example 1 was replaced with a corresponding raw material 1-47, and a specific structural formula was

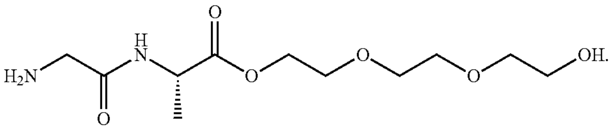

S47

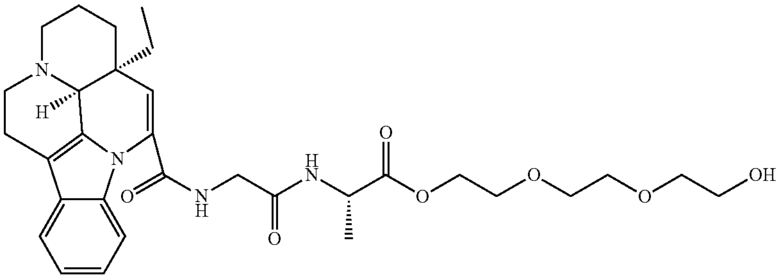

$^1$H NMR (500 MHZ, DMSO-$d_6$) δ 8.86 (t, J=5.8 Hz, 1H), 7.88 (d, J=9.3 Hz, 1H), 7.56 (ddd, J=20.3, 7.8, 1.3 Hz, 2H), 7.46 (ddd, J=8.0, 7.0, 1.3 Hz, 1H), 7.27 (ddd, J=8.0, 7.0, 1.3 Hz, 1H), 6.82 (s, 1H), 4.53 (s, 1H), 4.47-4.38 (m, 1H), 4.35 (t, J=6.2 Hz, 2H), 3.96 (dd, J=17.5, 5.8 Hz, 1H), 3.90-3.44 (m, 13H), 3.05 (ddd, J=11.9, 6.5, 4.2 Hz, 1H), 2.92 (ddd, J=15.6, 6.4, 4.2 Hz, 1H), 2.86-2.70 (m, 3H), 2.49-2.40 (m, 1H), 1.77-1.51 (m, 5H), 1.42 (dq, J=13.0, 7.2 Hz, 1H), 1.32 (d, J=6.8 Hz, 3H), 0.89 (t, J=7.1 Hz, 3H). MS (ESI, m/z): 660583 ($M^+$+1).

Example 48: Synthesis of Compound S48

In Example 48, the compound 1-1 in Example 1 was replaced with a corresponding raw material 1-48, and a specific structural formula was

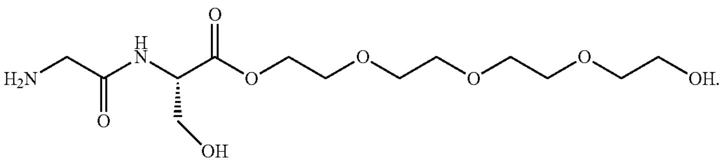

S48

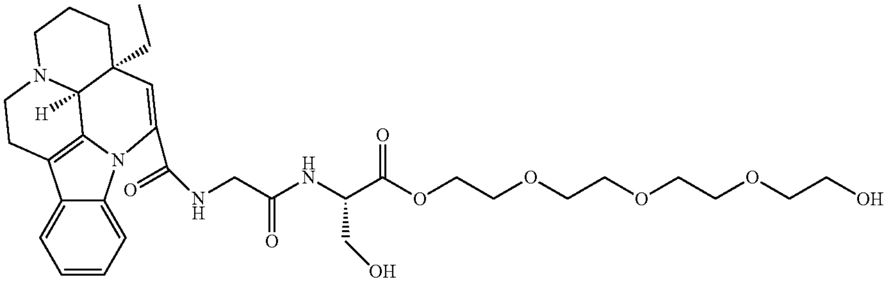

$^1$H NMR (500 MHZ, DMSO-$d_6$) δ 8.81 (t, J=5.8 Hz, 1H), 8.14 (d, J=9.3 Hz, 1H), 7.52 (ddd, J=10.7, 8.1, 1.4 Hz, 2H), 7.42 (ddd, J=7.8, 7.0, 1.3 Hz, 1H), 7.25 (ddd, J=8.0, 6.9, 1.3 Hz, 1H), 6.82 (s, 1H), 4.53 (dt, J=12.4, 6.2 Hz, 1H), 4.33-4.22 (m, 2H), 4.10-3.98 (m, 3H), 3.96-3.85 (m, 3H), 3.85-3.46 (m, 15H), 3.13 (ddd, J=12.1, 6.4, 4.2 Hz, 1H), 3.01 (ddd, J=12.1, 6.6, 4.2 Hz, 1H), 2.92 (ddd, J=15.4, 6.4, 4.1 Hz, 1H), 2.85-2.73 (m, 2H), 2.55 (ddd, J=11.7, 6.9, 4.7 Hz, 1H), 1.77-1.63 (m, 3H), 1.54 (dtt, J=12.8, 7.4, 4.8 Hz, 1H), 1.48-1.37 (m, 2H), 0.87 (t, J=7.2 Hz, 3H). MS (ESI, m/z): 643 ($M^+$+1).

Example 49: Synthesis of Compound S49

In Example 49, the compound 1-1 in Example 1 was replaced with a corresponding raw material 1-49, and a specific structural formula was

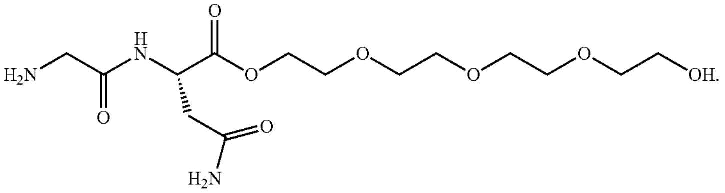

S49

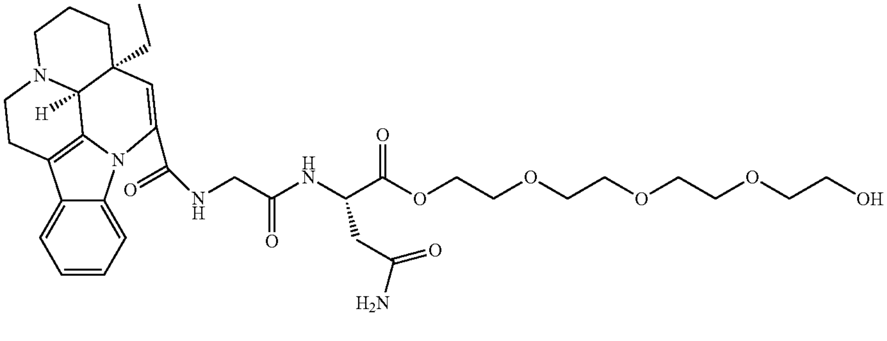

$^1$H NMR (500 MHZ, DMSO-$d_6$) δ 8.84 (t, J=5.8 Hz, 1H), 8.12 (d, J=9.3 Hz, 1H), 7.52 (ddd, J=24.2, 7.9, 1.3 Hz, 2H), 7.42 (ddd, J=8.0, 6.9, 1.3 Hz, 1H), 7.25 (ddd, J=8.0, 6.9, 1.4 Hz, 1H), 7.07 (s, 2H), 6.82 (s, 1H), 4.67 (dt, J=9.2, 7.3 Hz, 1H), 4.36-4.23 (m, 2H), 4.06-3.98 (m, 2H), 3.86-3.71 (m, 2H), 3.74-3.62 (m, 9H), 3.66-3.58 (m, 1H), 3.55 (ddt, J=13.0, 9.0, 6.4 Hz, 2H), 3.46 (dq, J=12.2, 6.1 Hz, 2H), 3.14 (ddd, J=12.1, 6.4, 4.2 Hz, 1H), 3.02 (ddd, J=12.1, 6.6, 4.2 Hz, 1H), 2.94-2.72 (m, 4H), 2.62-2.53 (m, 2H), 1.77-1.55 (m, 4H), 1.50-1.39 (m, 2H), 0.88 (t, J=7.2 Hz, 3H). MS (ESI, m/z): 670 ($M^+$+1).

Example 50: Synthesis of Compound S50

In Example 50, the compound 1-1 in Example 1 was replaced with a corresponding raw material 1-50, and a specific structural formula was

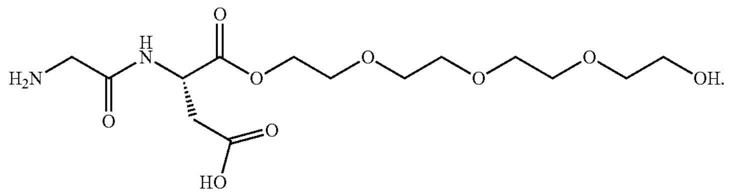

S50

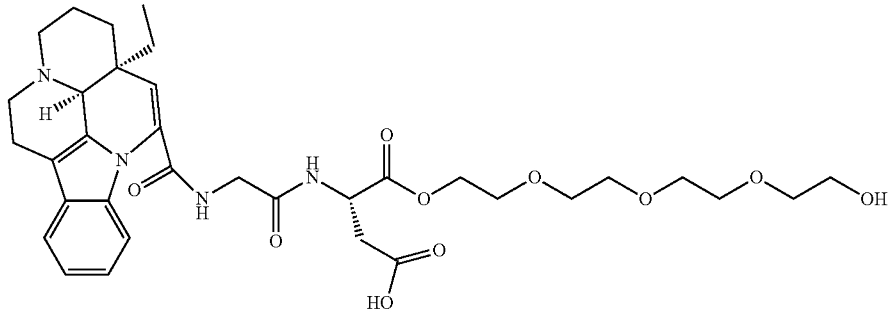

$^1$H NMR (500 MHZ, DMSO-$d_6$) δ 8.70 (t, J=5.8 Hz, 1H), 8.20 (d, J=9.3 Hz, 1H), 7.53 (ddd, J=10.7, 7.7, 1.2 Hz, 2H), 7.42 (ddd, J=8.0, 6.9, 1.2 Hz, 1H), 7.25 (ddd, J=8.0, 6.9, 1.3 Hz, 1H), 6.82 (s, 1H), 4.72 (dt, J=9.3, 7.5 Hz, 1H), 4.56 (s, 1H), 4.48 (dt, J=12.4, 6.2 Hz, 1H), 4.30 (dt, J=12.4, 6.2 Hz, 1H), 4.00 (dd, J=17.5, 5.8 Hz, 1H), 3.87 (dd, J=17.5, 5.8 Hz, 1H), 3.83-3.56 (m, 14H), 3.51 (dt, J=12.3, 6.1 Hz, 1H), 3.43 (dt, J=12.0, 6.6 Hz, 1H), 3.03 (ddd, J=11.9, 6.4, 4.3 Hz, 1H), 2.92 (ddd, J=15.0, 6.6, 4.3 Hz, 1H), 2.88-2.78 (m, 3H), 2.81-2.75 (m, 1H), 2.70 (dd, J=16.4, 7.4 Hz, 1H), 2.49-2.39 (m, 1H), 1.78-1.63 (m, 3H), 1.60-1.43 (m, 3H), 0.85 (t, J=7.2 Hz, 3H). MS (ESI, m/z): 671 ($M^+$+1).

Example 51: Synthesis of Compound S51

In Example 51, the compound 1-1 in Example 1 was replaced with a corresponding raw material 1-51, and a specific structural formula was

$^1$H NMR (500 MHZ, DMSO-$d_6$) δ 8.87 (t, J=5.8 Hz, 1H), 8.03 (d, J=9.3 Hz, 1H), 7.50 (dd, J=7.9, 1.3 Hz, 1H), 7.43 (ddd, J=8.1, 6.9, 1.3 Hz, 1H), 7.36 (dd, J=8.0, 1.3 Hz, 1H), 7.25 (ddd, J=8.1, 6.8, 1.3 Hz, 1H), 6.82 (s, 1H), 4.48 (dt, J=12.3, 6.1 Hz, 1H), 4.34-4.22 (m, 2H), 4.05 (s, 1H), 3.98 (dd, J=17.4, 5.9 Hz, 1H), 3.87 (dd, J=17.5, 5.8 Hz, 1H), 3.83-3.56 (m, 12H), 3.54 (dt, J=12.8, 6.4 Hz, 2H), 3.52-3.45 (m, 1H), 3.14 (ddd, J=12.1, 6.4, 4.2 Hz, 1H), 3.02 (ddd, J=12.1, 6.4, 4.2 Hz, 1H), 2.91 (ddd, J=15.4, 6.4, 4.1 Hz, 1H), 2.83 (ddd, J=11.9, 7.0, 4.7 Hz, 1H), 2.72 (ddd, J=15.4, 6.4, 4.2 Hz, 1H), 2.57 (ddd, J=11.8, 6.9, 4.7 Hz, 1H), 1.79-1.40 (m, 9H), 0.96-0.83 (m, 9H). MS (ESI, m/z): 669 ($M^+$+1).

Example 52: Synthesis of Compound S52

In Example 52, the compound 1-1 in Example 1 was replaced with a corresponding raw material 1-52, and a specific structural formula was

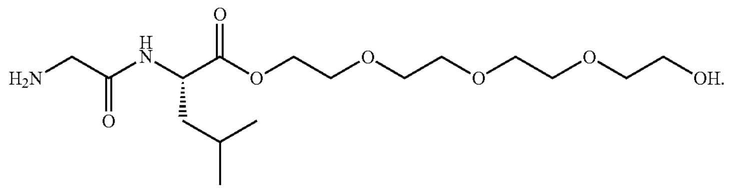

S51

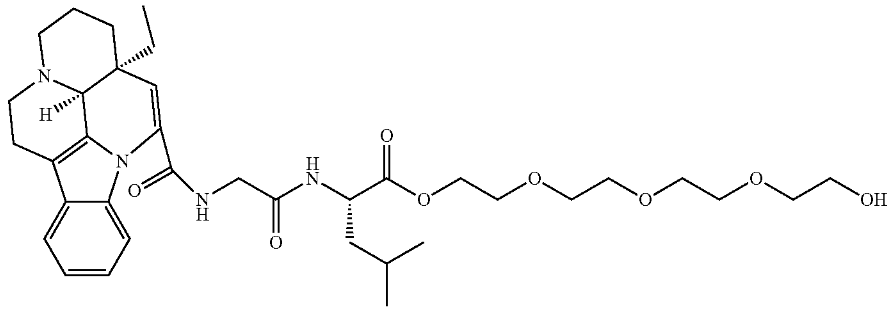

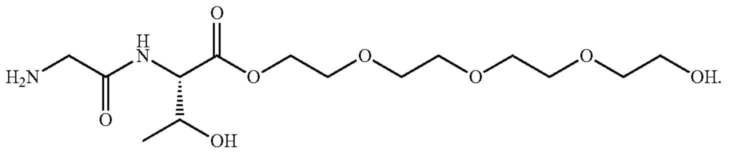

S52

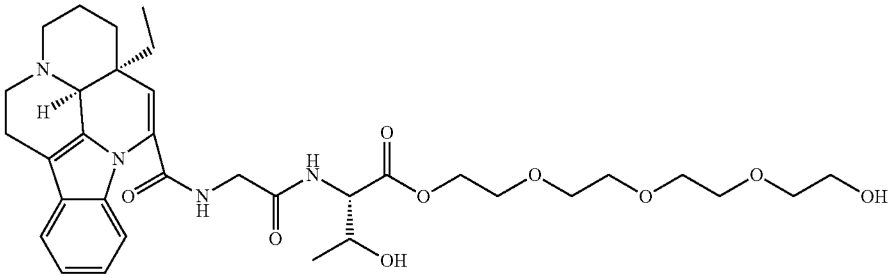

$^1$H NMR (500 MHZ, DMSO-$d_6$) δ 8.86 (t, J=5.8 Hz, 1H), 7.71 (d, J=9.1 Hz, 1H), 7.56 (ddd, J=19.0, 7.9, 1.4 Hz, 2H), 7.42 (ddd, J=8.0, 7.0, 1.3 Hz, 1H), 7.25 (ddd, J=8.0, 7.0, 1.3 Hz, 1H), 6.82 (s, 1H), 4.53 (s, 1H), 4.47-4.38 (m, 2H), 4.25-4.14 (m, 2H), 4.00-3.91 (m, 2H), 3.86 (dd, J=17.5, 5.8 Hz, 1H), 3.83-3.43 (m, 15H), 3.05 (ddd, J=12.1, 6.4, 4.3 Hz, 1H), 2.92 (ddd, J=15.4, 6.3, 4.2 Hz, 1H), 2.81 (ddd, J=15.6, 6.4, 4.2 Hz, 1H), 2.79-2.70 (m, 2H), 2.49-2.40 (m, 1H), 1.76-1.52 (m, 5H), 1.42 (dq, J=13.0, 7.2 Hz, 1H), 1.10 (d, J=6.6 Hz, 3H), 0.89 (t, J=7.2 Hz, 3H). MS (ESI, m/z): 657 ($M^+$+1).

Example 53: Synthesis of Compound S53

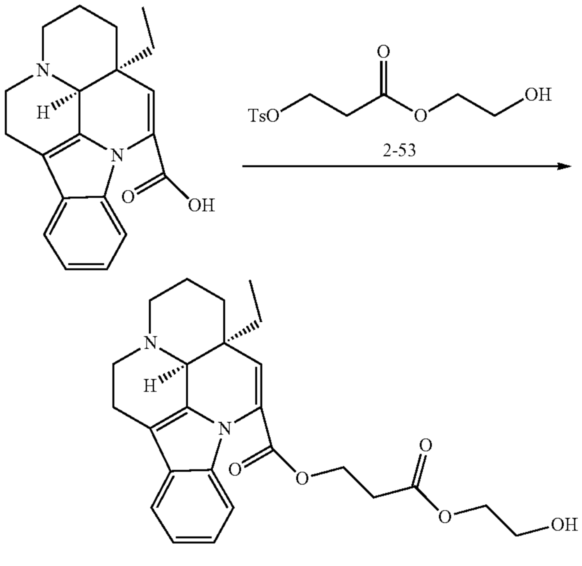

S53

Vinpocetine hydrolyzed product (200 mg, 0.62 mmol), and compound 2-53 (196 mg, 0.68 mmol) were dissolved in DMF (5 mL). Potassium carbonate (128 mg, 0.93 mmol) and potassium iodide (103 mg, 0.62 mmol) were added to the above solution, and then the temperature of the reaction was raised to 65° C. TLC monitored the reaction until the reaction was completed. Then, the reaction was stopped, and the reaction solution was cooled to room temperature. The solvent was evaporated, and then the reaction solution was added with water (10 mL) and extracted with (10 mL×3). The organic phases were combined, washed with saturated salt solution (10 mL), dried over anhydrous magnesium sulfate, filtered, concentrated, and subjected to column chromatography (elution dichloromethane:methanol=30:1) to obtain a compound S53 (163 mg, 60%).

$^1$H NMR (500 MHZ, DMSO-$d_6$) δ 7.58-7.52 (m, 1H), 7.44-7.36 (m, 2H), 7.32-7.23 (m, 1H), 6.89 (s, 1H), 4.66 (dt, J=11.5, 7.1 Hz, 1H), 4.59 (s, 1H), 4.47 (dt, J=11.4, 7.1 Hz, 1H), 4.29-4.15 (m, 2H), 3.89-3.74 (m, 2H), 3.24 (t, J=7.3 Hz, 1H), 3.06 (ddd, J=11.9, 6.5, 4.2 Hz, 1H), 2.93 (ddd, J=15.4, 6.3, 4.2 Hz, 1H), 2.86-2.54 (m, 6H), 2.51-2.43 (m, 1H), 1.76-1.52 (m, 5H), 1.42 (dq, J=12.8, 7.2 Hz, 1H), 0.88 (t, J=7.2 Hz, 3H). MS (ESI, m/z): 439 ($M^+$+1).

All the compounds S54-S62 in the following Examples 54-62 could be obtained according to the synthesis method of Example 53, and the reaction process and reaction conditions were the same as those in Example 53, and only the raw material 2-53 in Example 53 needed to be replaced with a corresponding raw material.

Example 54: Synthesis of Compound S54

In Example 54, the compound 2-53 in Example 53 was replaced with a corresponding raw material 2-54, and a specific structural formula was

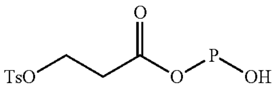 P = PEG-4000.

S54

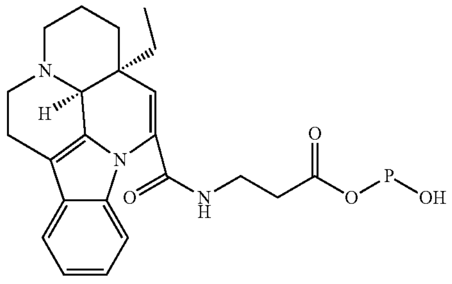 P = PEG-4000

$^1H$ NMR (500 MHZ, DMSO-$d_6$) δ 7.54 (ddd, J=13.4, 7.9, 1.4 Hz, 2H), 7.43-7.36 (m, 1H), 7.31-7.23 (m, 1H), 6.89 (s, 1H), 4.66 (dt, J=11.5, 7.1 Hz, 1H), 4.59 (s, 1H), 4.48 (dt, J=11.5, 7.1 Hz, 1H), 3.51-3.17 (—$OCH_2CH_2$), 3.24 (t, J=7.3 Hz, 1H), 3.06 (ddd, J=12.1, 6.4, 4.2 Hz, 1H), 2.94 (ddd, J=15.4, 6.4, 4.2 Hz, 1H), 2.86-2.71 (m, 3H), 2.69-2.52 (m, 2H), 2.47 (ddd, J=11.7, 6.8, 4.7 Hz, 1H), 1.75-1.51 (m, 6H), 1.42 (dq, J=13.0, 7.2 Hz, 1H), 0.88 (t, J=7.2 Hz, 3H).

Example 55: Synthesis of Compound S55

In Example 55, the compound 2-53 in Example 53 was replaced with a corresponding raw material 2-55, and a specific structural formula was

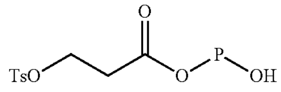

P = PEG-2000.

S55

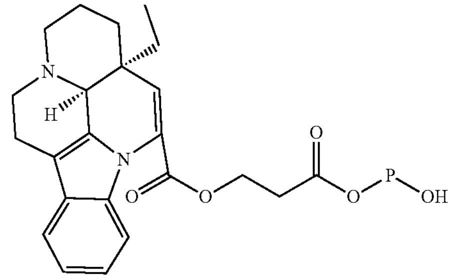

P = PEG-2000

$^1H$ NMR (500 MHZ, DMSO-$d_6$) δ 7.54 (ddd, J=13.4, 7.9, 1.4 Hz, 2H), 7.43-7.36 (m, 1H), 7.31-7.23 (m, 1H), 6.89 (s, 1H), 4.66 (dt, J=11.5, 7.1 Hz, 1H), 4.59 (s, 1H), 4.48 (dt, J=11.5, 7.1 Hz, 1H), 3.51-3.17 (—$OCH_2CH_2$), 3.24 (t, J=7.3 Hz, 1H), 3.06 (ddd, J=12.1, 6.4, 4.2 Hz, 1H), 2.94 (ddd, J=15.4, 6.4, 4.2 Hz, 1H), 2.86-2.71 (m, 3H), 2.69-2.52 (m, 2H), 2.47 (ddd, J=11.7, 6.8, 4.7 Hz, 1H), 1.75-1.51 (m, 6H), 1.42 (dq, J=13.0, 7.2 Hz, 1H), 0.88 (t, J=7.2 Hz, 3H).

Example 56: Synthesis of Compound S56

In Example 56, the compound 2-53 in Example 53 was replaced with a corresponding raw material 2-56, and a specific structural formula was

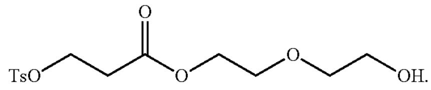

-continued

S56

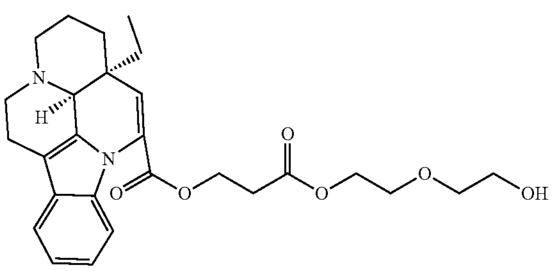

$^1H$ NMR (500 MHZ, DMSO-$d_6$) δ 7.55 (ddd, J=7.6, 5.0, 1.3 Hz, 2H), 7.48 (ddd, J=8.0, 7.0, 1.3 Hz, 1H), 7.27 (ddd, J=8.1, 6.9, 1.3 Hz, 1H), 6.89 (s, 1H), 4.69-4.50 (m, 3H), 4.36 (dt, J=12.3, 6.1 Hz, 1H), 4.05 (dt, J=12.4, 6.2 Hz, 1H), 3.84-3.74 (m, 1H), 3.78-3.71 (m, 2H), 3.73-3.64 (m, 1H), 3.67-3.52 (m, 2H), 3.47 (dt, J=12.3, 6.3 Hz, 1H), 3.06 (ddd, J=12.1, 6.4, 4.2 Hz, 1H), 2.93 (ddd, J=15.6, 6.4, 4.2 Hz, 1H), 2.83 (ddd, J=15.6, 6.4, 4.3 Hz, 1H), 2.81-2.72 (m, 2H), 2.69-2.54 (m, 2H), 2.51-2.43 (m, 1H), 1.75-1.52 (m, 5H), 1.39 (dq, J=13.0, 7.2 Hz, 1H), 0.87 (t, J=7.2 Hz, 3H). MS (ESI, m/z): 483 ($M^+$+1).

Example 57: Synthesis of Compound S57

In Example 57, the compound 2-53 in Example 53 was replaced with a corresponding raw material 2-57, and a specific structural formula was

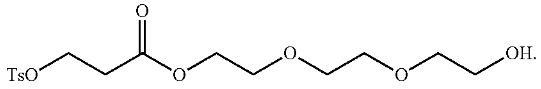

S57

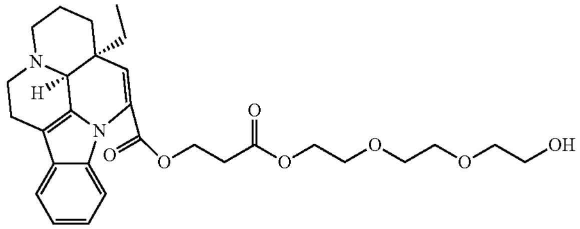

$^1H$ NMR (500 MHZ, DMSO-$d_6$) δ 7.55 (dd, J=7.9, 1.3 Hz, 1H), 7.52-7.43 (m, 2H), 7.27 (ddd, J=8.1, 6.7, 1.7 Hz, 1H), 6.90 (s, 1H), 4.70-4.61 (m, 2H), 4.46-4.31 (m, 2H), 4.13 (dt, J=12.2, 6.1 Hz, 1H), 3.84-3.56 (m, 11H), 3.44 (dt, J=12.1, 6.5 Hz, 1H), 3.06-2.97 (m, 1H), 2.98-2.89 (m, 1H), 2.87-2.72 (m, 4H), 2.56 (dt, J=16.1, 7.1 Hz, 1H), 2.46 (ddd, J=11.9, 6.8, 4.7 Hz, 1H), 1.75-1.51 (m, 6H), 1.46 (dq, J=12.8, 7.1 Hz, 1H), 0.88 (t, J=7.2 Hz, 3H). MS (ESI, m/z): 527 ($M^+$+1).

Example 58: Synthesis of Compound S58

In Example 58, the compound 2-53 in Example 53 was replaced with a corresponding raw material 2-58, and a specific structural formula was

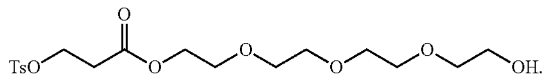

S58

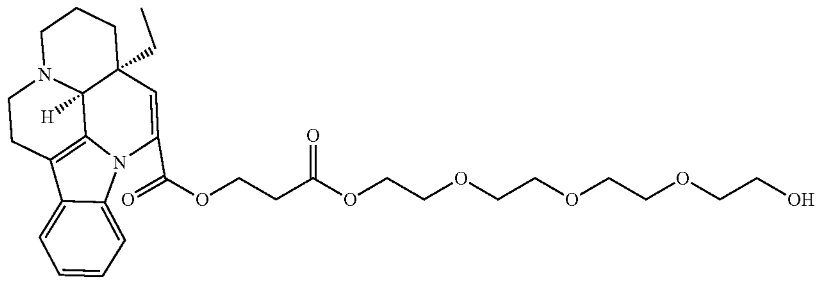

$^1$H NMR (500 MHZ, DMSO-$d_6$) δ 7.58-7.45 (m, 3H), 7.27 (ddd, J=8.0, 6.9, 1.4 Hz, 1H), 6.89 (s, 1H), 4.61 (dt, J=11.4, 7.1 Hz, 1H), 4.47 (dt, J=11.4, 7.1 Hz, 1H), 4.32 (dt, J=12.2, 6.1 Hz, 1H), 4.12-4.03 (m, 2H), 3.84-3.57 (m, 14H), 3.58-3.49 (m, 1H), 3.14 (ddd, J=12.1, 6.4, 4.2 Hz, 1H), 3.02 (ddd, J=12.1, 6.6, 4.2 Hz, 1H), 2.94 (ddd, J=15.4, 6.5, 4.2 Hz, 1H), 2.85-2.75 (m, 2H), 2.72-2.51 (m, 3H), 1.75-1.63 (m, 2H), 1.63-1.53 (m, 1H), 1.53 (tt, J=5.2, 1.5 Hz, 1H), 1.53-1.43 (m, 2H), 0.87 (t, J=7.2 Hz, 3H). MS (ESI, m/z): 571 ($M^+$+1).

Example 59: Synthesis of Compound S59

In Example 59, the compound 2-53 in Example 53 was replaced with a corresponding raw material 2-59, and a specific structural formula was

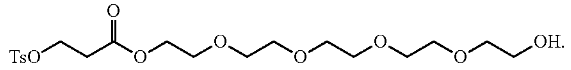

S59

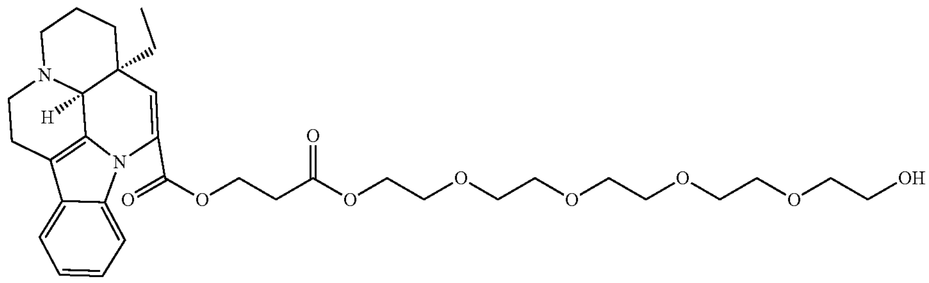

$^1$H NMR (500 MHZ, DMSO-$d_6$) δ 7.55 (ddd, J=9.1, 7.8, 1.4 Hz, 2H), 7.48 (ddd, J=8.0, 7.0, 1.3 Hz, 1H), 7.27 (ddd, J=8.1, 7.0, 1.3 Hz, 1H), 6.89 (s, 1H), 4.65 (dt, J=11.3, 7.1 Hz, 1H), 4.59-4.50 (m, 2H), 4.35 (dt, J=12.4, 6.2 Hz, 1H), 4.06 (dt, J=12.4, 6.2 Hz, 1H), 3.83-3.74 (m, 1H), 3.77-3.69 (m, 1H), 3.73-3.60 (m, 15H), 3.64-3.57 (m, 1H), 3.56 (dt, J=12.3, 6.5 Hz, 1H), 3.48 (dt, J=12.5, 6.3 Hz, 1H), 3.06 (ddd, J=11.9, 6.4, 4.2 Hz, 1H), 2.93 (ddd, J=15.4, 6.3, 4.2 Hz, 1H), 2.83 (ddd, J=15.4, 6.4, 4.3 Hz, 1H), 2.81-2.72 (m, 2H), 2.69-2.54 (m, 2H), 2.46 (ddd, J=11.8, 6.8, 4.7 Hz, 1H), 1.75-1.51 (m, 6H), 1.39 (dq, J=13.0, 7.3 Hz, 1H), 0.87 (t, J=7.2 Hz, 3H). MS (ESI, m/z): 615 ($M^+$+1).

Example 60: Synthesis of Compound S60

In Example 60, the compound 2-60 in Example 53 was replaced with a corresponding raw material 2-60, and a specific structural formula was

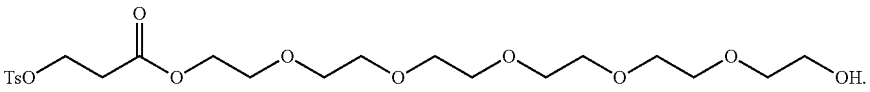

S60

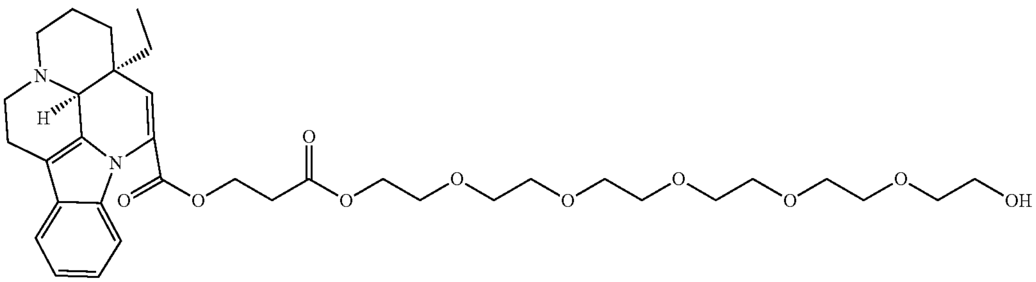

$^1$H NMR (500 MHZ, DMSO-$d_6$) δ 7.55 (td, J=7.8, 1.2 Hz, 2H), 7.40 (ddd, J=7.9, 7.0, 1.3 Hz, 1H), 7.26 (ddd, J=8.1, 7.1, 1.3 Hz, 1H), 6.89 (s, 1H), 4.65 (dt, J=11.5, 7.1 Hz, 1H), 4.59-4.50 (m, 2H), 4.35 (dt, J=12.3, 6.1 Hz, 1H), 4.06 (dt, J=12.4, 6.2 Hz, 1H), 3.83-3.73 (m, 1H), 3.76-3.69 (m, 1H), 3.73-3.63 (m, 17H), 3.67-3.61 (m, 1H), 3.65-3.58 (m, 1H), 3.62-3.52 (m, 1H), 3.55-3.43 (m, 1H), 3.06 (ddd, J=11.9, 6.4, 4.2 Hz, 1H), 2.93 (ddd, J=15.4, 6.3, 4.2 Hz, 1H), 2.87-2.77 (m, 1H), 2.81-2.72 (m, 2H), 2.69-2.54 (m, 2H), 2.46 (ddd, J=11.8, 6.9, 4.8 Hz, 1H), 1.75-1.50 (m, 5H), 1.39 (dq, J=13.0, 7.2 Hz, 1H), 0.87 (t, J=7.2 Hz, 3H). MS (ESI, m/z): 659 ($M^+$+1).

Example 61: Synthesis of Compound S61

In Example 61, the compound 2-53 in Example 53 was replaced with a corresponding raw material 2-61, and a specific structural formula was

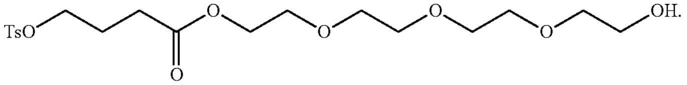

S61

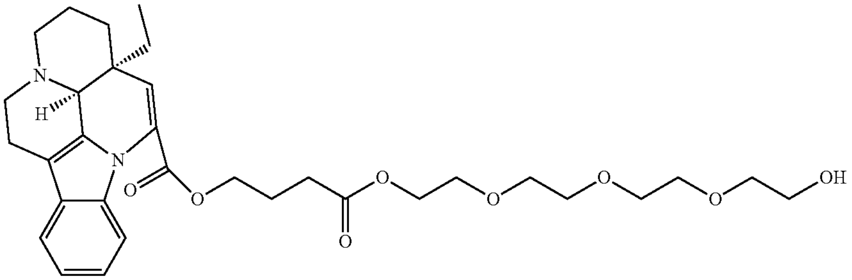

$^1$H NMR (500 MHZ, DMSO-$d_6$) δ 7.54 (dd, J=7.9, 1.4 Hz, 1H), 7.48 (ddd, J=8.0, 6.9, 1.3 Hz, 1H), 7.43 (dd, J=7.8, 1.4 Hz, 1H), 7.27 (ddd, J=8.0, 6.8, 1.3 Hz, 1H), 6.95 (s, 1H), 4.56 (s, 1H), 4.31 (dt, J=12.3, 6.1 Hz, 1H), 4.23 (td, J=6.1, 2.9 Hz, 2H), 4.17 (dt, J=12.2, 6.1 Hz, 1H), 3.83-3.58 (m, 15H), 3.53 (dt, J=12.1, 6.4 Hz, 1H), 3.07 (ddd, J=12.1, 6.5, 4.2 Hz, 1H), 2.94 (ddd, J=15.4, 6.4, 4.2 Hz, 1H), 2.86-2.70 (m, 3H), 2.54-2.37 (m, 3H), 2.22-2.10 (m, 1H), 1.99 (dtt, J=14.0, 7.1, 6.0 Hz, 1H), 1.76-1.62 (m, 3H), 1.64-1.49 (m, 2H), 0.85 (t, J=7.2 Hz, 3H). MS (ESI, m/z): 585 ($M^+$+1).

Example 62: Synthesis of Compound S62

In Example 62, the compound 2-53 in Example 53 was replaced with a corresponding raw material 2-62, and a specific structural formula was

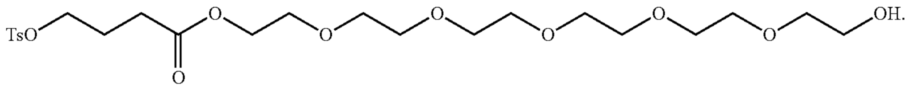

S62

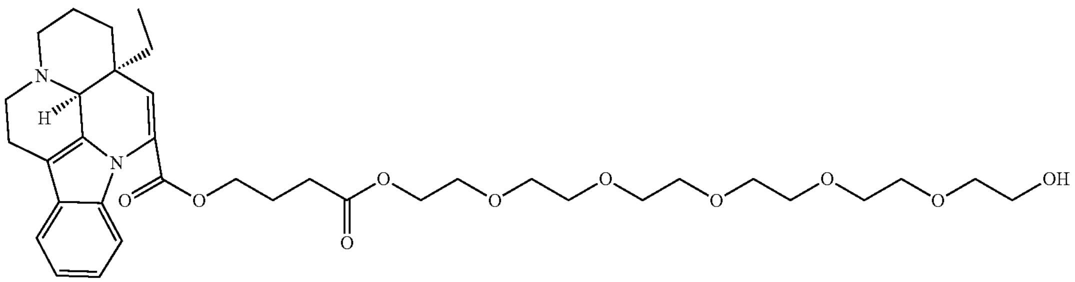

$^1$H NMR (500 MHZ, DMSO-$d_6$) δ 7.53 (dd, J=7.8, 1.3 Hz, 1H), 7.45 (dd, J=7.9, 1.2 Hz, 1H), 7.39 (ddd, J=7.9, 6.8, 1.3 Hz, 1H), 7.26 (ddd, J=8.1, 6.8, 1.3 Hz, 1H), 4.32-4.16 (m, 3H), 4.13 (dt, J=12.3, 6.2 Hz, 1H), 3.83-3.57 (m, 23H), 3.45 (dt, J=12.3, 6.5 Hz, 1H), 3.13 (ddd, J=12.1, 6.4, 4.2 Hz, 1H), 2.90 (ddd, J=15.4, 6.4, 4.2 Hz, 1H), 2.83-2.73 (m, 2H), 2.69 (ddd, J=12.1, 6.4, 4.2 Hz, 1H), 2.52-2.37 (m, 3H), 2.26-2.14 (m, 1H), 2.13-2.01 (m, 1H), 1.75-1.50 (m, 6H), 1.40 (dq, J=12.8, 7.2 Hz, 1H), 0.91 (t, J=7.2 Hz, 3H). MS (ESI, m/z): 673 ($M^+$+1).

All the compounds S63-S65 in the following Examples 63-65 could be obtained according to the synthesis method of Example 1, the generation of the vinpocetine hydrolyzed product in step 1 was the same as that in Example 1, and the reaction process and reaction conditions in step 2 were the same as those in Example 1, and only the compound 1-1 in Example 1 needed to be replaced with a corresponding raw material.

Example 63: Synthesis of Compound S63

In Example 63, the compound 1-1 in Example 1 was replaced with a corresponding raw material 1-63, and a specific structural formula was

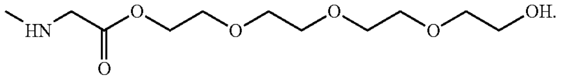

S63

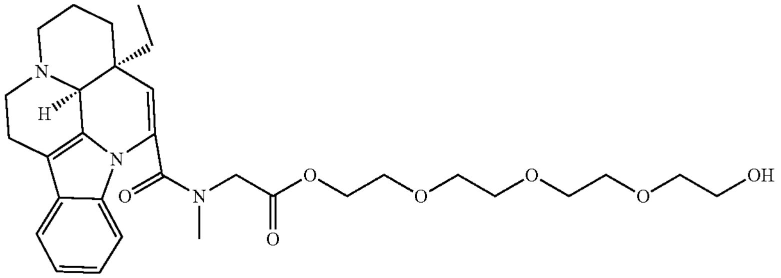

$^1$H NMR (500 MHZ, DMSO-$d_6$) δ 7.57-7.48 (m, 2H), 7.47 (dd, J=8.0, 1.5 Hz, 1H), 7.25 (ddd, J=8.0, 6.8, 1.5 Hz, 1H), 6.84 (s, 1H), 4.53 (s, 1H), 4.34 (dt, J=12.3, 6.2 Hz, 1H), 4.23 (dt, J=12.4, 6.2 Hz, 1H), 4.09 (d, J=13.4 Hz, 1H), 3.89 (d, J=13.4 Hz, 1H), 3.84-3.58 (m, 15H), 3.61-3.53 (m, 1H), 3.49 (dt, J=12.4, 6.3 Hz, 1H), 3.06 (ddd, J=11.9, 6.5, 4.2 Hz, 1H), 2.93 (ddd, J=15.4, 6.3, 4.2 Hz, 1H), 2.88 (s, 2H), 2.86-2.73 (m, 3H), 2.47 (ddd, J=11.9, 6.8, 4.8 Hz, 1H), 1.74-1.49 (m, 5H), 1.43 (dq, J=13.0, 7.2 Hz, 1H), 0.87 (t, J=7.2 Hz, 3H). MS (ESI, m/z): 570 ($M^+$+1).

Example 64: Synthesis of Compound S64

In Example 64, the compound 1-1 in Example 1 was replaced with a corresponding raw material 1-64, and a specific structural formula was

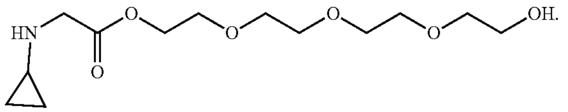

S64

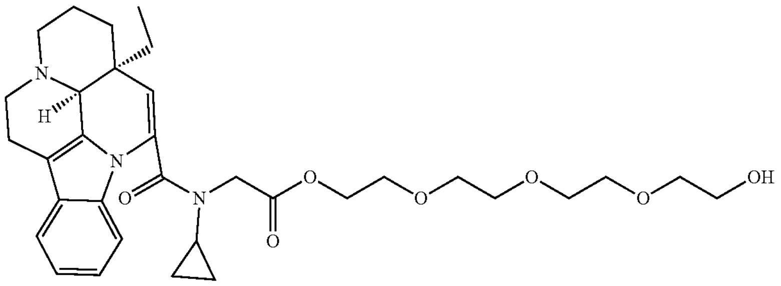

$^1$H NMR (500 MHZ, DMSO-$d_6$) δ 7.60 (dd, J=8.0, 1.3 Hz, 1H), 7.52 (dd, J=7.9, 1.3 Hz, 1H), 7.43 (ddd, J=8.0, 6.9, 1.3 Hz, 1H), 7.27 (ddd, J=8.1, 6.9, 1.3 Hz, 1H), 6.88 (s, 1H), 4.53 (s, 1H), 4.25 (dt, J=12.4, 6.2 Hz, 1H), 4.18-4.04 (m, 2H), 3.88 (d, J=13.3 Hz, 1H), 3.83-3.57 (m, 15H), 3.51-3.42 (m, 1H), 3.22 (p, J=5.7 Hz, 1H), 3.06 (ddd, J=11.9, 6.4, 4.2 Hz, 1H), 2.92 (ddd, J=15.6, 6.4, 4.3 Hz, 1H), 2.86-2.71 (m, 3H), 2.46 (ddd, J=11.9, 6.8, 4.8 Hz, 1H), 1.75-1.49 (m, 5H), 1.43 (dq, J=12.8, 7.2 Hz, 1H), 1.39-1.30 (m, 2H), 1.08-0.99 (m, 2H), 0.87 (t, J=7.2 Hz, 3H). MS (ESI, m/z): 596 ($M^+$+1).

Example 65: Synthesis of Compound S65

In Example 65, the compound 1-1 in Example 1 was replaced with a corresponding raw material 1-65, and a specific structural formula was

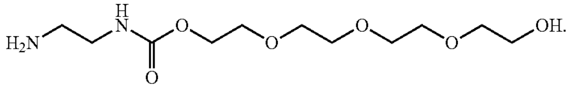

S65

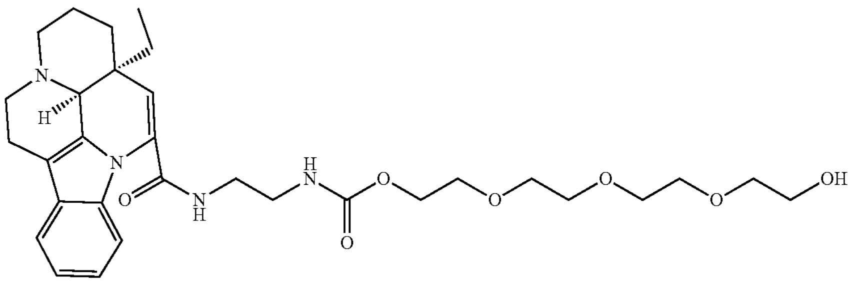

$^1$H NMR (500 MHZ, DMSO-$d_6$) δ 7.94 (t, J=4.2 Hz, 1H), 7.62 (dd, J=7.8, 1.3 Hz, 1H), 7.53 (dd, J=7.9, 1.2 Hz, 1H), 7.45 (ddd, J=7.9, 7.0, 1.2 Hz, 1H), 7.27 (ddd, J=8.1, 7.0, 1.3 Hz, 1H), 6.83 (s, 1H), 5.53 (t, J=4.3 Hz, 1H), 4.52 (s, 1H), 4.35 (dt, J=12.3, 6.2 Hz, 1H), 4.13 (dt, J=12.4, 6.2 Hz, 1H), 3.83-3.57 (m, 13H), 3.55-3.47 (m, 1H), 3.48 (ddt, J=5.8, 5.2, 3.4 Hz, 2H), 3.48-3.39 (m, 1H), 3.42-3.27 (m, 2H), 3.05 (ddd, J=11.9, 6.5, 4.3 Hz, 1H), 2.93 (ddd, J=15.6, 6.4, 4.3 Hz, 1H), 2.86-2.72 (m, 3H), 2.50-2.42 (m, 1H), 1.76-1.50 (m, 5H), 1.40 (dq, J=13.0, 7.2 Hz, 1H), 0.85 (t, J=7.2 Hz, 3H). MS (ESI, m/z): 585 ($M^+$+1).

Example 66: Synthesis of Compound S66

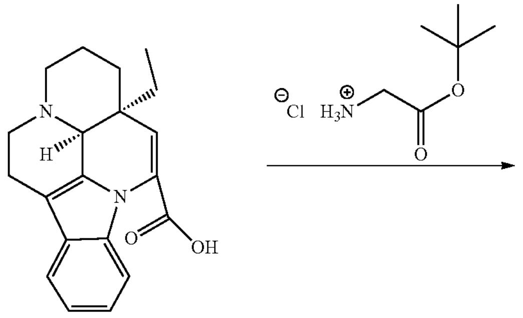

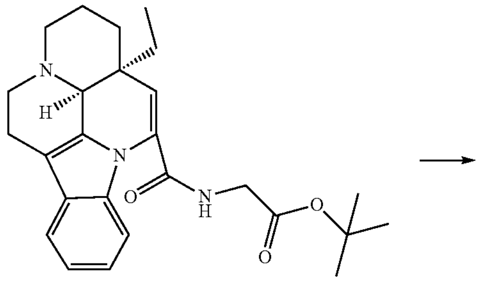

3-66

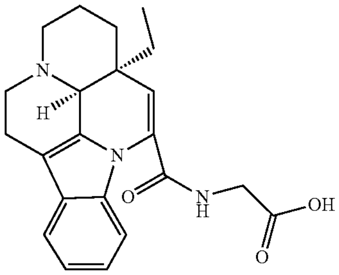

S66

Step 1: Synthesis of Compound 3-66

The vinpocetine hydrolyzed product (200 mg, 0.62 mmol), tert-Butyl glycine hydrochloride (78 mg, 0.62 mmol), EDCI (192 mg, 1.00 mmol) and HOBt (103 mg, 0.76 mmol) were dissolved in anhydrous DMF (8 ml) at room temperature, stirred, added with triethylamine (0.4 mL, 2.94 mmol), protected by nitrogen, and reacted at room temperature for 10 hours. DMF was removed by rotary evaporation, dissolved in dichloromethane, and extracted with dichloromethane (3×20 mL), washed with saturated salt water (1×20 mL), dried over anhydrous sodium sulfate, filtered, concentrated, and subjected to column chromatography separation and purification to obtain an intermediate compound 3-66 (230 mg, 90%). 1H NMR (500 MHZ, Chloroform-d) δ 8.62 (t, J=5.8 Hz, 1H), 7.53 (dt, J=7.7, 1.4 Hz, 2H), 7.44 (ddd, J=8.1, 6.9, 1.3 Hz, 1H), 5.83 (s, 1H), 4.54 (s, 1H), 3.99 (dd, J=17.5, 5.8 Hz, 1H), 3.91 (dd, J=17.6, 5.9 Hz, 1H), 3.06 (ddd, J=12.1, 6.5, 4.3 Hz, 1H), 2.92 (ddd, J=15.6, 6.4, 4.3 Hz, 1H), 2.86-2.72 (m, 4H), 1.75-1.63 (m, 3H), 1.67-1.51 (m, 3H), 1.49-1.38 (m, 1H), 1.42 (s, 9H), 0.88 (t, J=7.2 Hz, 3H).

Step 2: Synthesis of Compound S66

The compound 3-66 (160 mg, 0.35 mmol) was dissolved in dichloromethane (5 ml), added with 2.5 mL of trifluoroacetic acid at 0° C. and transferred to room temperature. The reaction was monitored by TLC until the reaction was completed. Then, the reaction was stopped. The solvent and trifluoroacetic acid were removed under reduced pressure, triturated with ethyl ether (20 mL), filtered, and the filter cake was collected, and dried in vacuum to obtain a vinpocetine-glycine product S66 (119 mg, 90%).

$^1$H NMR (500 MHz, DMSO-$d_6$) δ 11.01 (s, 1H), 8.94 (t, J=5.8 Hz, 1H), 7.55 (ddd, J=16.8, 7.9, 1.3 Hz, 2H), 7.47 (ddd, J=8.0, 6.9, 1.3 Hz, 1H), 7.26 (ddd, J=8.0, 6.9, 1.2 Hz, 1H), 5.67 (s, 1H), 4.57 (s, 1H), 4.15 (dd, J=17.4, 5.7 Hz, 1H), 3.95 (dd, J=17.4, 5.9 Hz, 1H), 3.06 (ddd, J=11.9, 6.5, 4.2 Hz, 1H), 2.93 (ddd, J=15.4, 6.3, 4.2 Hz, 1H), 2.86-2.71 (m, 3H), 2.52-2.43 (m, 1H), 1.76-1.54 (m, 5H), 1.41 (dq, J=13.0, 7.2 Hz, 1H), 0.88 (t, J=7.2 Hz, 3H). MS (ESI, m/z): 380 ($M^+$+1).

All the compounds S67-S87 in the following Examples 67-87 could be obtained according to the synthesis method of Example 1, the reaction process and reaction conditions in step 1 were the same as those in Example 66, and only the tert-Butyl glycine hydrochloride needed to be replaced with a corresponding raw material, and the step 2 was carried out according to the method in Example 66.

Example 67: Synthesis of Compound S67

In Example 67, the tert-Butyl glycine hydrochloride in Example 66 was replaced with a corresponding raw material, and a specific structural formula was

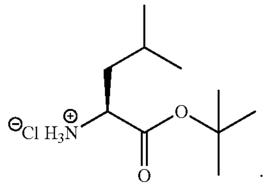

S67

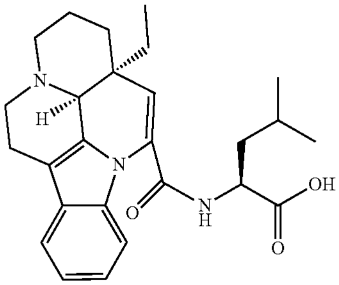

$^1$H NMR (500 MHZ, DMSO-$d_6$) δ 8.97 (d, J=9.3 Hz, 1H), 7.52 (ddd, J=20.6, 7.7, 1.2 Hz, 2H), 7.43 (ddd, J=8.0, 7.0, 1.3 Hz, 1H), 7.26 (ddd, J=8.0, 6.9, 1.3 Hz, 1H), 6.83 (s, 1H), 4.56-4.44 (m, 2H), 3.06 (ddd, J=11.9, 6.5, 4.3 Hz, 1H), 2.92 (ddd, J=15.4, 6.4, 4.2 Hz, 1H), 2.86-2.71 (m, 3H), 2.47 (ddd, J=11.9, 6.8, 4.7 Hz, 1H), 1.90 (dt, J=13.6, 6.8 Hz, 1H), 1.76-1.53 (m, 8H), 1.41 (dq, J=13.0, 7.2 Hz, 1H), 0.95-0.85 (m, 9H). MS (ESI, m/z): 436 ($M^+$+1).

Example 68: Synthesis of Compound S68

In Example 68, the tert-Butyl glycine hydrochloride in Example 66 was replaced with a corresponding raw material, and a specific structural formula was

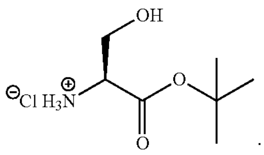

S68

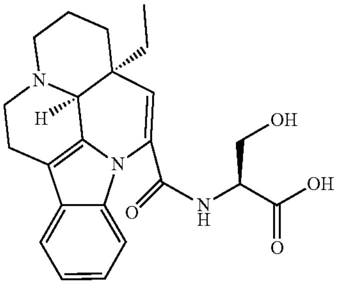

$^1$H NMR (500 MHZ, DMSO-$d_6$) δ 9.41 (d, J=9.3 Hz, 1H), 7.65 (dd, J=7.9, 1.3 Hz, 1H), 7.54 (dd, J=7.9, 1.3 Hz, 1H), 7.45 (ddd, J=8.0, 7.0, 1.3 Hz, 1H), 7.25 (ddd, J=8.0, 6.9, 1.1 Hz, 1H), 6.80 (s, 1H), 4.62 (t, J=7.1 Hz, 1H), 4.54 (s, 1H), 4.33 (dt, J=9.3, 6.4 Hz, 1H), 3.93-3.79 (m, 2H), 3.06 (ddd, J=12.1, 6.4, 4.3 Hz, 1H), 2.92 (ddd, J=15.6, 6.4, 4.3 Hz, 1H), 2.87-2.72 (m, 3H), 2.50-2.42 (m, 1H), 1.75-1.53 (m, 6H), 1.46 (dq, J=13.0, 7.2 Hz, 1H), 0.87 (t, J=7.2 Hz, 3H). MS (ESI, m/z): 410 ($M^+$+1).

Example 69: Synthesis of Compound S69

In Example 69, the tert-Butyl glycine hydrochloride in Example 66 was replaced with a corresponding raw material, and a specific structural formula was

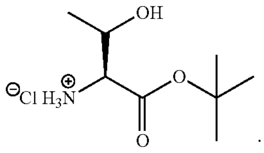

S69

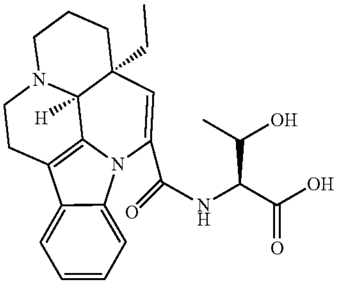

$^1$H NMR (500 MHZ, DMSO-$d_6$) δ 9.44 (d, J=9.2 Hz, 1H), 7.64 (dd, J=8.0, 1.2 Hz, 1H), 7.57-7.48 (m, 2H), 7.26 (ddd, J=8.0, 7.0, 1.3 Hz, 1H), 6.82 (s, 1H), 4.54 (s, 1H), 4.41 (dd, J=9.2, 6.8 Hz, 2H), 4.06 (h, J=6.6 Hz, 1H), 3.07 (ddd, J=12.1, 6.1, 4.5 Hz, 1H), 2.95-2.71 (m, 4H), 2.39 (ddd, J=13.1, 6.8, 4.7 Hz, 1H), 1.75-1.48 (m, 7H), 1.10 (d, J=6.6 Hz, 3H), 0.86 (t, J=7.2 Hz, 3H). MS (ESI, m/z): 424 ($M^+$+1).

Example 70: Synthesis of Compound S70

In Example 70, the tert-Butyl glycine hydrochloride in Example 66 was replaced with a corresponding raw material, and a specific structural formula was

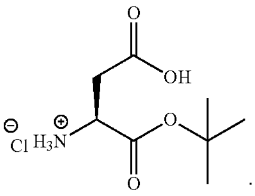

S70

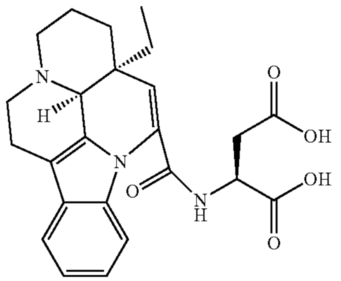

$^1$H NMR (500 MHz, DMSO-$d_6$) δ 9.73 (d, J=9.2 Hz, 1H), 7.54 (dd, J=7.8, 1.3 Hz, 1H), 7.48 (dd, J=7.7, 1.3 Hz, 1H), 7.43 (ddd, J=7.9, 6.8, 1.3 Hz, 1H), 7.26 (ddd, J=8.0, 6.9, 1.5 Hz, 1H), 6.79 (s, 1H), 4.71 (dt, J=9.3, 7.3 Hz, 1H), 4.54 (s, 1H), 3.06 (ddd, J=11.9, 6.4, 4.2 Hz, 1H), 3.02-2.88 (m, 2H), 2.86-2.68 (m, 4H), 2.51-2.43 (m, 1H), 1.76-1.54 (m, 5H), 1.42 (dq, J=13.0, 7.2 Hz, 1H), 0.88 (t, J=7.2 Hz, 3H). MS (ESI, m/z): 438 ($M^+$+1).

Example 71: Synthesis of Compound S71

In Example 71, the tert-Butyl glycine hydrochloride in Example 66 was replaced with a corresponding raw material, and a specific structural formula was

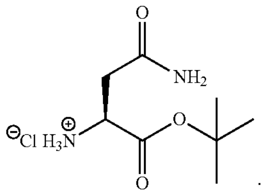

S71

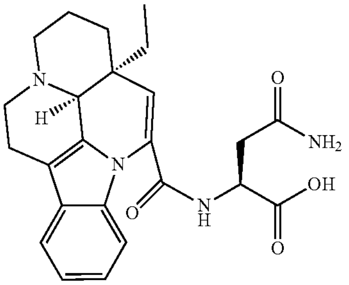

$^1$H NMR (500 MHZ, DMSO-$d_6$) δ 9.57 (d, J=9.3 Hz, 1H), 7.62 (dd, J=8.0, 1.3 Hz, 1H), 7.54 (dd, J=8.0, 1.3 Hz, 1H), 7.44 (ddd, J=8.0, 6.9, 1.3 Hz, 1H), 7.26 (ddd, J=8.0, 6.9, 1.3 Hz, 1H), 7.06 (s, 2H), 6.79 (s, 1H), 4.59 (dt, J=9.3, 7.5 Hz, 1H), 4.00 (s, 1H), 3.14 (ddd, J=12.1, 6.4, 4.2 Hz, 1H), 3.02 (ddd, J=12.1, 6.6, 4.2 Hz, 1H), 2.98-2.73 (m, 3H), 2.70 (dd, J=17.0, 7.3 Hz, 1H), 2.62-2.53 (m, 1H), 1.77-1.64 (m, 3H), 1.60-1.40 (m, 3H), 0.88 (t, J=7.2 Hz, 3H). MS (ESI, m/z): 437 ($M^+$+1).

Example 72: Synthesis of Compound S72

In Example 72, the tert-Butyl glycine hydrochloride in Example 66 was replaced with a corresponding raw material, and a specific structural formula was

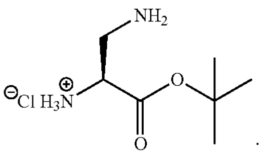

S72

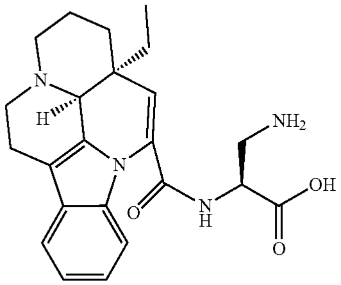

$^1$H NMR (500 MHZ, DMSO-$d_6$) δ 9.03 (d, J=9.3 Hz, 1H), 7.64 (dd, J=8.1, 1.4 Hz, 1H), 7.57-7.49 (m, 2H), 7.25 (ddd, J=8.0, 7.0, 1.3 Hz, 1H), 6.80 (s, 1H), 4.54 (s, 1H), 4.24 (dt, J=9.3, 5.3 Hz, 1H), 3.38 (dt, J=7.1, 5.7 Hz, 1H), 3.31 (dt, J=7.1, 6.0 Hz, 1H), 3.23-3.13 (m, 1H), 3.13-3.03 (m, 2H), 2.94-2.80 (m, 3H), 2.75 (ddd, J=12.1, 6.0, 4.7 Hz, 1H), 2.42-2.33 (m, 1H), 1.74-1.48 (m, 7H), 0.86 (t, J=7.2 Hz, 3H). MS (ESI, m/z): 409 ($M^+$+1).

Example 73: Synthesis of Compound S73

In Example 73, the tert-Butyl glycine hydrochloride in Example 66 was replaced with a corresponding raw material, and a specific structural formula was

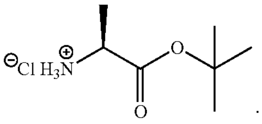

S73

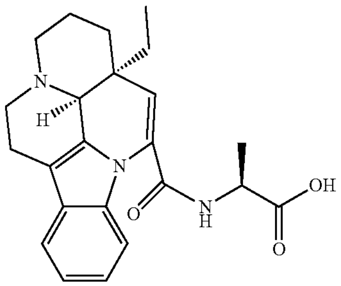

$^1$H NMR (500 MHZ, DMSO-$d_6$) δ 9.30 (d, J=9.3 Hz, 1H), 7.55 (ddd, J=22.5, 7.9, 1.3 Hz, 2H), 7.45 (ddd, J=8.0, 6.9, 1.3 Hz, 1H), 7.26 (ddd, J=8.1, 6.9, 1.2 Hz, 1H), 6.80 (s, 1H), 4.66-4.55 (m, 2H), 3.06 (ddd, J=12.1, 6.4, 4.2 Hz, 1H), 2.93 (ddd, J=15.6, 6.4, 4.3 Hz, 1H), 2.86-2.71 (m, 3H), 2.47 (ddd, J=11.9, 6.8, 4.7 Hz, 1H), 1.76-1.53 (m, 6H), 1.43 (dq, J=13.0, 7.2 Hz, 1H), 1.37 (d, J=6.8 Hz, 3H), 0.88 (t, J=7.2 Hz, 3H). MS (ESI, m/z): 394 ($M^+$+1).

Example 74: Synthesis of Compound S74

In Example 74, the tert-Butyl glycine hydrochloride in Example 66 was replaced with a corresponding raw material, and a specific structural formula was

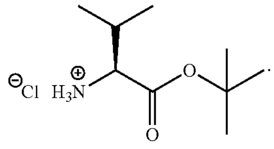

S74

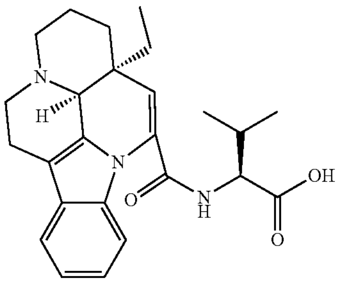

$^1$H NMR (500 MHZ, DMSO-$d_6$) δ 9.34 (d, J=9.2 Hz, 1H), 7.57 (ddd, J=25.9, 7.8, 1.2 Hz, 2H), 7.45 (ddd, J=8.0, 6.9, 1.3 Hz, 1H), 7.26 (ddd, J=8.0, 6.9, 1.3 Hz, 1H), 6.82 (s, 1H), 4.54 (s, 1H), 4.22 (dd, J=9.0, 6.6 Hz, 1H), 3.06 (ddd, J=11.9, 6.4, 4.2 Hz, 1H), 2.92 (ddd, J=15.4, 6.3, 4.2 Hz, 1H), 2.82 (ddd, J=15.4, 6.5, 4.3 Hz, 1H), 2.81-2.71 (m, 2H), 2.51-2.42 (m, 1H), 2.08-1.95 (m, J=6.7 Hz, 1H), 1.75-1.53 (m, 4H), 1.54-1.46 (m, 1H), 1.42 (dq, J=13.0, 7.2 Hz, 1H), 0.97 (dd, J=24.9, 6.6 Hz, 6H), 0.87 (t, J=7.2 Hz, 3H). MS (ESI, m/z): 422 ($M^+$+1).

Example 75: Synthesis of Compound S75

In Example 75, the tert-Butyl glycine hydrochloride in Example 66 was replaced with a corresponding raw material, and a specific structural formula was

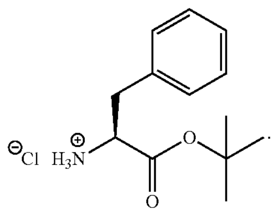

S75

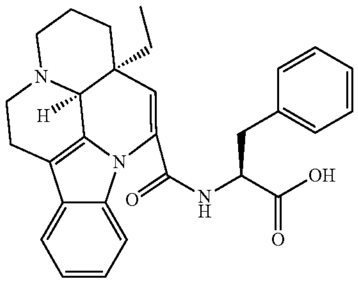

$^1$H NMR (500 MHZ, DMSO-$d_6$) δ 9.16 (d, J=9.3 Hz, 1H), 7.77 (dd, J=8.1, 1.4 Hz, 1H), 7.58 (dd, J=8.0, 1.3 Hz, 1H), 7.52 (ddd, J=7.9, 7.0, 1.1 Hz, 1H), 7.29-7.19 (m, 6H), 6.83

(s, 1H), 4.65 (dt, J=9.3, 7.7 Hz, 1H), 4.54 (s, 1H), 3.14-3.01 (m, 2H), 3.03-2.92 (m, 2H), 2.86 (ddd, J=15.6, 6.4, 4.2 Hz, 1H), 2.84-2.74 (m, 2H), 2.54-2.45 (m, 1H), 1.75-1.64 (m, 2H), 1.68-1.61 (m, 1H), 1.59 (dddd, J=12.8, 6.9, 4.9, 1.8 Hz, 1H), 1.57-1.48 (m, 1H), 1.44 (dq, J=12.8, 7.2 Hz, 1H), 0.87 (t, J=7.2 Hz, 3H). MS (ESI, m/z): 470 ($M^{+}$+1).

Example 76: Synthesis of Compound S76

In Example 76, the tert-Butyl glycine hydrochloride in Example 66 was replaced with a corresponding raw material, and a specific structural formula was

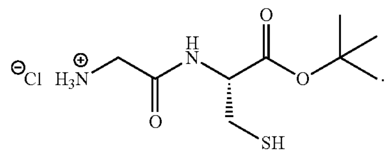

S76

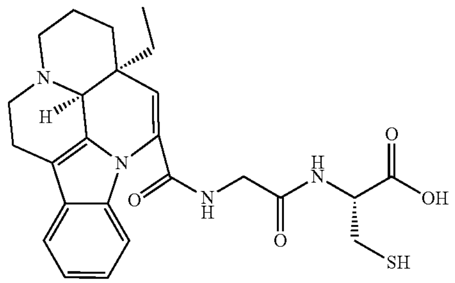

$^{1}$H NMR (500 MHZ, DMSO-$d_6$) δ 8.79 (t, J=5.8 Hz, 1H), 8.19 (d, J=9.3 Hz, 1H), 7.53 (ddd, J=15.9, 7.8, 1.2 Hz, 2H), 7.46 (ddd, J=8.0, 6.9, 1.2 Hz, 1H), 7.26 (ddd, J=8.0, 6.9, 1.4 Hz, 1H), 6.80 (s, 1H), 4.68 (dt, J=9.3, 5.6 Hz, 1H), 4.54 (s, 1H), 4.04 (dd, J=17.4, 5.7 Hz, 1H), 3.90 (dd, J=17.5, 5.8 Hz, 1H), 3.14-3.03 (m, 2H), 3.01-2.87 (m, 2H), 2.88-2.75 (m, 2H), 2.73 (ddd, J=12.1, 6.4, 4.2 Hz, 1H), 2.41-2.32 (m, 1H), 2.08 (t, J=6.6 Hz, 1H), 1.75-1.63 (m, 3H), 1.61-1.39 (m, 3H), 0.84 (t, J=7.2 Hz, 3H). MS (ESI, m/z): 483 ($M^{+}$+1).

Example 77: Synthesis of Compound S77

In Example 77, the tert-Butyl glycine hydrochloride in Example 66 was replaced with a corresponding raw material, and a specific structural formula was

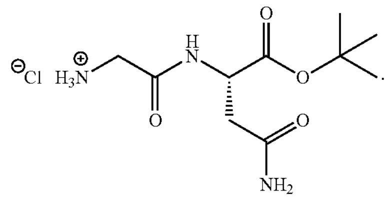

-continued

S77

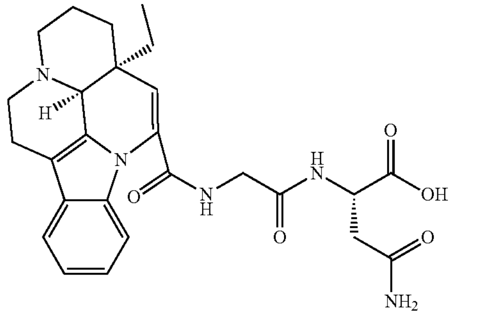

$^{1}$H NMR (500 MHZ, DMSO-$d_6$) δ 8.79 (t, J=5.8 Hz, 1H), 8.19 (d, J=9.3 Hz, 1H), 7.53 (ddd, J=15.9, 7.8, 1.2 Hz, 2H), 7.46 (ddd, J=8.0, 6.9, 1.2 Hz, 1H), 7.26 (ddd, J=8.0, 6.9, 1.4 Hz, 1H), 6.80 (s, 1H), 4.68 (dt, J=9.3, 5.6 Hz, 1H), 4.54 (s, 1H), 4.04 (dd, J=17.4, 5.7 Hz, 1H), 3.90 (dd, J=17.5, 5.8 Hz, 1H), 3.14-3.03 (m, 2H), 3.01-2.87 (m, 2H), 2.88-2.75 (m, 2H), 2.73 (ddd, J=12.1, 6.4, 4.2 Hz, 1H), 2.41-2.32 (m, 1H), 2.08 (t, J=6.6 Hz, 1H), 1.75-1.63 (m, 3H), 1.61-1.39 (m, 3H), 0.84 (t, J=7.2 Hz, 3H). MS (ESI, m/z): 494 ($M^{+}$+1).

Example 78: Synthesis of Compound S78

In Example 78, the tert-Butyl glycine hydrochloride in Example 66 was replaced with a corresponding raw material, and a specific structural formula was

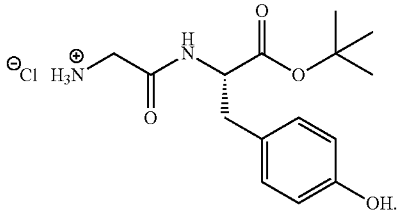

S78

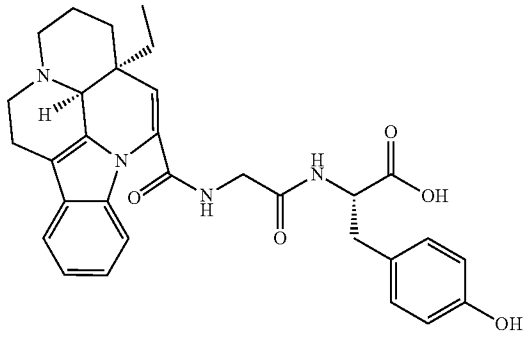

$^{1}$H NMR (500 MHZ, DMSO-$d_6$) δ 8.84 (t, J=5.8 Hz, 1H), 8.16 (d, J=9.3 Hz, 1H), 7.71 (dd, J=8.0, 1.3 Hz, 1H), 7.65 (s, 1H), 7.58 (dd, J=7.9, 1.3 Hz, 1H), 7.51 (ddd, J=8.0, 6.9, 1.3 Hz, 1H), 7.25 (ddd, J=8.0, 7.0, 1.3 Hz, 1H), 6.99 (dt, J=8.7, 1.0 Hz, 2H), 6.82 (s, 1H), 6.70-6.64 (m, 2H), 4.63 (dt, J=9.3, 7.7 Hz, 1H), 4.53 (s, 1H), 3.97 (dd, J=17.4, 5.7 Hz, 1H), 3.90 (dd, J=17.5, 5.8 Hz, 1H), 3.16-3.04 (m, 2H), 3.03-2.89 (m, 2H), 2.86 (ddd, J=15.6, 6.4, 4.3 Hz, 1H), 2.83-2.73 (m, 2H), 2.48 (ddd, J=12.0, 6.9, 4.8 Hz, 1H), 1.76-1.50 (m, 5H), 1.44 (dq, J=13.0, 7.2 Hz, 1H), 0.88 (t, J=7.1 Hz, 3H). MS (ESI, m/z): 542 ($M^{+}$+1).

Example 79: Synthesis of Compound S79

In Example 79, the tert-Butyl glycine hydrochloride in Example 66 was replaced with a corresponding raw material, and a specific structural formula was

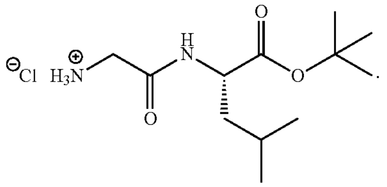

S79

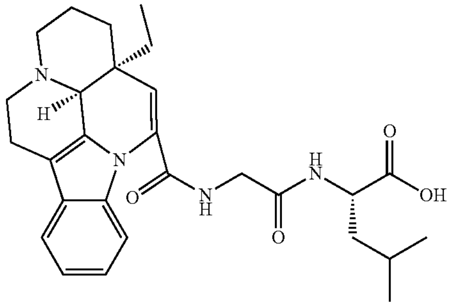

$^1$H NMR (500 MHZ, DMSO-$d_6$) δ 8.85 (t, J=5.8 Hz, 1H), 8.14 (d, J=9.3 Hz, 1H), 7.54 (ddd, J=7.5, 4.8, 1.2 Hz, 2H), 7.46 (ddd, J=8.0, 7.0, 1.3 Hz, 1H), 7.26 (ddd, J=8.0, 6.9, 1.1 Hz, 1H), 6.82 (s, 1H), 4.54 (s, 1H), 4.36 (dt, J=9.3, 6.8 Hz, 1H), 3.97 (dd, J=17.4, 5.7 Hz, 1H), 3.87 (dd, J=17.5, 5.8 Hz, 1H), 3.06 (ddd, J=12.1, 6.5, 4.3 Hz, 1H), 2.93 (ddd, J=15.4, 6.4, 4.3 Hz, 1H), 2.81 (ddd, J=15.4, 6.5, 4.2 Hz, 1H), 2.80-2.71 (m, 2H), 2.51-2.42 (m, 1H), 1.84 (dt, J=13.7, 6.9 Hz, 1H), 1.75-1.66 (m, 1H), 1.70-1.62 (m, 2H), 1.65-1.59 (m, 1H), 1.62-1.49 (m, 2H), 1.53-1.44 (m, 2H), 0.92 (d, J=6.9 Hz, 3H), 0.90-0.82 (m, 6H). MS (ESI, m/z): 493 ($M^+$+1).

Example 80: Synthesis of Compound S80

In Example 80, the tert-Butyl glycine hydrochloride in Example 66 was replaced with a corresponding raw material, and a specific structural formula was

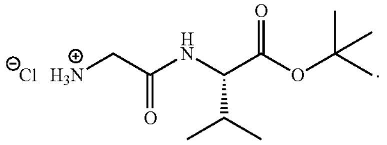

S80

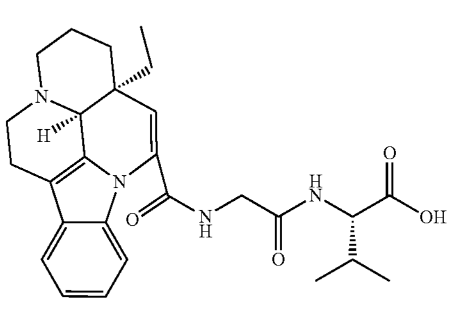

$^1$H NMR (500 MHZ, DMSO-$d_6$) δ 8.79 (t, J=5.8 Hz, 1H), 8.05 (d, J=9.0 Hz, 1H), 7.56 (ddd, J=14.7, 7.9, 1.3 Hz, 2H), 7.45 (ddd, J=8.0, 6.9, 1.3 Hz, 1H), 7.26 (ddd, J=8.0, 6.9, 1.2 Hz, 1H), 6.82 (s, 1H), 4.63 (dd, J=9.0, 6.6 Hz, 1H), 4.54 (s, 1H), 3.97 (dd, J=17.5, 5.8 Hz, 1H), 3.88 (dd, J=17.5, 5.8 Hz, 1H), 3.05 (ddd, J=12.1, 6.5, 4.3 Hz, 1H), 2.92 (ddd, J=15.6, 6.4, 4.3 Hz, 1H), 2.81 (ddd, J=15.6, 6.4, 4.2 Hz, 1H), 2.75 (ddd, J=12.0, 6.5, 4.3 Hz, 2H), 2.46 (ddd, J=12.0, 7.0, 4.9 Hz, 1H), 2.15-2.02 (m, J=6.6 Hz, 1H), 1.78-1.52 (m, 5H), 1.42 (dq, J=13.0, 7.2 Hz, 1H), 0.98 (d, J=6.7 Hz, 3H), 0.96-0.86 (m, 6H). MS (ESI, m/z): 479 ($M^+$+1).

Example 81: Synthesis of Compound S81

In Example 81, the tert-Butyl glycine hydrochloride in Example 66 was replaced with a corresponding raw material, and a specific structural formula was

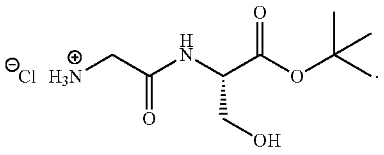

S81

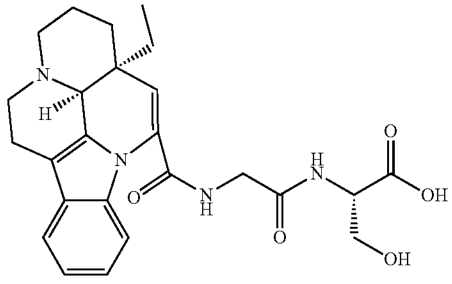

$^1$H NMR (500 MHZ, DMSO-$d_6$) δ 8.78 (t, J=5.8 Hz, 1H), 8.33 (d, J=9.3 Hz, 1H), 7.53 (ddd, J=12.2, 7.9, 1.3 Hz, 2H), 7.45 (ddd, J=8.0, 6.9, 1.2 Hz, 1H), 7.26 (ddd, J=8.0, 6.9, 1.3 Hz, 1H), 6.80 (s, 1H), 4.59-4.52 (m, 2H), 4.49 (dt, J=9.3, 6.4 Hz, 1H), 4.04 (dd, J=17.5, 5.8 Hz, 1H), 3.94-3.76 (m, 3H), 3.07 (ddd, J=12.1, 6.5, 4.2 Hz, 1H), 2.92 (ddd, J=15.4, 6.4, 4.2 Hz, 1H), 2.88-2.69 (m, 3H), 2.41-2.31 (m, 1H), 1.78-1.70 (m, 1H), 1.73-1.63 (m, 3H), 1.60-1.49 (m, 1H), 1.45 (dq, J=13.0, 7.2 Hz, 1H), 0.84 (t, J=7.1 Hz, 3H). MS (ESI, m/z): 467 ($M^+$+1).

Example 82: Synthesis of Compound S82

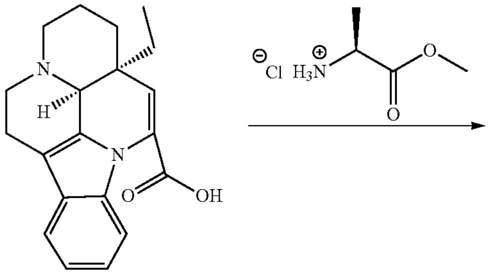

-continued

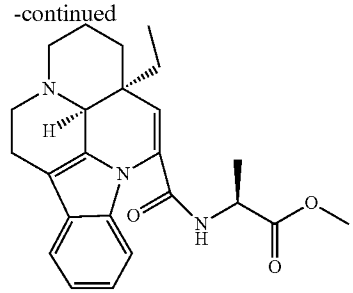

S82

The vinpocetine hydrolyzed product (200 mg, 0.62 mmol), methyl alanine methyl ester hydrochloride (87 mg, 0.62 mmol), EDCI (192 mg, 1.00 mmol) and HOBt (103 mg, 0.76 mmol) were dissolved in anhydrous DMF (8 ml) at room temperature, stirred, added with triethylamine (0.4 mL, 2.94 mmol), protected by nitrogen, and reacted at room temperature for 10 hours. DMF was removed by rotary evaporation, dissolved in dichloromethane, and extracted with dichloromethane (3×20 mL), washed with saturated salt water (1×20 mL), dried over anhydrous sodium sulfate, filtered, concentrated, and subjected to column chromatography separation and purification to obtain a compound S82 (218 mg, 86%).

$^1$H NMR (500 MHZ, DMSO-$d_6$) δ 8.64 (d, J=9.1 Hz, 1H), 7.55 (ddd, J=20.2, 7.7, 1.2 Hz, 2H), 7.46 (ddd, J=7.9, 7.0, 1.2 Hz, 2H), 7.26 (ddd, J=8.0, 6.9, 1.2 Hz, 1H), 6.82 (s, 1H), 4.54 (s, 1H), 4.45 (dq, J=9.3, 6.8 Hz, 1H), 3.70 (s, 2H), 3.07 (ddd, J=11.9, 6.5, 4.2 Hz, 1H), 2.93 (ddd, J=15.4, 6.4, 4.2 Hz, 1H), 2.88-2.77 (m, 2H), 2.75 (ddd, J=12.1, 6.4, 4.3 Hz, 1H), 2.44 (ddd, J=11.9, 6.9, 4.7 Hz, 1H), 1.78-1.51 (m, 5H), 1.43 (dq, J=12.8, 7.1 Hz, 1H), 1.34 (d, J=6.8 Hz, 3H), 0.87 (t, J=7.1 Hz, 3H). MS (ESI, m/z): 408 ($M^+$+1).

All the compounds S83-S87 in the following Examples S83-S87 could be obtained according to the synthesis method of Example 82, and the reaction process and reaction conditions were the same as those in Example 82, and only the methyl alanine methyl ester hydrochloride needed to be replaced with a corresponding raw material.

Example 83: Synthesis of Compound S83

In Example 83, the methyl alanine methyl ester hydrochloride in Example 82 was replaced with a corresponding raw material, and a specific structural formula was

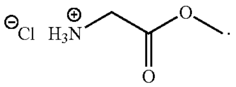

S83

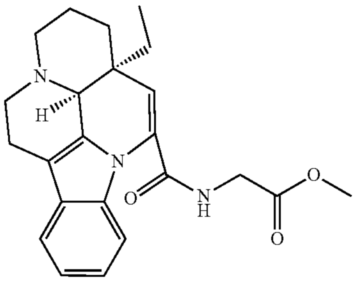

$^1$H NMR (500 MHZ, DMSO-$d_6$) δ 8.55 (t, J=5.8 Hz, 1H), 7.60 (dd, J=7.8, 1.4 Hz, 1H), 7.53 (dd, J=7.9, 1.3 Hz, 1H), 7.46 (ddd, J=8.0, 6.9, 1.3 Hz, 2H), 7.26 (ddd, J=8.1, 6.9, 1.2 Hz, 1H), 6.81 (s, 1H), 4.08 (dd, J=17.5, 5.8 Hz, 1H), 3.98-3.89 (m, 2H), 3.68 (s, 2H), 3.13 (ddd, J=12.3, 6.4, 4.1 Hz, 1H), 3.01 (ddd, J=12.1, 6.4, 4.1 Hz, 1H), 2.93 (ddd, J=15.4, 6.4, 4.1 Hz, 1H), 2.85 (ddd, J=11.7, 6.9, 4.6 Hz, 1H), 2.77 (ddd, J=15.4, 6.4, 4.2 Hz, 1H), 2.57 (ddd, J=11.8, 6.9, 4.7 Hz, 1H), 1.77-1.64 (m, 3H), 1.60-1.51 (m, 1H), 1.55-1.47 (m, 1H), 1.50-1.40 (m, 1H), 0.89 (t, J=7.1 Hz, 3H). MS (ESI, m/z): 394 ($M^+$+1).

Example 84: Synthesis of Compound S84

In Example 84, the methyl alanine methyl ester hydrochloride in Example 82 was replaced with a corresponding raw material, and a specific structural formula was

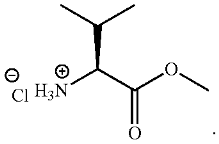

S84

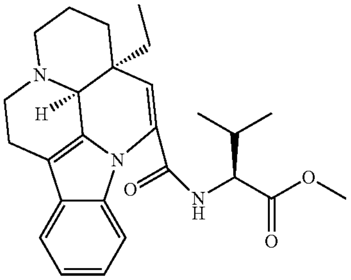

$^1$H NMR (500 MHZ, DMSO-$d_6$) δ 8.67 (d, J=9.0 Hz, 1H), 7.55 (ddd, J=21.7, 7.7, 1.3 Hz, 2H), 7.43 (ddd, J=7.9, 7.0, 1.2 Hz, 2H), 7.26 (ddd, J=8.0, 6.9, 1.3 Hz, 1H), 6.80 (s, 1H), 4.54 (s, 1H), 4.24 (dd, J=9.2, 6.6 Hz, 1H), 3.61 (s, 2H), 3.05 (ddd, J=12.1, 6.4, 4.2 Hz, 1H), 2.91 (ddd, J=15.6, 6.4, 4.3 Hz, 1H), 2.85-2.70 (m, 3H), 2.51-2.42 (m, 1H), 2.20-2.06 (m, J=6.7 Hz, 1H), 1.76-1.53 (m, 5H), 1.41 (dq, J=13.0, 7.2 Hz, 1H), 1.00 (dd, J=25.0, 6.7 Hz, 6H), 0.88 (t, J=7.2 Hz, 3H). MS (ESI, m/z): 436 ($M^+$+1).

Example 85: Synthesis of Compound S85

In Example 85, the methyl alanine methyl ester hydrochloride in Example 82 was replaced with a corresponding raw material, and a specific structural formula was

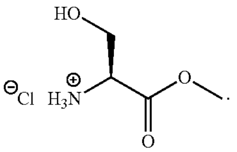

-continued

S85

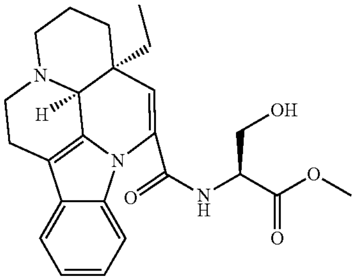

$^1$H NMR (500 MHZ, DMSO-$d_6$) δ 8.94 (d, J=9.3 Hz, 1H), 7.52 (ddd, J=7.9, 6.7, 1.3 Hz, 2H), 7.44 (ddd, J=8.0, 6.9, 1.3 Hz, 1H), 7.26 (ddd, J=8.0, 7.0, 1.3 Hz, 2H), 6.80 (s, 1H), 4.63-4.52 (m, 2H), 4.38 (t, J=7.1 Hz, 1H), 3.98-3.85 (m, 2H), 3.68 (s, 2H), 3.06 (ddd, J=12.1, 6.5, 4.3 Hz, 1H), 2.93 (ddd, J=15.6, 6.4, 4.2 Hz, 1H), 2.85-2.77 (m, 1H), 2.81-2.70 (m, 2H), 2.51-2.42 (m, 1H), 1.76-1.54 (m, 5H), 1.42 (dq, J=13.0, 7.2 Hz, 1H), 0.88 (t, J=7.2 Hz, 3H). MS (ESI, m/z): 424 ($M^+$+1).

Example 86: Synthesis of Compound S86

In Example 86, the methyl alanine methyl ester hydrochloride in Example 82 was replaced with a corresponding raw material, and a specific structural formula was

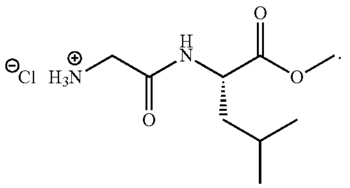

S86

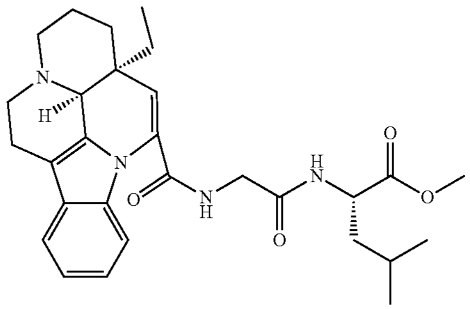

$^1$H NMR (500 MHZ, DMSO-$d_6$) δ 8.83 (t, J=5.8 Hz, 1H), 8.00 (d, J=9.3 Hz, 1H), 7.60-7.49 (m, 3H), 7.25 (ddd, J=8.1, 6.8, 1.3 Hz, 1H), 6.82 (s, 1H), 4.54 (s, 1H), 4.45 (dt, J=9.3, 6.8 Hz, 1H), 4.08 (dd, J=17.5, 5.8 Hz, 1H), 3.90 (dd, J=17.5, 5.8 Hz, 1H), 3.68 (s, 2H), 3.07 (ddd, J=12.1, 6.4, 4.2 Hz, 1H), 2.94 (ddd, J=15.4, 6.3, 4.2 Hz, 1H), 2.88-2.72 (m, 3H), 2.48 (ddd, J=11.8, 6.9, 4.8 Hz, 1H), 1.75-1.49 (m, 9H), 1.43 (dq, J=13.0, 7.2 Hz, 1H), 0.96-0.83 (m, 9H). MS (ESI, m/z): 507 ($M^+$+1).

Example 87: Synthesis of Compound S87

In Example 87, the methyl alanine methyl ester hydrochloride in Example 82 was replaced with a corresponding raw material, and a specific structural formula was

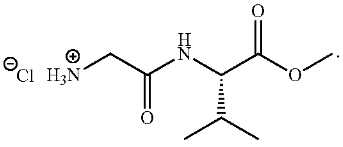

S87

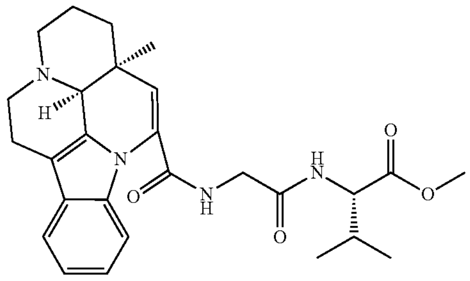

$^1$H NMR (500 MHZ, DMSO-$d_6$) δ 8.85 (t, J=5.8 Hz, 1H), 7.87 (d, J=9.0 Hz, 1H), 7.56 (ddd, J=13.1, 7.9, 1.2 Hz, 2H), 7.45 (ddd, J=8.0, 6.9, 1.3 Hz, 1H), 7.26 (ddd, J=8.0, 6.9, 1.2 Hz, 1H), 6.69 (s, 1H), 4.38 (s, 1H), 4.30 (dd, J=9.1, 6.5 Hz, 1H), 3.97 (dd, J=17.5, 5.8 Hz, 1H), 3.87 (dd, J=17.4, 5.9 Hz, 1H), 3.60 (s, 2H), 3.05 (ddd, J=11.9, 6.4, 4.2 Hz, 1H), 2.92 (ddd, J=15.6, 6.4, 4.3 Hz, 1H), 2.86-2.74 (m, 2H), 2.77-2.71 (m, 1H), 2.46 (ddd, J=11.9, 7.0, 4.7 Hz, 1H), 2.20-2.07 (m, J=6.7 Hz, 1H), 1.73-1.53 (m, 3H), 1.45 (ddd, J=12.2, 6.9, 5.1 Hz, 1H), 1.11 (s, 2H), 0.99 (dd, J=24.9, 6.6 Hz, 6H). MS (ESI, m/z): 479 ($M^+$+1).

Effect Example 1: Axon Growth of Peripheral Sensory Neuron Promoted by Vinpocetine Derivative According to the present invention, an effect of the vinpocetine derivative on promoting the axon growth of the peripheral sensory neuron was detected in a peripheral sensory neuron of Dorsal root ganglion (DRG), and experimental results showed that the vinpocetine derivative had an obvious promotion effect on the axon growth of the peripheral sensory neuron.

Experimental Principle

Diabetic peripheral neuropathy involved a sensory neuron first, and a main pathological change was axonal atrophy and degeneration, or even disappearance. As a peripheral sensory neuron, the DRG neuron had an axon growth state closely related to a development process of the diabetic peripheral neuropathy. Therefore, the compounds in the examples were added with the primary DRG neuron to incubate for a certain period of time, then the axon growth of the DRG neuron was detected by immunofluorescence, and an axon length was quantified by Neuro J, so as to evaluate the promotion effect of the compound on the axon growth of the peripheral sensory neuron.

Experimental Materials and Methods

Primary antibodies of mice anti-β-tubulin III used for fluorescent staining were purchased from Sigma Company, cell culture reagents were all purchased from Gibco Company, and DRG neuronal cells were taken from C57BL/6J mice. Specific experimental steps were as follows: fresh DRG of the C57 mice was extracted to digest into a single-cell suspension and then inoculated into a culture plate for adherent culture overnight, with vinblastine as a positive drug, the to-be-detected compounds S1 to S87 (10 μm) synthesized in the above examples were given to incubate for 24 hours, then an original culture medium was removed, 4% paraformaldehyde was added into each well to fix for 15 minutes after PBS washing, the mixture was permeabilized with 0.3% TritonX-100 for 5 minutes and sealed at room temperature with 4% BSA for 1 hour, a primary antibody (1:1000) was incubated at 4° C. overnight, a goat anti-mouse fluorescent secondary antibody (1:300) was incubated at room temperature in the dark for 1 hour, and a sealed slide was imaged by a fluorescence microscope (Leica). According to the image, a total axon length of a single DRG neuron was tracked by a Neuro J plug-in in Image J software, and a multiple of the total axon length relative to that of the blank control group was calculated.

Experimental Results

Results were shown in Table 1, and compared with the positive drug, the compounds in the examples could better promote the axon growth of the primary DRG neuron. Especially, the compounds S3, S26, S27, S62, S66 and the like had a more outstanding effect.

TABLE 1

Relative total axon length

| Compound Number | Relative total axon length |
|---|---|
| S1 | 9.7 |
| S2 | 9.5 |
| S3 | 13.2 |
| S4 | 11.5 |
| S5 | 12.5 |
| S6 | 11.4 |
| S7 | 10.5 |
| S8 | 11.2 |
| S9 | 10.7 |
| S10 | 10.5 |
| S11 | 9.8 |
| S12 | 12.3 |
| S13 | 11.6 |
| S14 | 10.5 |
| S15 | 11.3 |
| S16 | 11.2 |
| S17 | 12.6 |
| S18 | 11.3 |
| S19 | 10.9 |
| S20 | 10.8 |
| S21 | 9.9 |
| S22 | 10.2 |
| S23 | 10.3 |
| S24 | 11.7 |
| S25 | 12.3 |
| S26 | 13.7 |
| S27 | 12.9 |
| S28 | 12.2 |
| S29 | 12.5 |
| S30 | 12.6 |
| S31 | 11.8 |
| S32 | 12.3 |
| S33 | 10.9 |
| S34 | 10.5 |
| S35 | 12.1 |
| S36 | 11.7 |
| S37 | 10.8 |
| S38 | 10.3 |
| S39 | 11.2 |
| S40 | 11.4 |
| S41 | 11.0 |
| S42 | 10.3 |
| S43 | 11.2 |
| S44 | 9.9 |
| S45 | 10.5 |

TABLE 1-continued

Relative total axon length

| Compound Number | Relative total axon length |
|---|---|
| S46 | 10.7 |
| S47 | 11.2 |
| S48 | 11.4 |
| S49 | 12.0 |
| S50 | 11.3 |
| S51 | 9.8 |
| S52 | 9.5 |
| S53 | 9.9 |
| S54 | 9.7 |
| S55 | 10.5 |
| S56 | 11.3 |
| S57 | 10.8 |
| S58 | 11.4 |
| S59 | 10.6 |
| S60 | 12.0 |
| S61 | 11.3 |
| S62 | 12.8 |
| S63 | 10.9 |
| S64 | 11.3 |
| S65 | 11.0 |
| S66 | 12.8 |
| S67 | 11.3 |
| S68 | 11.0 |
| S69 | 12.3 |
| S70 | 10.8 |
| S71 | 10.5 |
| S72 | 11.3 |
| S73 | 12.1 |
| S74 | 10.9 |
| S75 | 10.7 |
| S76 | 11.1 |
| S77 | 10.8 |
| S78 | 10.2 |
| S79 | 10.6 |
| S80 | 11.3 |
| S81 | 11.9 |
| S82 | 12.5 |
| S83 | 12.7 |
| S84 | 11.0 |
| S85 | 11.8 |
| S86 | 11.0 |
| S87 | 11.7 |
| Vincamine | 9.5 |

Effect Example 2: Motor Nerve Conduction Velocity and Anesthesia of Diabetic Peripheral Neuropathy Improved by Vinpocetine Derivative S26

According to the present invention, taking the vinpocetine derivative S26 prepared in Example 26 as an example, a therapeutic effect of the vinpocetine derivative S26 in vivo was explained, and a structure of the S26 was shown in the following figure. According to the present invention, influences of the S26 on a motor nerve conduction velocity and a pain response of a diabetic peripheral neuropathy model mouse were detected in STZ-induced type-1 diabetes model mice and type-2 diabetes model db/db mice. Experimental results showed that the S26 could obviously improve the reduced motor nerve conduction velocity and the anesthesia of the diabetic peripheral neuropathy model mice.

S26

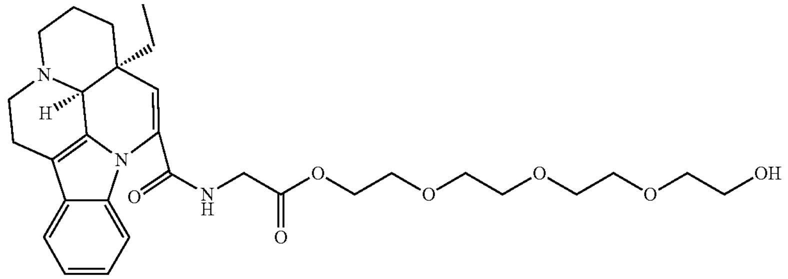

Experimental Principle

The diabetic peripheral neuropathy involved a sensory neuron first, and a main pathological change was axonal atrophy and degeneration, or even disappearance. Therefore, it was considered that a therapeutic effect of anti-diabetic peripheral neuropathy could be achieved by protecting and promoting axon growth of the sensory neuron. In addition, a patient suffering from the diabetic peripheral neuropathy would have symptoms such as nerve conduction velocity reduction, hypoesthesia and fatigue. Behavioral indexes such as the motor nerve conduction velocity, a mechanical pain threshold and a thermal pain reaction time were detected in the diabetic peripheral neuropathy model mice, which could be used to evaluate an improvement effect of the compounds on an individual behavioral level of the diabetic peripheral neuropathy. A protection effect of the compounds on an axon of the peripheral sensory neuron could be evaluated by detecting the axon growth of the peripheral sensory neuron of the administrated mice.

Experimental Materials and Methods

Drug Administration in Groups of Animals

Type-1 diabetes mice: male 8-week-old C57BL/6J mice were purchased from Beijing Vital River Laboratory Animal Technology Co., Ltd. One week after adaptive feeding, STZ (150 mg/kg) was injected intraperitoneally, and one week later, tail vein blood collection was carried out for blood sugar detection, and the mice with random blood sugar greater than 16 mmol/L were selected. Six weeks after STZ injection, the mice were divided into a control group (non-diabetic mice), a model group (DPN mice) and a S26 administration group (46.8 mg/kg/day) respectively according to body weight and blood sugar, and administrated intragastrically for four weeks continuously.

Type-2 diabetes mice: male 18-week-old BKS db/db mice were purchased from Jiangsu Gempharmatech Biotechnology Co., Ltd. One week after adaptive feeding, the mice were divided into a control group (db/m mice), a model group (db/db mice) and a S26 administration group (46.8 mg/kg/day) respectively according to body weight and blood sugar, and administrated intragastrically for four weeks continuously.

Detection Experiment of Motor Nerve Conduction Velocity

Before administration, 2 weeks and 4 weeks after administration, motor nerve conduction velocities (MNCV) of left and right sides of each group of mice were detected, and a mean value of the velocities of two sides was taken as a nerve conduction velocity of each mouse. Specific experimental method: (1) electrode placement: a stimulating electrode was placed on a nerve trunk, a recording electrode was placed on a muscle belly, and a reference electrode was placed on a muscle tendon; and a ground electrode was placed between the stimulating electrode and the recording electrode. (2) Calculation of motor nerve conduction velocity: distal and proximal ends of the nerve trunk were stimulated in a super-strong manner, a compound muscle action potential could be recorded twice on a muscle innervated by the nerve, different latent periods of the compound muscle action potentials were measured, and a distance between the distal and proximal ends was divided by a difference between the two latent periods, so as to obtain the nerve conduction velocity. Computational formula: nerve conduction velocity (m/s)=distance between two ends (cm)×10/difference between two latent periods (ms).

Detection Experiment of Mechanical Pain Threshold

This experiment was based on a principle that claws of rodents would have a withdrawal reflex under mechanical stimulation. A Von frey tactile measuring set was purchased from Ugo Basile Company, and Von frey filaments could provide 0.008 g to 300 g of stimulating force, wherein a thickness of the filaments determined a magnitude of the stimulating force. Specific experimental method: filaments with proper thicknesses were selected to vertically stimulate a skin, and the stimulating force was adjusted by replacing the filaments, until the filaments were bent. One mouse was tested for 6 times to determine a threshold, and a 50% mechanical pain threshold of the mouse was calculated according to 50% threshold=(10^($X_f$+k δ))/10000, which was detected weekly before and after administration respectively.

Detection Experiment of Latent Period of Thermal Pain

A response of an animal to infrared thermal stimulation was detected weekly by an infrared plantar pain threshold detector (37370, purchased from Ugo Basile Company) before and after administration to characterize a thermal pain sensitivity of the animal. A mouse was put into a single cage equipped for the machine in advance to adapt for 20 minutes, and then plantar thermal stimulation was carried out on the mouse. With the extension of time, the temperature was gradually increased, and when the mouse lifted feet or moved away from a heat source, the machine automatically stopped and recorded a thermal stimulation time, which was the latent period of the thermal pain. The thermal pain sensitivity was evaluated by comparing the thermal stimulation time.

Experiment of Axon Growth of Dorsal Root Ganglion Neuron Cells

After administration, a fresh DRG neuron of a mouse was extracted to digest into a single-cell suspension and then inoculated into a culture plate for adherent culture overnight. A β-tubulin III (Sigma) protein of the DRG neuron cells was labeled by an immunofluorescence staining method. The protein was imaged by a fluorescence microscope (Leica), and a total axon length of a single DRG neuron cell was tracked by a Neuro J plug-in in Image J software.

Experimental Results

As shown in Tables 2 to 4, the compound S26 could obviously improve a motor nerve conduction velocity and an anesthesia symptom of a type-1 diabetes peripheral neuropathy mouse. Significance analysis was carried out by T test between the two sets of data. *p<0.05, p<0.01 and *p<0.001 represented a model group vs. a control group ordb/db vs. db/m; and *p<0.05, p<0.01 and *p<0.001 represented an administration group vs. the model group or S26 vs. db/db.

TABLE 2

| Motor nerve conduction velocity (Mean ± SD., n = 3, m/s) | | | |
|---|---|---|---|
| Number of weeks of administration | Control group | Model group | S26 administration group |
| 0 | 38.79 ± 2.10 | 20.74 ± 1.28*** | 20.37 ± 3.21 |
| 2 | 37.68 ± 2.02 | 20.06 ± 3.44** | 27.48 ± 2.97# |
| 4 | 40.87 ± 3.22 | 19.62 ± 4.79** | 31.11 ± 3.85# |

TABLE 3

| 50% mechanical pain threshold (Mean ± SD., n = 6, g) | | | |
|---|---|---|---|
| Number of weeks of administration | Control group | Model group | S26 administration group |
| 0 | 0.83 ± 0.22 | 1.51 ± 0.20*** | 1.51 ± 0.22 |
| 1 | 0.81 ± 0.29 | 1.59 ± 0.39** | 1.06 ± 0.34# |
| 2 | 0.87 ± 0.24 | 1.61 ± 0.45** | 0.92 ± 0.24## |
| 3 | 0.79 ± 0.25 | 1.68 ± 0.27*** | 0.87 ± 0.15### |
| 4 | 0.81 ± 0.29 | 1.69 ± 0.44** | 0.85 ± 0.23## |

TABLE 4

| Latent period of thermal pain (Mean ± SD., n = 6, s) | | | |
|---|---|---|---|
| Number of weeks of administration | Control group | Model group | S26 administration group |
| 0 | 6.24 ± 0.36 | 11.50 ± 0.49*** | 11.33 ± 0.67 |
| 1 | 6.34 ± 0.43 | 11.63 ± 1.12*** | 8.19 ± 0.69### |
| 2 | 6.29 ± 0.67 | 11.40 ± 0.32*** | 6.97 ± 0.73### |
| 3 | 6.17 ± 0.65 | 11.55 ± 0.71*** | 6.16 ± 1.33### |
| 4 | 6.26 ± 0.69 | 11.51 ± 0.62*** | 6.38 ± 0.54### |

As shown in Tables 5 to 7, the S26 could obviously improve a motor nerve conduction velocity and an anesthesia symptom of a type-2 diabetes mouse.

TABLE 5

| Motor nerve conduction velocity (Mean ± SD., n = 3, m/s) | | | |
|---|---|---|---|
| Number of weeks of administration | db/m | db/db | S26 |
| 0 | 44.81 ± 5.01 | 19.08 ± 0.91*** | 20.45 ± 3.94 |
| 2 | 42.12 ± 7.06 | 19.43 ± 1.47** | 29.70 ± 4.27# |
| 4 | 42.96 ± 2.57 | 19.39 ± 1.05*** | 36.57 ± 3.34## |

TABLE 6

| 50% mechanical pain threshold (Mean ± SD., n = 6, g) | | | |
|---|---|---|---|
| Number of weeks of administration | db/m | db/db | S26 |
| 0 | 0.56 ± 0.22 | 1.46 ± 0.22*** | 1.33 ± 0.56 |
| 1 | 0.55 ± 0.11 | 1.55 ± 0.54** | 1.04 ± 0.55 |
| 2 | 0.58 ± 0.23 | 1.43 ± 0.36*** | 0.91 ± 0.37# |
| 3 | 0.50 ± 0.24 | 1.50 ± 0.53** | 0.72 ± 0.39# |
| 4 | 0.47 ± 0.16 | 1.52 ± 0.34*** | 0.71 ± 0.42## |

TABLE 7

| Latent period of thermal pain (Mean ± SD., n = 6, s) | | | |
|---|---|---|---|
| Number of weeks of administration | db/m | db/db | S26 |
| 0 | 5.47 ± 1.05 | 15.83 ± 1.55*** | 15.55 ± 2.29 |
| 1 | 4.88 ± 0.99 | 16.02 ± 2.09*** | 13.50 ± 2.05 |
| 2 | 4.80 ± 1.10 | 15.72 ± 2.04*** | 12.00 ± 2.28# |
| 3 | 4.93 ± 1.10 | 15.45 ± 1.37*** | 8.62 ± 1.51### |
| 4 | 4.78 ± 0.91 | 15.07 ± 1.79*** | 7.65 ± 1.30### |

As shown in FIG. 1, the vinpocetine derivative S26 could obviously improve axon growth conditions of DRG neurons of type-1 and type-2 diabetes peripheral neuropathy model mice (fluorescence image). Quantitative results were shown in Table 8, which showed that the vinpocetine derivative S26 had a protection effect on the axon of the peripheral sensory neuron.

TABLE 8

| Total axon length (Mean ± SD., n = 6, pixel) | | | |
|---|---|---|---|
| Type-1 | Control group | Model group | S26 administration group |
| Total axon length | 5732.65 ± 690.58 | 2656.97 ± 165.97*** | 6374.12 ± 371.56### |
| Type-2 | db/m | db/db | S26 |
| Total axon length | 5845.64 ± 1020.82 | 2963.02 ± 906.22*** | 6070.18 ± 579.43### |

Effect Example 3: Healing of Foot Ulcer Wound of Diabetic Foot Model Rat Promoted by Vinpocetine Derivative S26

According to the present invention, an influence of the vinpocetine derivative S26 on the healing of the foot ulcer wound of the diabetic foot model rat was detected in a STZ-induced diabetic rat. Experimental results showed that after the diabetic rat suffered from foot ulcer, the treatment with the compound S26 could obviously promote the healing of the foot ulcer wound and reduce an injured area.

Experimental Principle

Diabetic foot ulcer (DFU) was the most common manifestation of diabetic foot, and was also a main cause of amputation of a diabetic patient. In this experiment, a certain area of wound was created on a foot back of the diabetic rat at one time to form a diabetic foot ulcer model, and then the compound S26 was administrated for treatment. The influence of the vinpocetine derivative S26 on the healing of the diabetic foot ulcer was evaluated by taking a photo of the wound and quantifying an area of the wound.

Experimental Materials and Methods

Establishment of Diabetic Rat Model

Male 5-week-old SPF-level Sprague Dawley rats were purchased from Beijing Weitong Lihua Experimental Animal Technology Co., Ltd. One week after adaptive feeding, STZ (100 mg/kg) was injected intraperitoneally, and 72 hours later, tail vein blood collection was carried out for blood sugar detection, and the rats with random blood sugar greater than 16.7 mmol/L were selected.

Establishment of Diabetic Foot Ulcer Rat Model

Four weeks after STZ injection, an inhalation anesthesia machine was used to carry out isoflurane inhalation to induce anesthesia, and a complete round skin wound was created on a rear foot back of the diabetic rat through a disposable 5 mm skin biopsy punch and a Westcott scissor. After the establishment of the diabetic foot ulcer rat model, the rats were divided into a control group (non-diabetic rats), a model group (DFU rats) and a S26 administration group (46.8 mg/kg/day) respectively according to blood sugar and body weight, and administrated intragastrically for four weeks continuously.

Observation on Ulcer Area of Diabetic Foot Rat

The foot ulcer wound of each rat was observed on day 0, day 3, day 7, day 14, day 21 and day 28 after administration, and photographed with a camera, and then the wound area was quantified by Image J software through scale conversion.

Experimental Results

Figure 2:
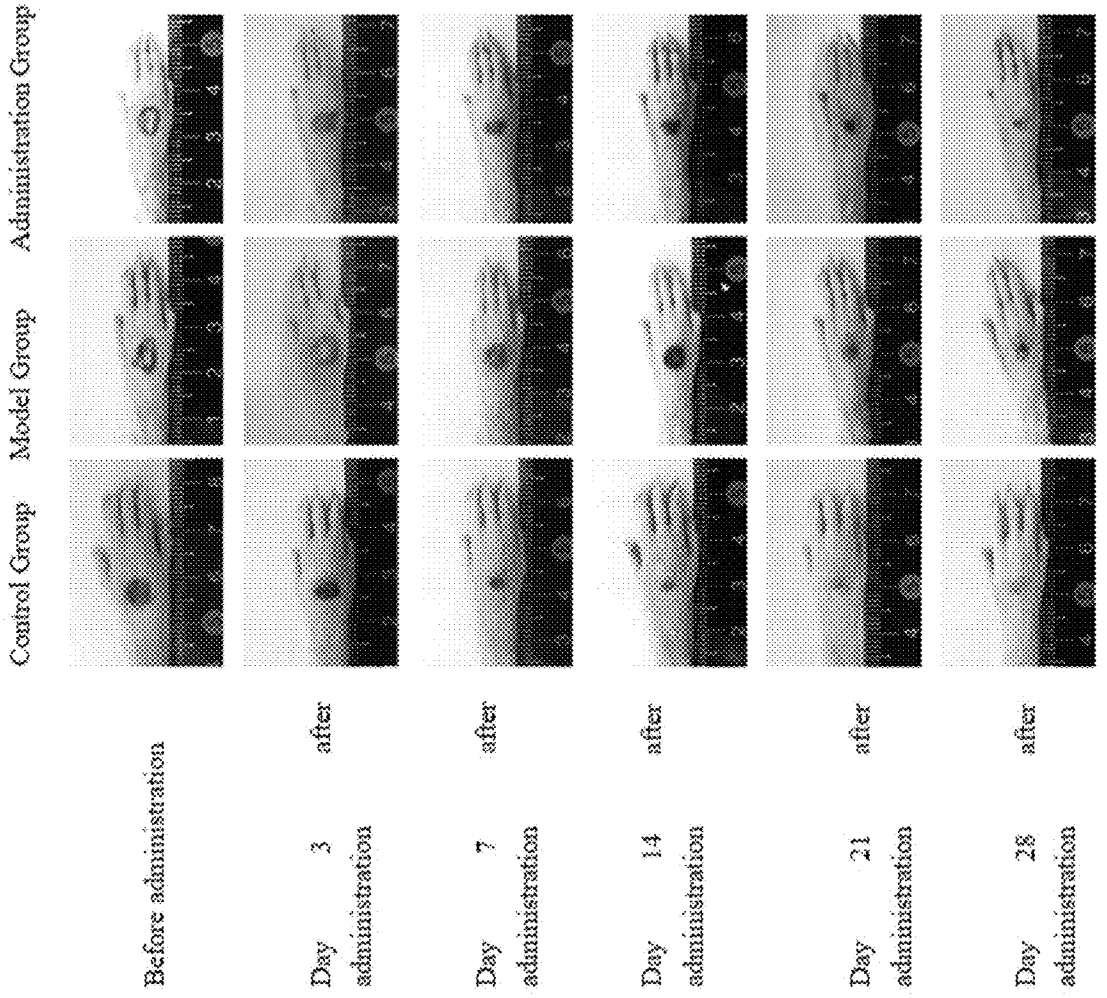
FIG. 2 is a picture of a foot wound in which the vinpocetine derivative S26 can obviously promote the healing of foot ulcer wounds in diabetic foot rats.

As shown in FIG. 2, the vinpocetine derivative S26 could obviously reduce the area of the foot ulcer wound in the diabetic foot rat, and the quantitative results of the wound area were shown in Table 9, which showed that the vinpocetine derivative S26 could promote the healing of the diabetic foot ulcer wound.

TABLE 9

Area of foot ulcer wound (Mean ± SD., n = 6, $mm^2$)

| Number of days of administration | Control group | Model group | S26 administration group |
|---|---|---|---|
| 0 | 25.17 ± 2.16 | 25.65 ± 2.49 | 25.02 ± 2.85 |
| 3 | 19.47 ± 1.34 | 23.67 ± 2.55** | 22.57 ± 2.76 |
| 7 | 13.10 ± 1.98 | 18.68 ± 4.33* | 11.83 ± 3.73# |
| 14 | 6.85 ± 1.56 | 15.15 ± 2.82*** | 10.50 ± 2.01## |
| 21 | 4.03 ± 0.97 | 12.82 ± 2.66*** | 8.78 ± 1.35## |
| 28 | 2.90 ± 1.04 | 9.82 ± 3.39*** | 6.02 ± 1.67# |

Effect Example 4: Degree of Bleomycin-Induced Pulmonary Fibrosis of Mouse Reduced by Vinpocetine Derivative S26

According to the present invention, a protection effect of the vinpocetine derivative S26 on a lung tissue of the mouse was detected in a bleomycin-induced pulmonary fibrosis mouse by Micro CT. Experimental results showed that the treatment with the compound S26 could obviously reduce the degree of pulmonary fibrosis of the mouse.

Experimental Principle

In this experiment, the pulmonary fibrosis model was established by oral tracheal instilling of a bleomycin solution into the mouse, and then the compound S26 was administrated for treatment. A volume of a normal lung tissue of the mouse was quantified by carrying out CT photographing and three-dimensional reconstruction on a lung of the mouse to evaluate the influence of the vinpocetine derivative S26 on the degree of the bleomycin-induced pulmonary fibrosis of the mouse.

Experimental Materials and Methods

Male 8-week-old C57BL/6J mice were purchased from Beijing Weitong Lihua Experimental Animal Technology Co., Ltd. One week after adaptive feeding, a lung development condition of the mouse was examined by micro-CT. The mice were divided into a blank control group (normal mice), a model group and a S26 administration group (46.8 mg/kg) according to a volume of a normal lung tissue. Subsequently, an inhalation anesthesia machine was used to carry out isoflurane inhalation to induce anesthesia. The mice in the model group and the administration group were given 5 mg/kg bleomycin solution through oral tracheal instilling to establish the pulmonary fibrosis model, while the mice in the control group were given the same volume of bleomycin solvent. The mice were administrated on day 8 after the establishment of the model, and were intragastrically administrated for 20 days continuously. Micro-CT imaging was carried out before the establishment of the model and on day 8, day 18 and day 28 after the establishment of the model to observe pulmonary fibrosis of the mice.

Experimental Results

Figure 3:
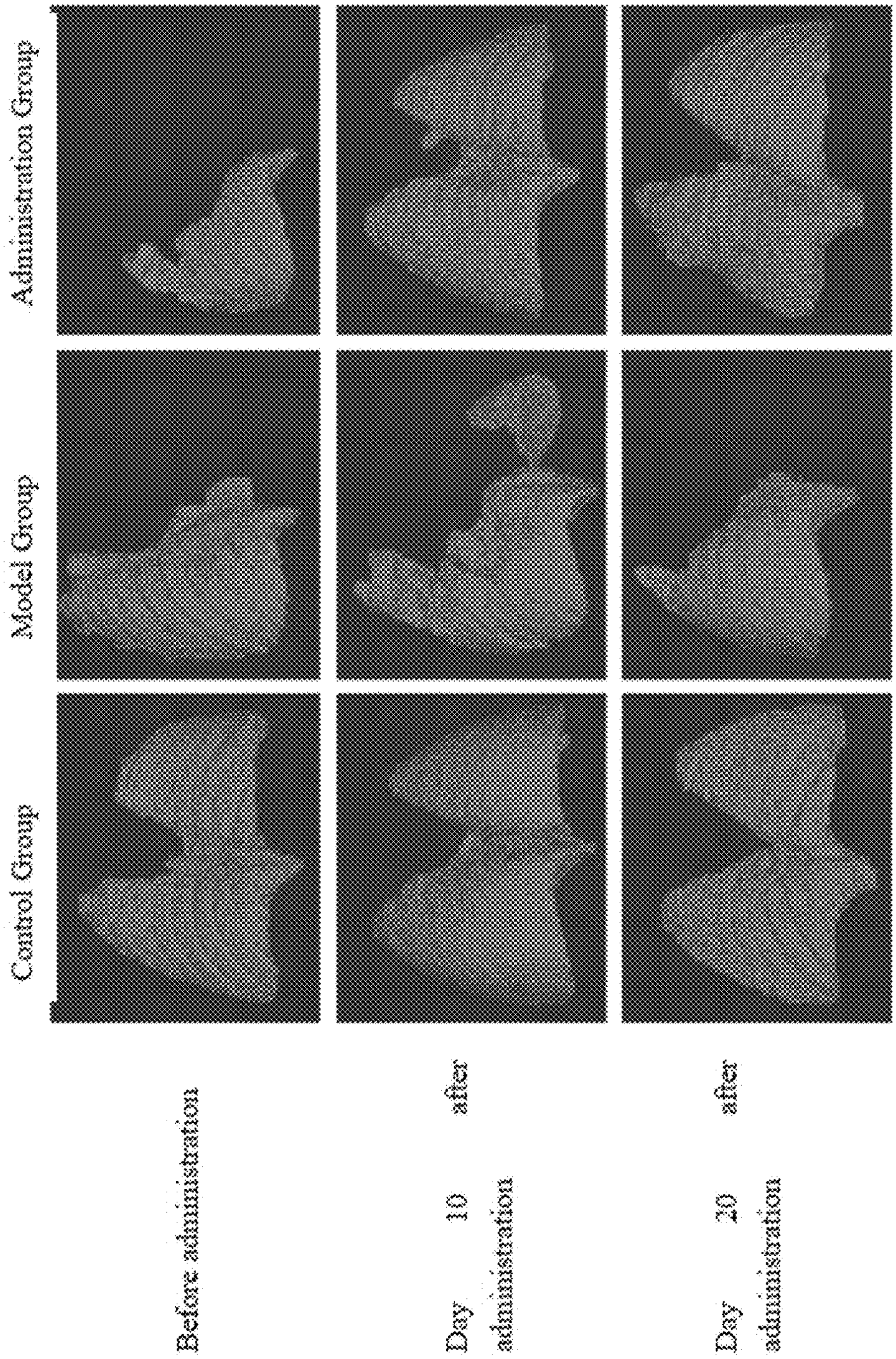
FIG. 3 is a lung CT picture showing that the vinpocetine derivative S26 can obviously improve a degree of pulmonary fibrosis in mice.

As shown in FIG. 3, the vinpocetine derivative S26 could obviously increase the volume of the normal lung tissue of the pulmonary fibrosis model mouse, and the quantitative results were shown in Table 10, which showed that the vinpocetine derivative S26 could obviously reduce the degree of bleomycin-induced pulmonary fibrosis of the mouse, thus having a certain protection effect on the lung tissue.

TABLE 10

Volume of normal lung tissue (Mean ± SD., n = 4, $mm^3$)

| Number of days of administration | Control group | Model group | S26 administration group |
|---|---|---|---|
| 0 | 526.63 ± 38.60 | 323.24 ± 46.26*** | 328.98 ± 34.15 |
| 10 | 549.34 ± 58.16 | 382.88 ± 57.41** | 486.71 ± 48.61# |
| 20 | 543.08 ± 51.28 | 380.28 ± 20.72** | 536.70 ± 58.44## |

The above description is merely exemplary embodiments of the present invention, but is not intended to limit the present invention. The scope of protection of the present invention is defined by the claims. Those skilled in the art can make various modifications or equivalent substitutions to the present invention without departing from the essence and scope of protection of the present invention, and those modifications or equivalent substitutions shall all fall within the scope of protection of the present invention.

What is claimed is:

1. A compound represented by formula I, or a pharmaceutically acceptable salt thereof, or an isomer thereof, wherein the formula I is shown as follows:

I

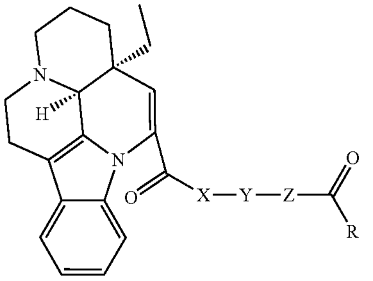

in the formula:

X is O or $-NR^1$;

$R^1$ is hydrogen, unsubstituted or $R^{1-1}$ substituted $C_{1-6}$ alkyl, $C_{6-10}$ aryl, $C_{3-10}$ cycloalkyl, 5-10 membered heteroaryl, or 4-10 membered heterocycloalkyl, and $C_{3-10}$ cycloalkyl-($C_{1-4}$ alkyl)- or $C_{6-12}$ aryl-($C_{1-4}$ alkyl)-;

$R^{1-1}$ is halogen or hydroxyl;

Y is —($CH_2$) m-;

m is an integer from 1 to 6;

Z is a single bond,

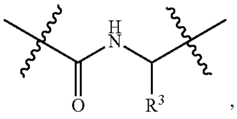
,
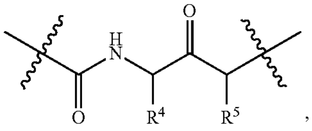
,
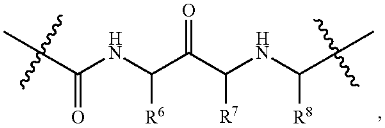
,
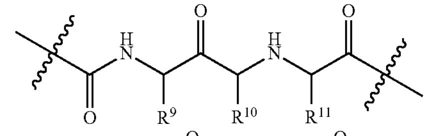
or
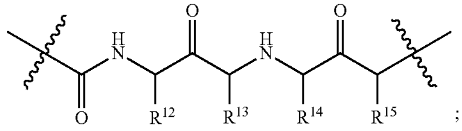
;

$R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from hydrogen, unsubstituted or $R^{3-1}$ substituted $C_{1-6}$ alkyl, $C_{6-10}$ aryl, unsubstituted or $R^{3-2}$ substituted $C_{6-12}$ aryl-($C_{1-4}$ alkyl)-, heteroaryl, or heteroaryl-($C_{1-4}$ alkyl)-; and the heteroaryl is 5-10 membered heteroaryl;

$R^{3-1}$ is hydroxyl, carboxyl, amino, sulfhydryl, —(C═O) $NR^{3-1-1}$, or —NH(C═NH)$NH_2$;

$R^{3-1-1}$ is hydrogen or $C_{1-4}$ alkyl;

$R^{3-2}$ is halogen or hydroxyl;

R is hydrogen, hydroxyl, $C_{2-6}$ alkoxy or

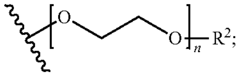

$R^2$ is $C_{1-6}$ alkyl or hydrogen;

n is an integer from 1 to 500; and

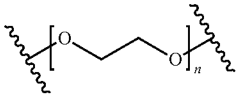

is polyethylene glycol (PEG) with a linear, tree, star or hyperbranched structure comprising —$(OCH_2CH_2)_n$—; wherein the tree-shaped PEG is a polymer with a highly symmetrical, tree-like architecture, synthesized layer by layer from a central core to form a precise, multi-branched structure; the star-shaped PEG is a branched polymer architecture in which multiple linear PEG chains emanate from a central core molecule, creating a star-like or radial topology; the hyperbranched PEG is a three-dimensional, globular polymer obtained through a one-step synthesis; it possesses a densely yet irregularly branched structure, lacking the perfect symmetry of dendritic polymers.

2. The compound according to claim 1, wherein when $R^1$ is unsubstituted or $R^{1-1}$ substituted $C_{1-6}$ alkyl, the number of $R^{1-1}$ is one or more, and when more $R^{1-1}$ are provided, the $R^{1-1}$ may be the same or different;

and/or, when $R^1$ is unsubstituted or $R^{1-1}$ substituted $C_{1-6}$ alkyl, the $C_{1-6}$ alkyl is $C_{1-4}$ alkyl;

and/or, when $R^1$ is $C_{6-10}$ aryl, the $C_{6-10}$ aryl is phenyl;

and/or, when $R^1$ is $C_{3-10}$ cycloalkyl, the $C_{3-10}$ cycloalkyl is $C_{3-6}$ cycloalkyl;

and/or, when $R^1$ is $C_{6-12}$ aryl-($C_{1-4}$ alkyl)-, the $C_{6-12}$ aryl-($C_{1-4}$ alkyl)- is benzyl;

and/or, when $R^1$ is $C_{3-10}$ cycloalkyl-($C_{1-4}$ alkyl)-, the $C_{3-10}$ cycloalkyl-($C_{1-4}$ alkyl)- is $C_{3-6}$ cycloalkyl-($C_{1-2}$ alkyl);

and/or, when $R^{1-1}$ is halogen, the halogen is fluorine, chlorine, bromine or iodine;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{1-6}$ alkyl, the number of $R^{3-1}$ is one or more, and when more $R^{3-1}$ are provided, the $R^{3-1}$ may be the same or different;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{1-6}$ alkyl, the $C_{1-6}$ alkyl is $C_{1-4}$ alkyl;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-2}$ substituted $C_{6-12}$ aryl-($C_{1-4}$ alkyl)-, the number of $R^{3-2}$ is one or more, and when more $R^{3-2}$ are provided, the $R^{3-2}$ may be the same or different;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{6-12}$ aryl-($C_{1-4}$ alkyl)-, the $C_{6-12}$ aryl-($C_{1-4}$ alkyl)- is $C_{6-12}$ aryl-($C_{1-2}$ alkyl)-;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from 5-10 membered heteroaryl-($C_{1-4}$ alkyl)-, the 5-10 membered heteroaryl-($C_{1-4}$ alkyl)- is 5-9 membered heteroaryl-($CH_2$)—;

and/or, when $R^{3-1-1}$ is $C_{1-4}$ alkyl, the $C_{1-4}$ alkyl is methyl, ethyl, n-propyl or isopropyl;

and/or, m is an integer from 1 to 4;

and/or, n is an integer from 0-1 to 400;

and/or,

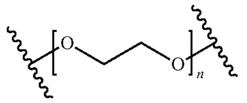

is polyethylene glycol with a linear structure comprising —$(OCH_2CH_2)_n$—;

and/or, when $R^2$ is $C_{1-6}$ alkyl, the $C_{1-6}$ alkyl is $C_{1-4}$ alkyl;

and/or, when R is $C_{2-6}$ alkoxy, the $C_{2-6}$ alkoxy is $C_{1-4}$ alkoxy.

3. The compound according to claim 1, wherein when $R^1$ is unsubstituted or $R^{1-1}$ substituted $C_{1-6}$ alkyl, the number of $R^{1-1}$ is 1, 2 or 3;

and/or, when $R^1$ is unsubstituted or $R^{1-1}$ substituted $C_{1-6}$ alkyl, the $C_{1-6}$ alkyl is methyl, ethyl, n-propyl, isopropyl, n-butyl, isobutyl, sec-butyl or tertiary butyl;

and/or, when $R^1$ is $C_{3-10}$ cycloalkyl, the $C_{3-10}$ cycloalkyl is cyclopropyl, cyclobutyl, cyclopentyl or cyclohexyl;

and/or, when $R^1$ is $C_{3-10}$ cycloalkyl-($C_{1-4}$ alkyl)-, the $C_{3-10}$ cycloalkyl-($C_{1-4}$ alkyl)- is cyclopropylmethyl, cyclobutylmethyl, cyclopentylmethyl or cyclohexylmethyl;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{1-6}$ alkyl, the number of $R^{3-1}$ is 1, 2 or 3;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-1}$ substituted $C_{1-6}$ alkyl, the $C_{1-6}$ alkyl is methyl, ethyl, n-propyl, isopropyl, n-butyl, sec-butyl or tertiary butyl;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-2}$ substituted $C_{6-12}$ aryl-($C_{1-4}$ alkyl)-, the number of $R^{3-2}$ is 1, 2 or 3;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from unsubstituted or $R^{3-2}$ substituted $C_{6-12}$ aryl-($C_{1-4}$ alkyl)-, the $C_{6-12}$ aryl-($C_{1-4}$ alkyl)- is benzyl;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from 5-10 membered heteroaryl-($C_{1-4}$ alkyl)-, the 5-10 membered heteroaryl-($C_{1-4}$ alkyl)- is indolylmethyl or imidazolylmethyl;

and/or, m is an integer from 1 to 2;

and/or, n is an integer from 1 to 100;

and/or, when $R^2$ is $C_{1-6}$ alkyl, the $C_{1-6}$ alkyl is methyl, ethyl, n-propyl, isopropyl, n-butyl, isobutyl, sec-butyl or tertiary butyl;

and/or, when R is $C_{2-6}$ alkoxy, the $C_{2-6}$ alkoxy is ethoxy, n-propoxy, isopropoxy, n-butoxy, sec-butoxy, isobutoxy or tert-butoxy.

4. The compound according to claim 1, wherein when $R^1$ is $R^{1-1}$ substituted $C_{1-6}$ alkyl, the $R^{1-1}$ substituted $C_{1-6}$ alkyl is trifluoromethyl, or

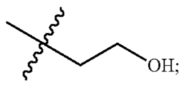 [SMILES: *CCO]

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from $R^{3-1}$ substituted $C_{1-6}$ alkyl, the $R^{3-1}$ substituted $C_{1-6}$ alkyl is

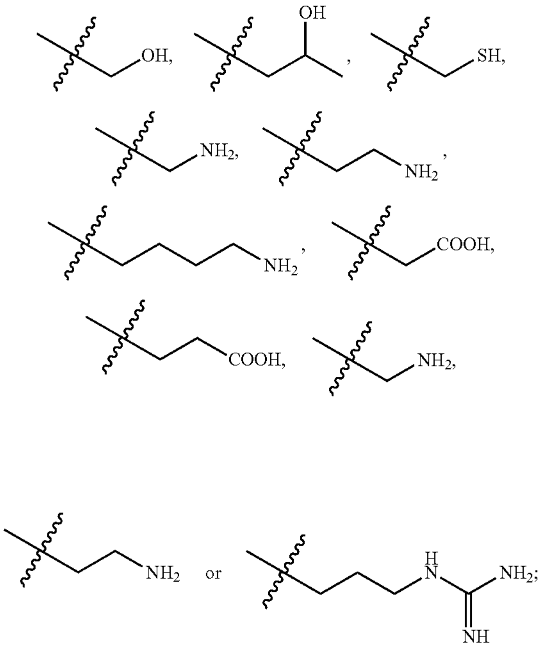

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from $R^{3-2}$ substituted $C_{6-12}$ aryl-($C_{1-4}$ alkyl)-, the $R^{3-2}$ substituted $C_{6-12}$ aryl-($C_{1-4}$ alkyl)- is

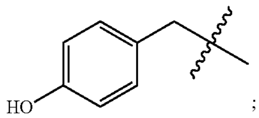 [SMILES: *Cc1ccc(O)cc1]

;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from 5-10 membered heteroaryl-($C_{1-4}$ alkyl)-, the 5-10 membered heteroaryl-($C_{1-4}$alkyl)- is

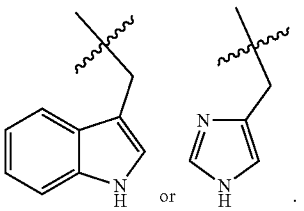

.

5. The compound according to claim 1, wherein $R^1$ is hydrogen, unsubstituted or $R^{1-1}$ substituted $C_{1-6}$ alkyl or $C_{3-10}$ cycloalkyl;

and/or, $R^{1-1}$ is hydroxyl;

and/or, m is an integer from 1 to 2;

and/or, Z is a single bond or

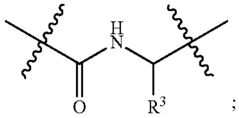

;

and/or, when $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from hydrogen, unsubstituted or $R^{3-1}$ substituted $C_{1-6}$ alkyl, unsubstituted or $R^{3-2}$ substituted $C_{6-12}$ aryl-($C_{1-4}$ alkyl)-, and heteroaryl-($C_{1-4}$ alkyl)-, the heteroaryl is 5-10 membered heteroaryl;

and/or, $R^{3-1}$ is hydroxyl, carboxyl, amino, sulfhydryl, —(C═O)$NR^{3-1-1}$, or —NH(C═NH)$NH_2$;

and/or, $R^{3-1-1}$ is hydrogen;

and/or, $R^{3-2}$ is hydroxyl;

and/or, n is an integer from 1 to 400;

and/or,

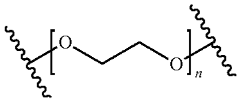

is polyethylene glycol with a linear structure comprising —$(OCH_2CH_2)_n$—.

6. The compound according to claim 1, wherein:

X is O or —$NR^1$;

$R^1$ is hydrogen, unsubstituted or $R^{1-1}$ substituted $C_{1-6}$ alkyl or $C_{3-10}$ cycloalkyl;

$R^{1-1}$ is hydroxyl;

Y is —$(CH_2)_m$—;

m is an integer from 1 to 2;

Z is a single bond or

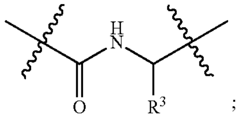

;

$R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from hydrogen, unsubstituted or $R^{3-1}$ substituted $C_{1-6}$ alkyl, unsubstituted or $R^{3-2}$ substituted $C_{6-12}$ aryl-($C_{1-4}$ alkyl)-, or heteroaryl-($C_{1-4}$ alkyl)-, and the heteroaryl is 5-10 membered heteroaryl;

$R^{3-1}$ is hydroxyl, carboxyl, amino, sulfhydryl, —(C═O)$NR^{3-1-1}$, or —NH(C═NH)$NH_2$;

$R^{3-1-1}$ is hydrogen;

$R^{3-2}$ is hydroxyl;

R is hydrogen, hydroxyl, $C_{1-6}$ alkoxy or

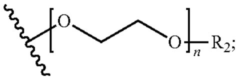

;

$R^2$ is $C_{1-6}$ alkyl or hydrogen;

n is an integer from 1 to 400; and

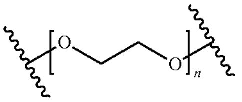

is polyethylene glycol with a linear structure comprising —$(OCH_2CH_2)_n$—.

7. The compound according to claim 1, wherein:

X is —$NR^1$;

$R^1$ is hydrogen;

Y is —$(CH_2)_m$—;

m is an integer from 1 to 2;

Z is a single bond or

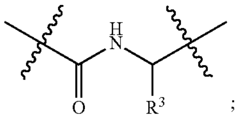

;

$R^3$ is hydrogen, or unsubstituted or $R^{3-1}$ substituted $C_{1-6}$ alkyl;

$R^{3-1}$ is hydroxyl, carboxyl, amino, sulfhydryl, —(C═O)$NR^{3-1-1}$, or —NH(C═NH)$NH_2$;

$R^{3-1-1}$ is hydrogen;

R is hydrogen, hydroxyl, $C_{2-6}$ alkoxy or

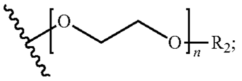

;

$R^2$ is $C_{1-6}$ alkyl or hydrogen;

n is an integer from 0 to 100; and

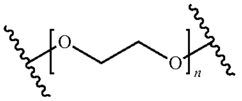

is polyethylene glycol with a linear structure comprising —$(OCH_2CH_2)_n$—.

8. A compound for treating a disease, wherein the compound is selected from the group consisting of:
S1
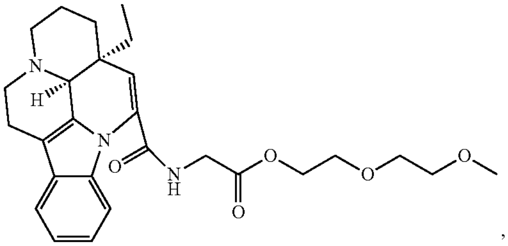
,
S2
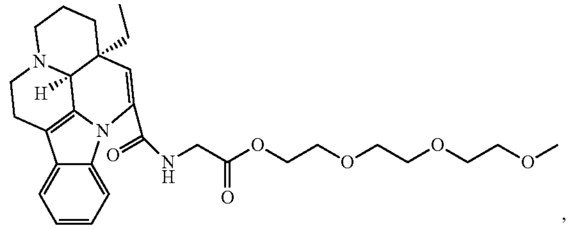
,
S3
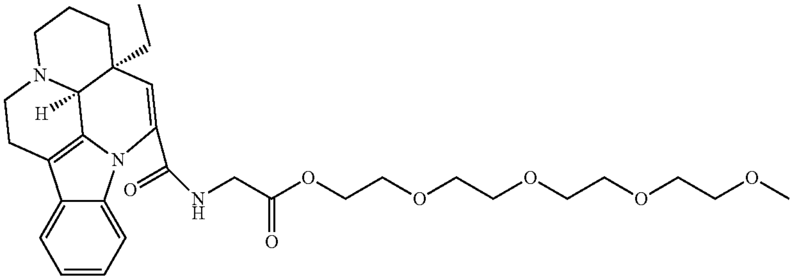
,
S4
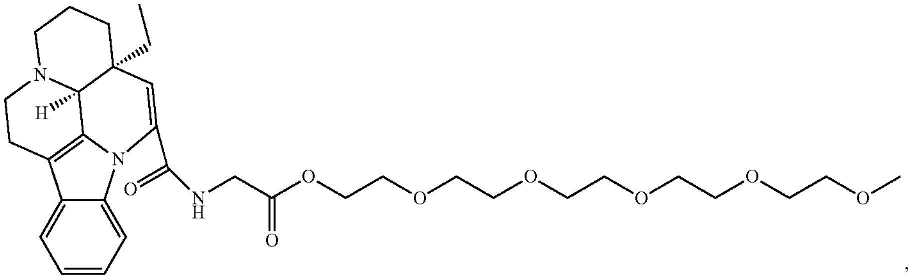
,
S5
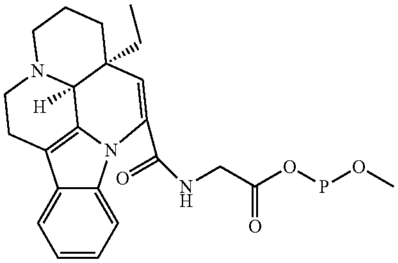
P = PEG-2000,
S6
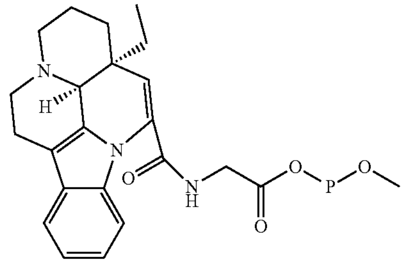
P = PEG-1000,
S7
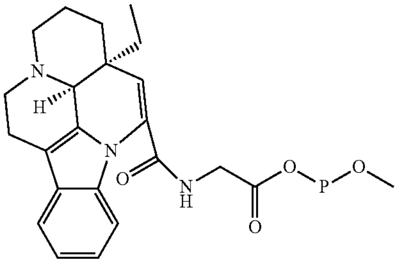
P = PEG-400,
S8
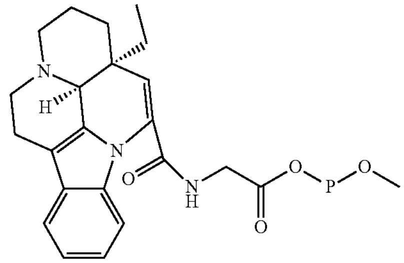
P = PEG-8000, -continued
S9
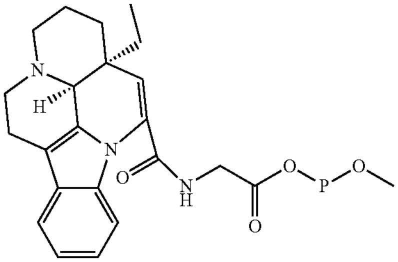
P = PEG-5000,
S10
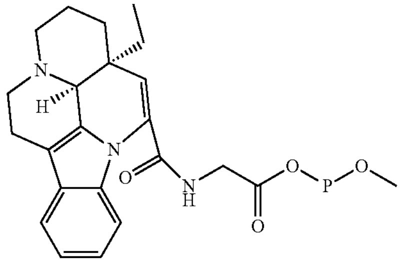
P = PEG-12000,
S11
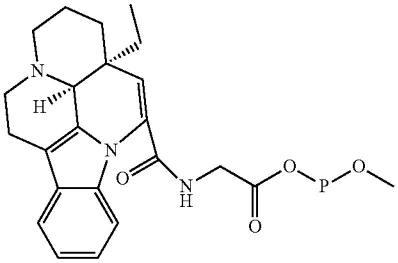
P = PEG-20000,
S12
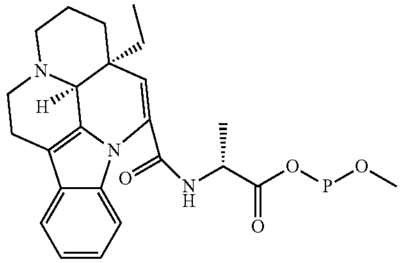
P = PEG-2000,
S13
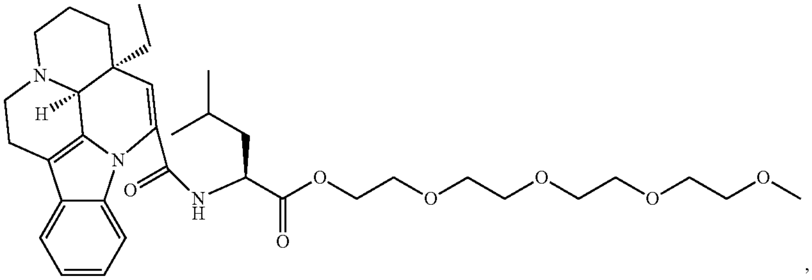
,
S14
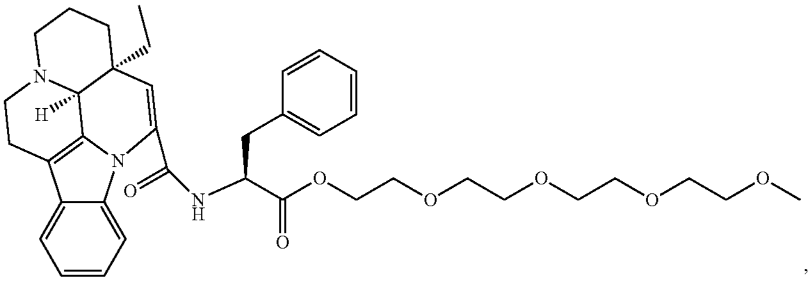
,
S15
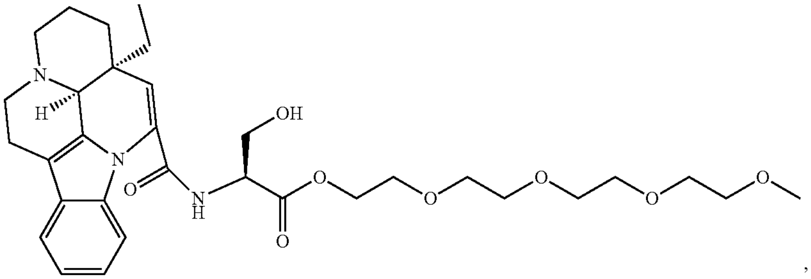
, -continued
S16
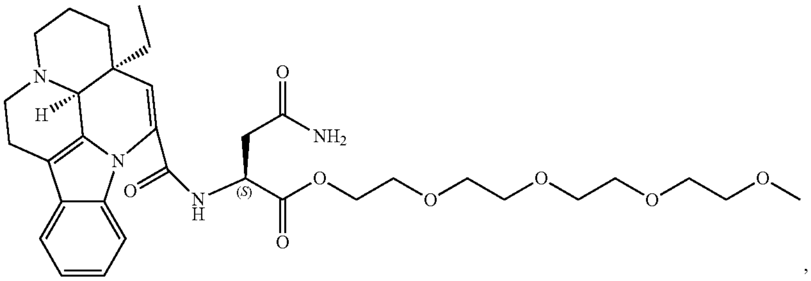
,
S17
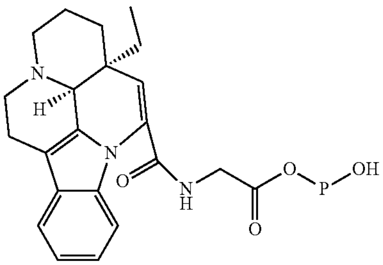
P = PEG-2000,
S18
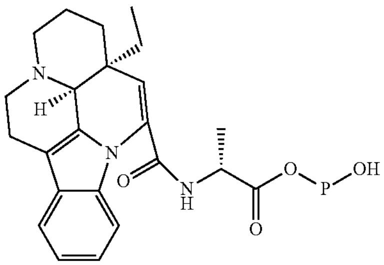
P = PEG-2000,
S19
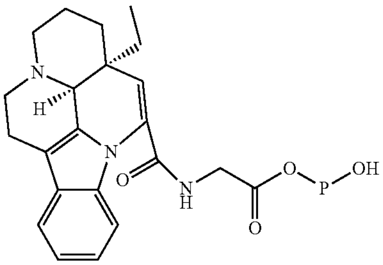
P = PEG-4000,
S20
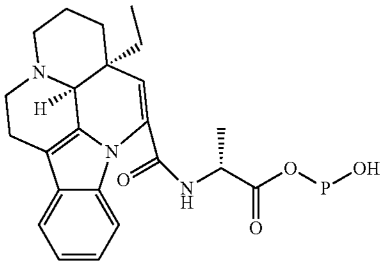
P = PEG-4000,
S21
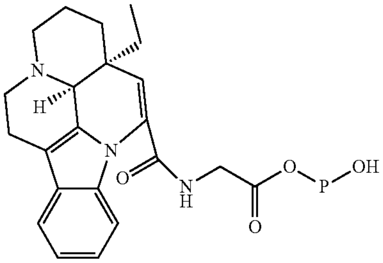
P = PEG-400,
S22
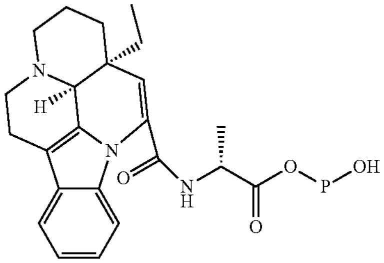
P = PEG-400,
S23
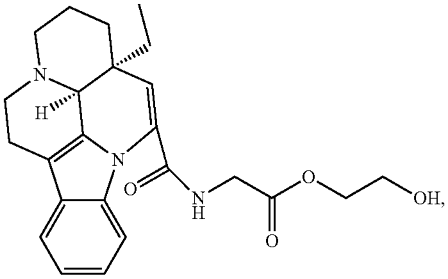
S24
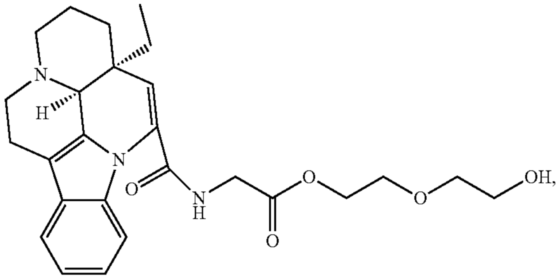

-continued
S25
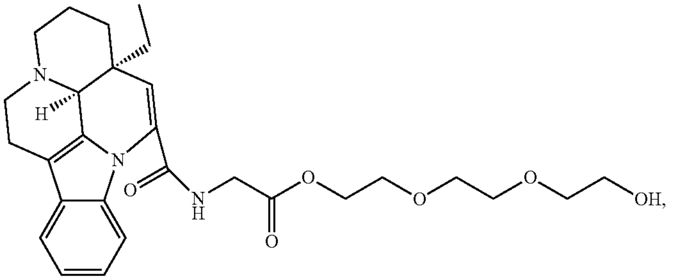
S26
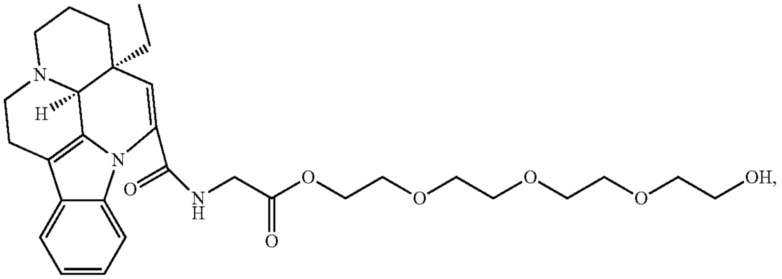
S27
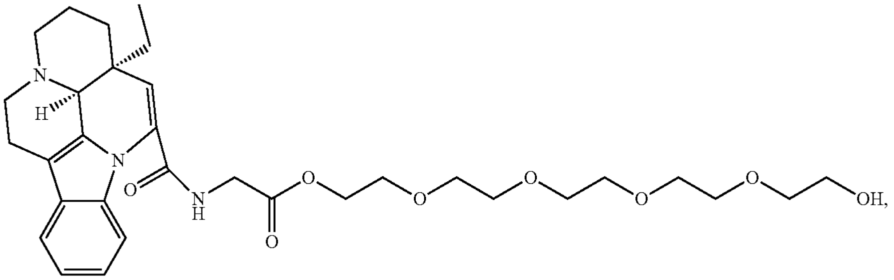
S28
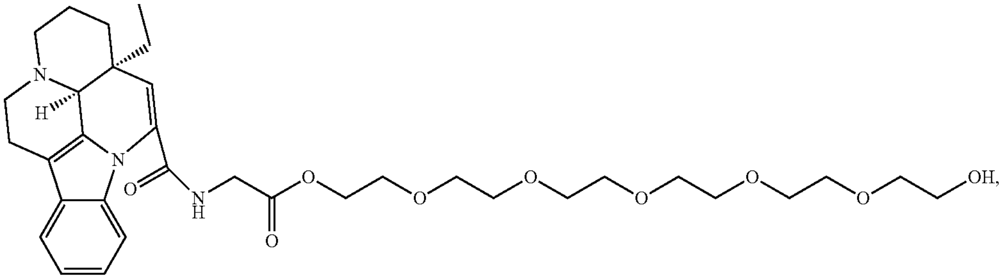
S29
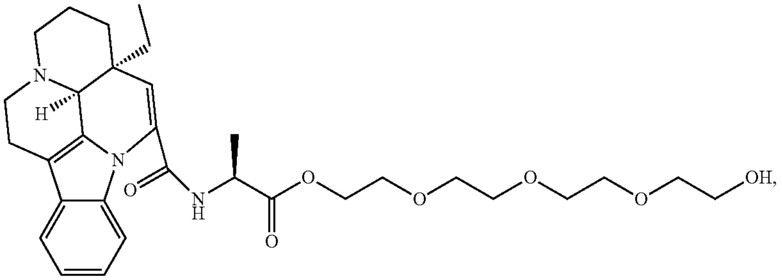

-continued
S30
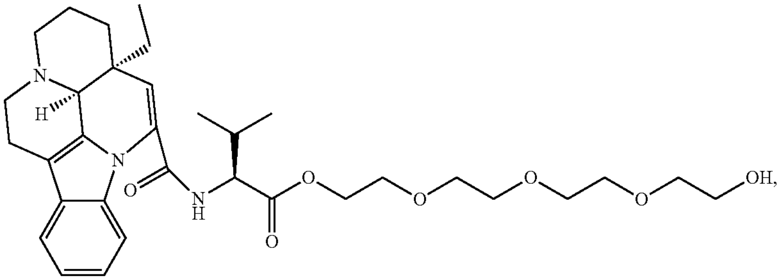,
S31
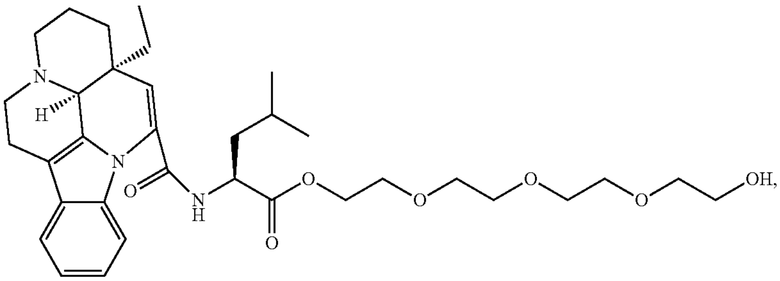,
S32
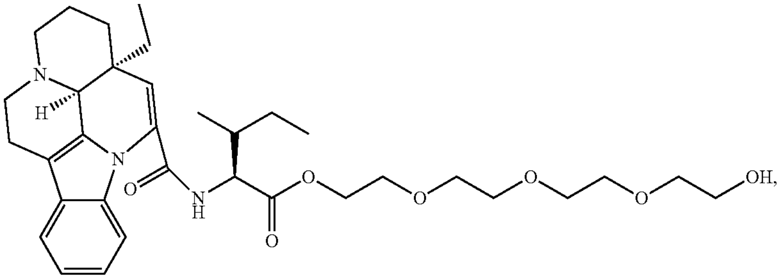,
S33
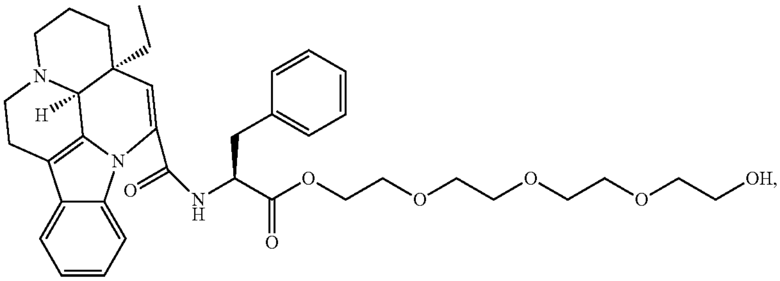,
S34
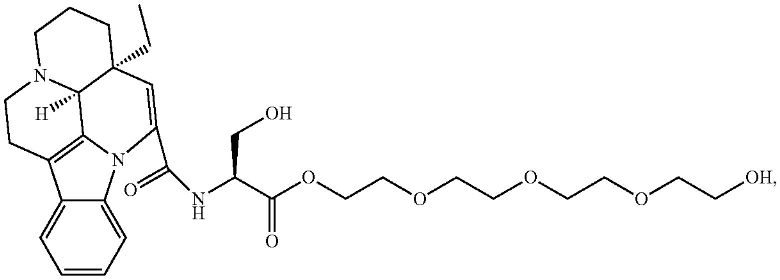, -continued
S35
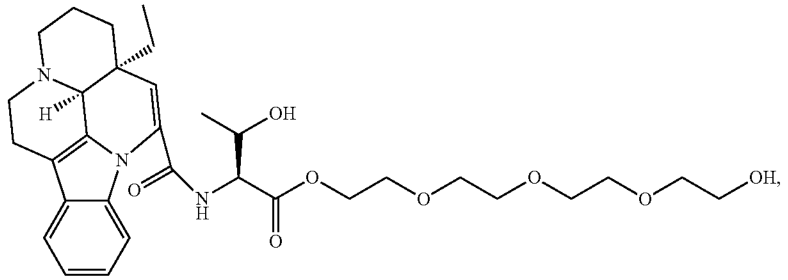
S36
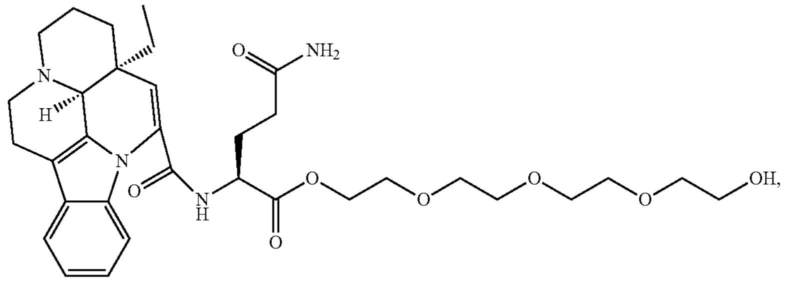
S37
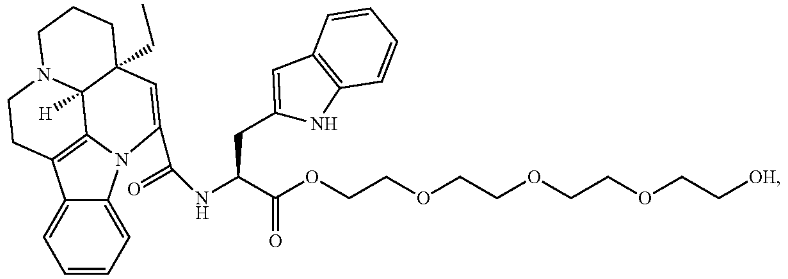
S38
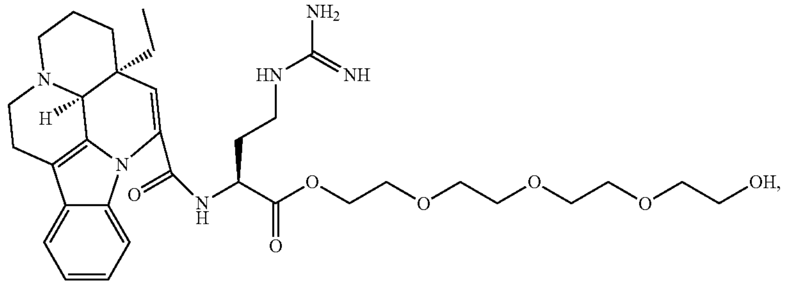
S39
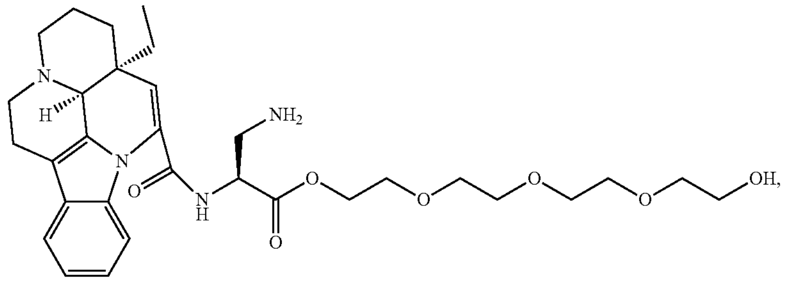

-continued
S40
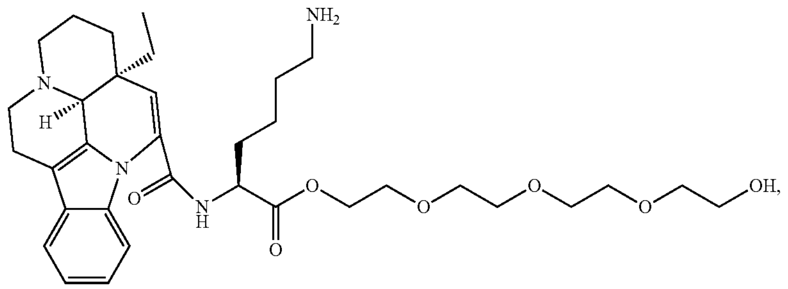
S41
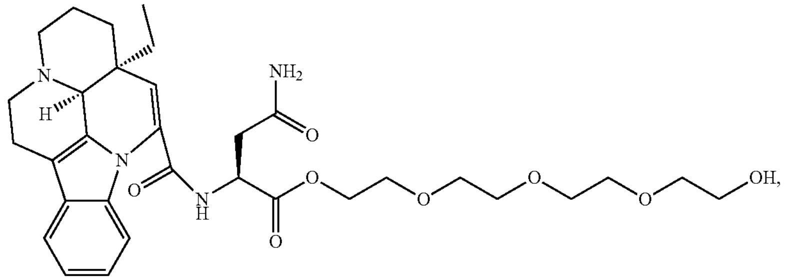
S42
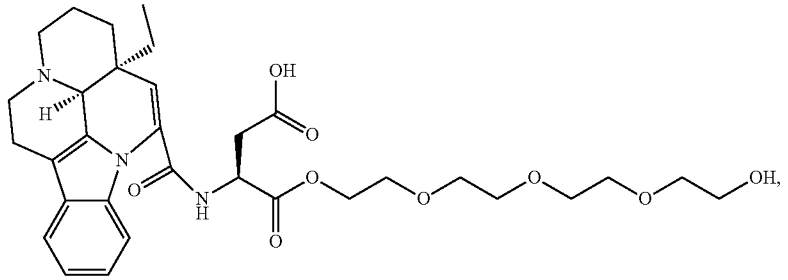
S43
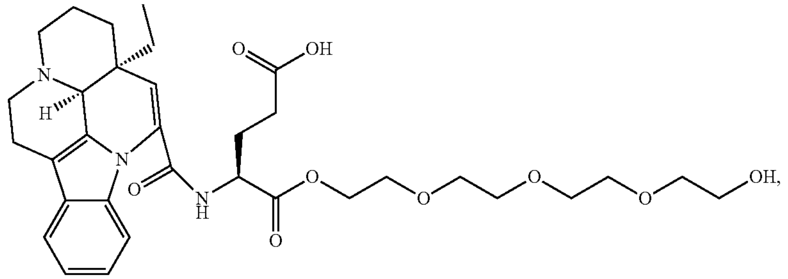
S44
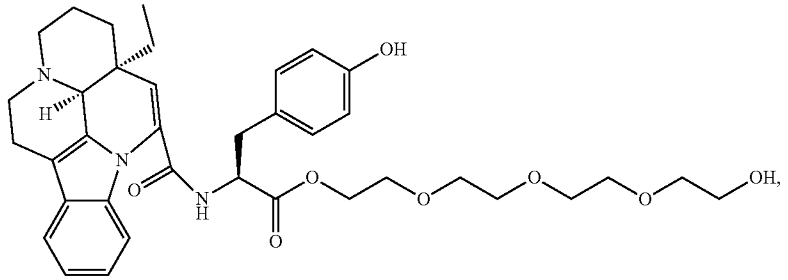

-continued
S45
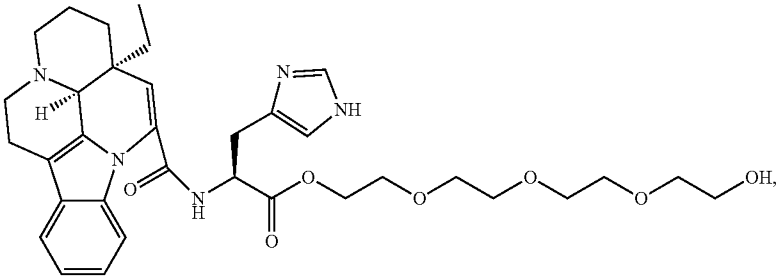
S46
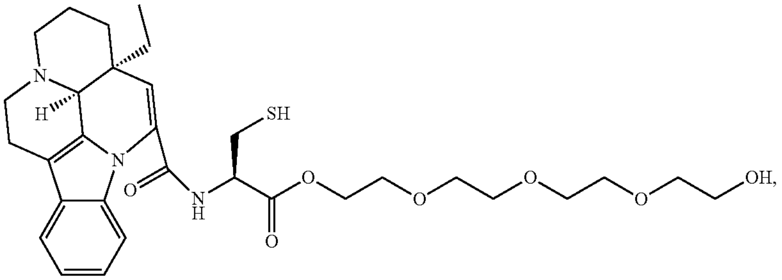
S47
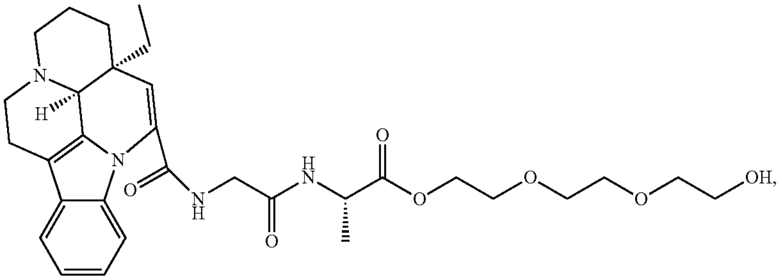
S48
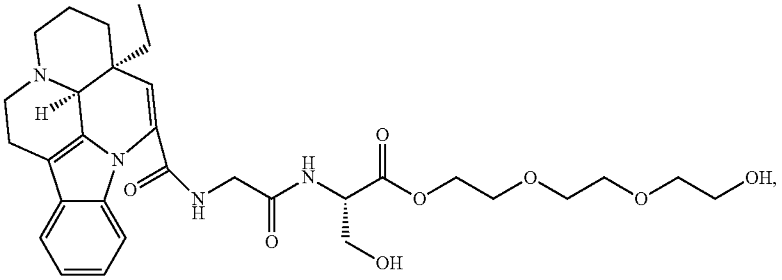
S49
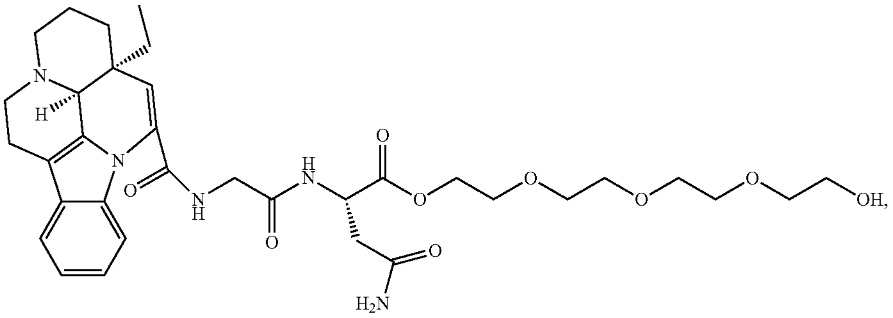

-continued
S50
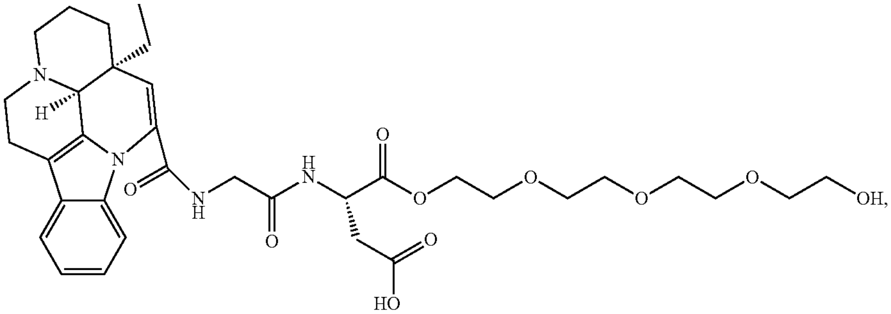
S51
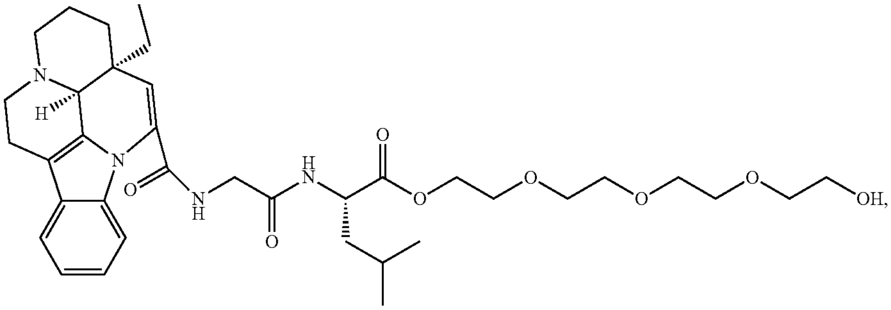
S52
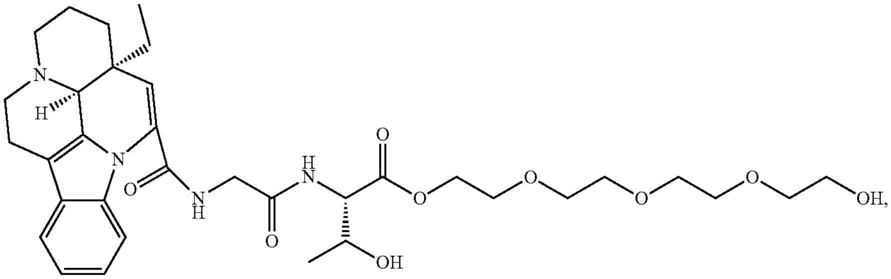
S53
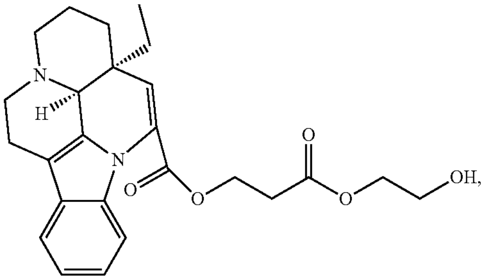
S54
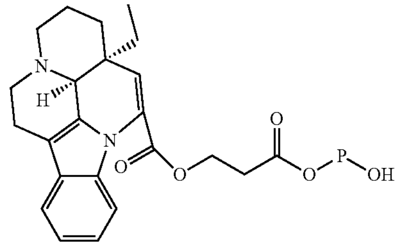
P = PEG-4000,
S55
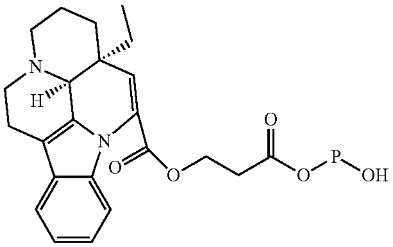
P = PEG-2000,
S56
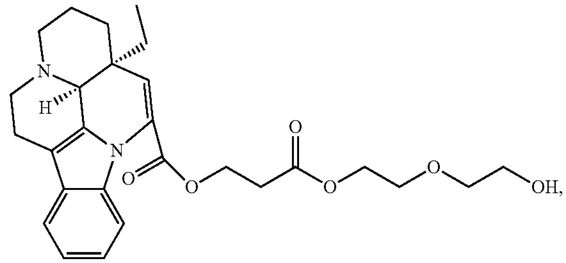

-continued
S57
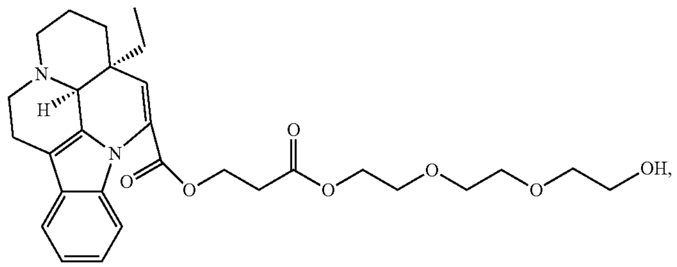
S58
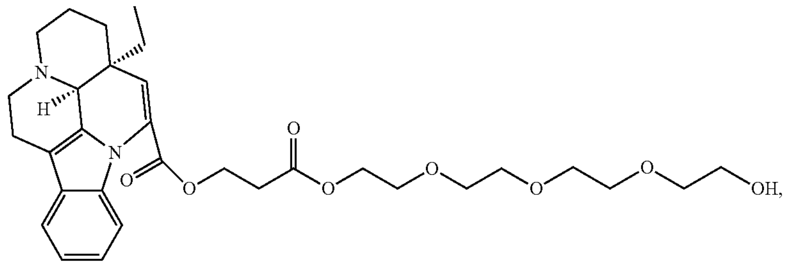
S59
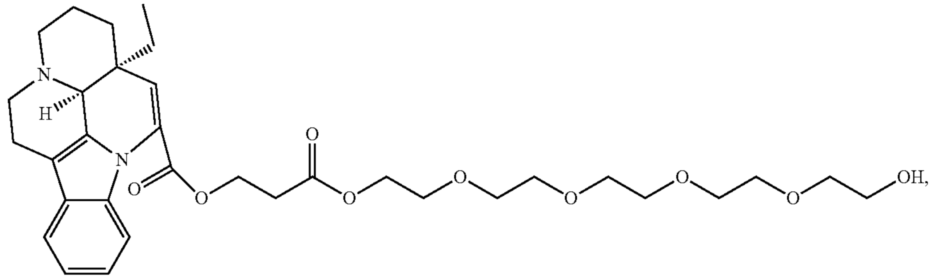
S60
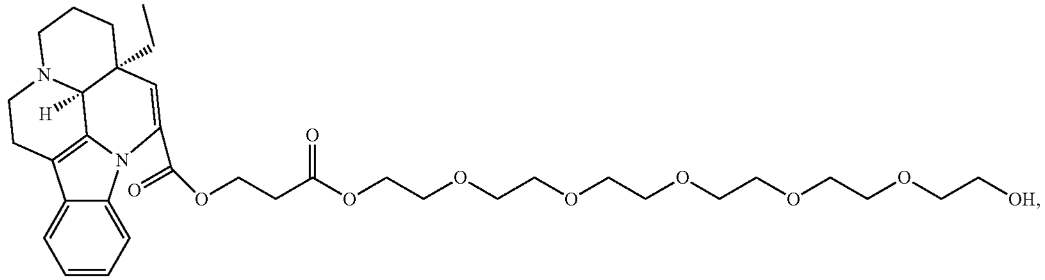
S61
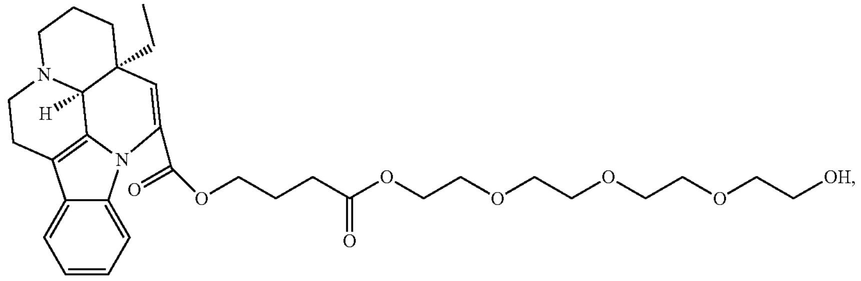

-continued
S62
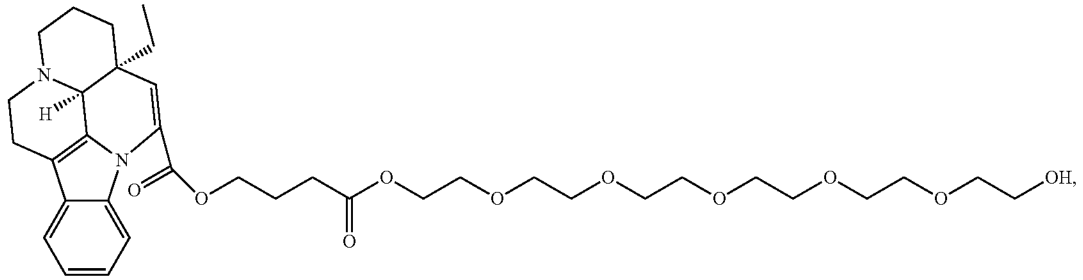
S63
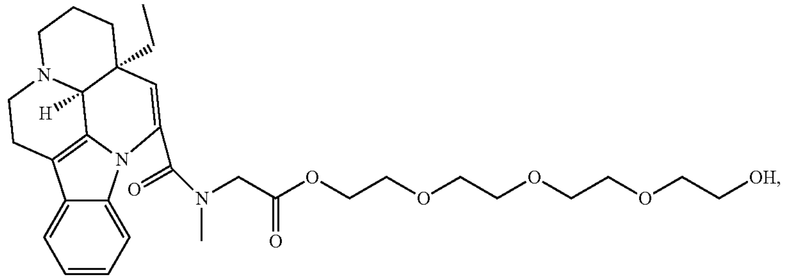
S64
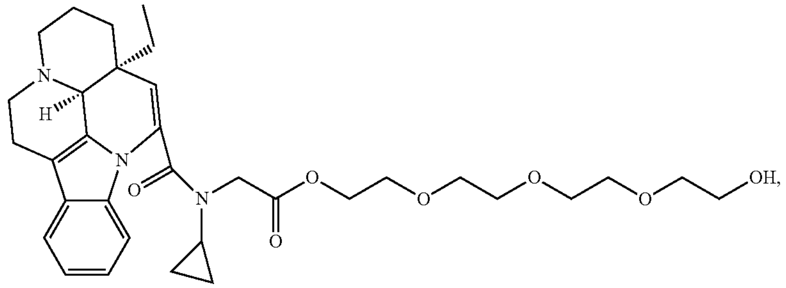
S65
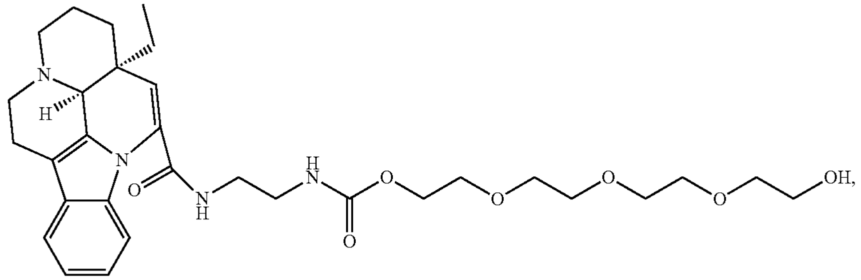
S66
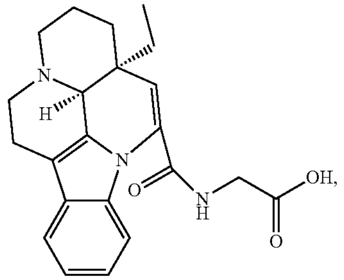
S67
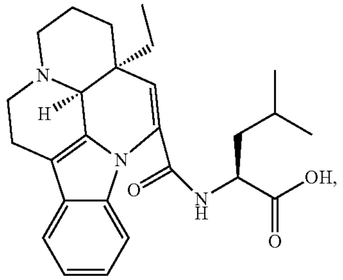

-continued
S68
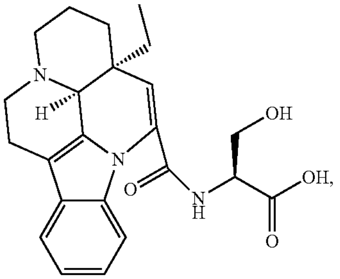
S69
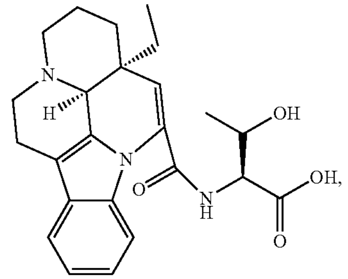
S70
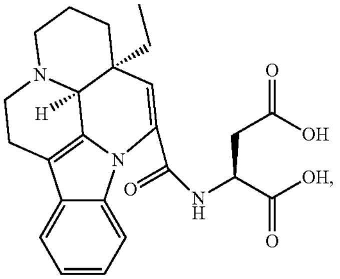
S71
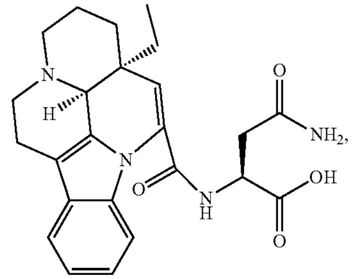
S72
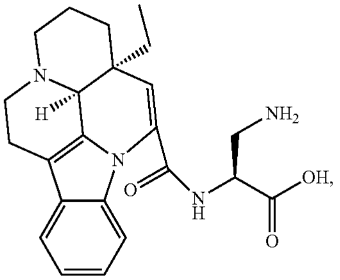
S73
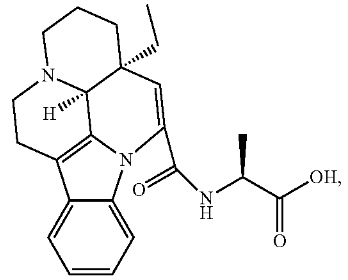
S74
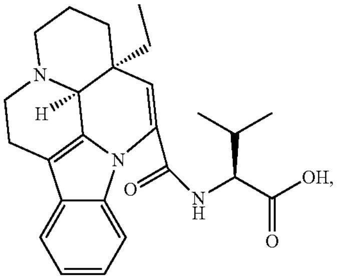
S75
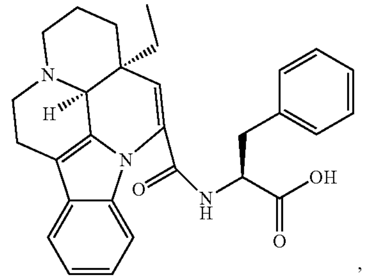
,
S76
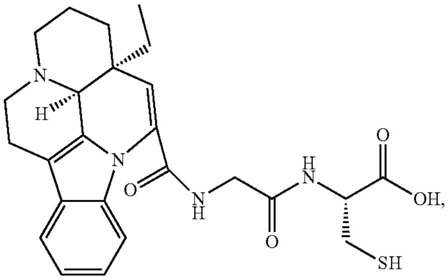
S77
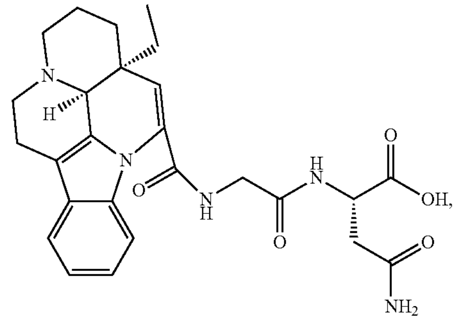

-continued
S78
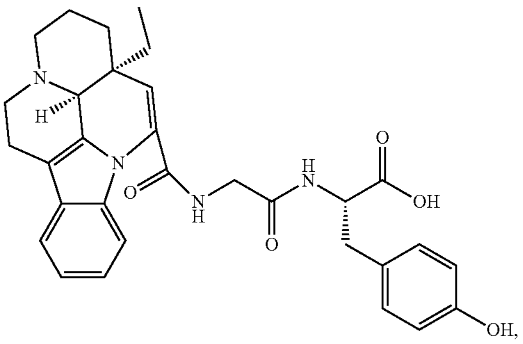
S79
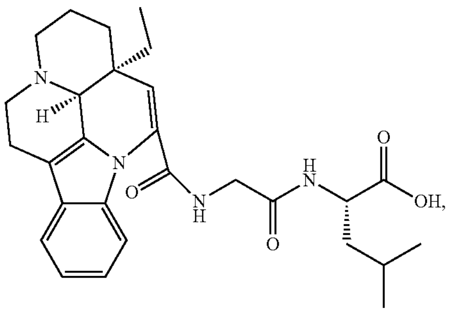
S80
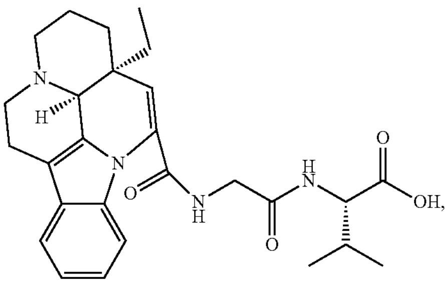
S81
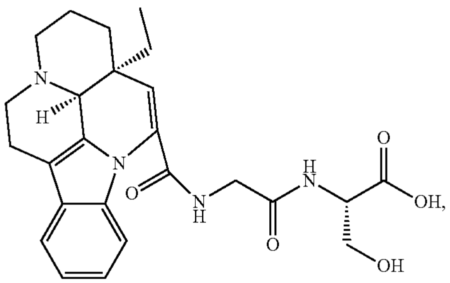
S82
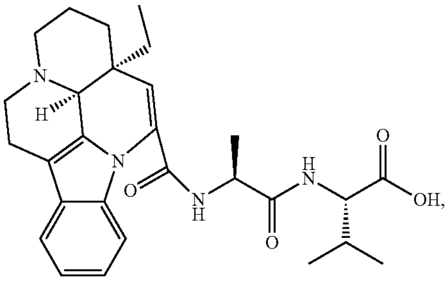
S83
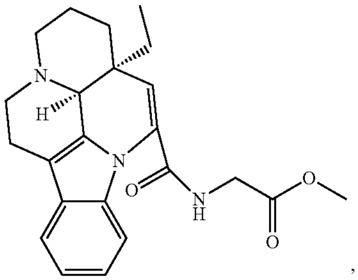
,
S84
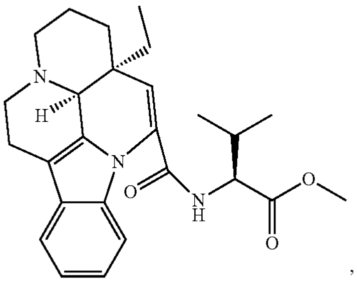
,
S85
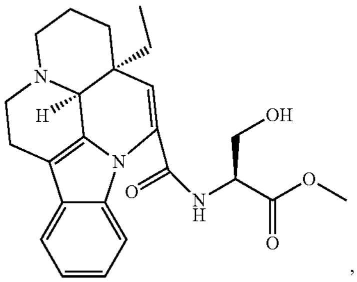
,
S86
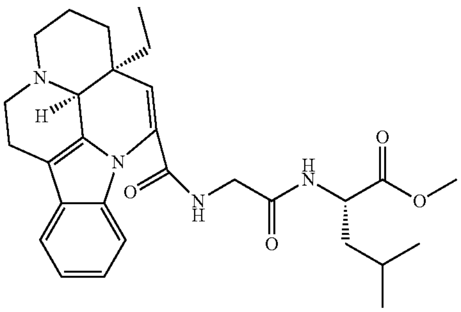
and
S87
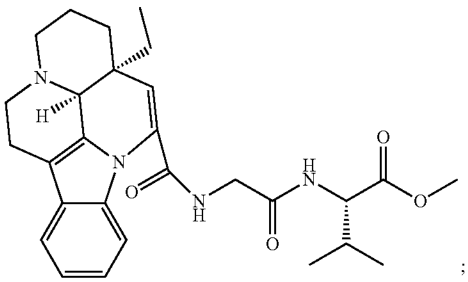
;
wherein the disease is selected from the group consisting of type 1 diabetes, type 2 diabetes, diabetic peripheral neuropathy, diabetic foot and pulmonary fibrosis disease.
9. The compound according to claim 1, wherein the compound is prepared by the following step of: in a solvent, under the action of a base and a condensing agent, subjecting a compound as shown in formula II and a compound as shown in formula III to a condensation reaction as shown below;

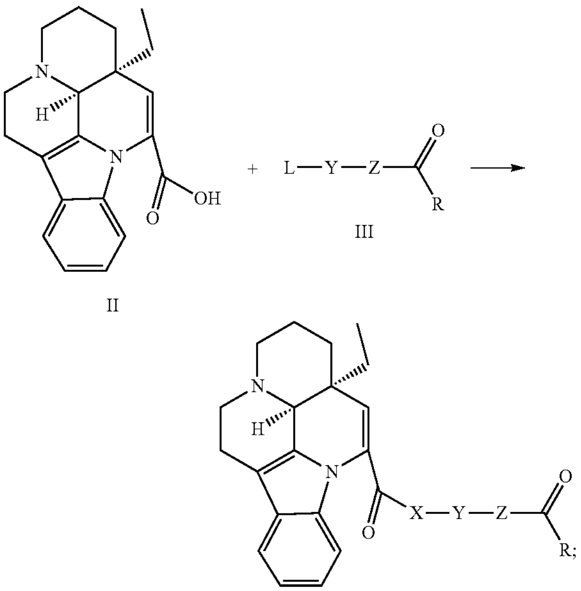

II

III

I wherein, L is $-NHR_1$, hydroxyl

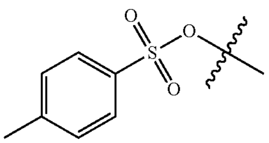

or

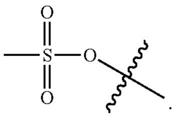.

10. The compound according to claim 9, wherein the solvent is an amide solvent or a halogenated alkane solvent;

and/or, the base is an organic base or an inorganic base;

and/or, the condensing agent is a carbodiimide, an organophosphorus salt or an onium salt.

11. A pharmaceutical composition comprising a compound represented by formula I, or the pharmaceutically acceptable salt thereof, or ane isomer thereof, and a pharmaceutical excipient;

wherein the formula I is shown as follows:

I

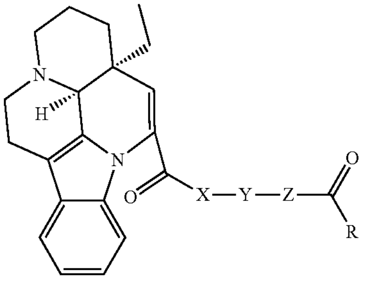

in the formula:

X is O or $-NR^1$;

$R^1$ is hydrogen, unsubstituted or $R^{1-1}$ substituted $C_{1-6}$ alkyl, $C_{6-10}$ aryl, $C_{3-10}$ cycloalkyl, 5-10 membered heteroaryl, or 4-10 membered heterocycloalkyl, and $C_{3-10}$ cycloalkyl-($C_{1-4}$ alkyl)- or $C_{6-12}$ aryl-($C_{1-4}$ alkyl)-;

$R^{1-1}$ is halogen or hydroxyl;

Y is $-(CH_2)_m-$;

m is an integer from 1 to 6;

Z is a single bond,

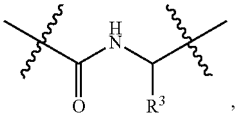,
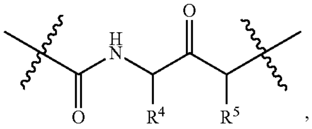,
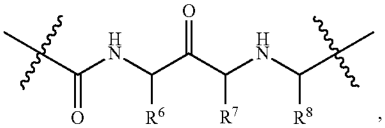,
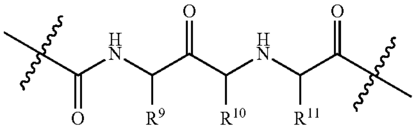 or
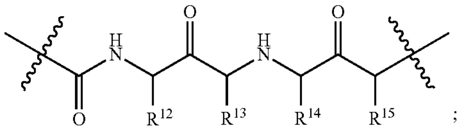;

$R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from hydrogen, unsubstituted or $R^{3-1}$ substituted $C_{1-6}$ alkyl, $C_{6-10}$ aryl, unsubstituted or $R^{3-2}$ substituted $C_{6-12}$ aryl-($C_{1-4}$ alkyl)-, heteroaryl, or heteroaryl-($C_{1-4}$ alkyl)-; and the heteroaryl is 5-10 membered heteroaryl;

$R^{3-1}$ is hydroxyl, carboxyl, amino, sulfhydryl, $-(C{=}O)NR^{3-1-1}$, or $-NH(C{=}NH)NH_2$;

$R^{3-1-1}$ is hydrogen or $C_{1-4}$ alkyl;

$R^{3-2}$ is halogen or hydroxyl;

R is hydrogen, hydroxyl, $C_{1-6}$ alkoxy or

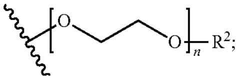;

$R^2$ is $C_{1-6}$ alkyl or hydrogen;

n is an integer from 0 to 500; and

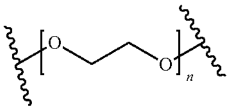

is polyethylene glycol (PEG) with a linear, tree, star or hyperbranched structure comprising $-(OCH_2CH_2)_n$; wherein the tree-shaped PEG is a polymer with a highly symmetrical, tree-like architecture, synthesized layer by layer from a central core to form a precise, multi-branched structure; the star-shaped PEG is a branched polymer architecture in which multiple linear PEG chains emanate from a central core molecule, creating a star-like or radial topology; the hyperbranched PEG is a three-dimensional, globular polymer obtained through a one-step synthesis; it possesses a densely yet irregularly branched structure, lacking the perfect symmetry of dendritic polymers.

12. A method for treating a disease by administrating a compound represented by formula I or a pharmaceutically acceptable salt thereof or an isomer thereof to a subject in need, wherein the disease is selected from the group consisting of type 1 diabetes, type 2 diabetes, diabetic peripheral neuropathy, diabetic foot and pulmonary fibrosis disease;

wherein the formula I is shown as follows:

I

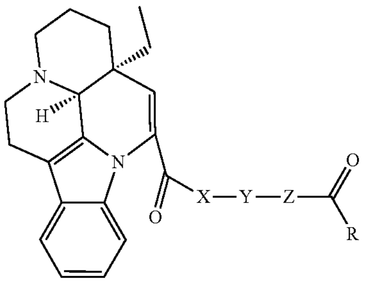

in the formula:

X is O or —$NR^1$;

$R^1$ is hydrogen, unsubstituted or $R^{1-1}$ substituted $C_{1-6}$ alkyl, $C_{6-10}$ aryl, $C_{3-10}$ cycloalkyl, 5-10 membered heteroaryl, or 4-10 membered heterocycloalkyl, and $C_{3-10}$ cycloalkyl-($C_{1-4}$ alkyl)- or $C_{6-12}$ aryl-($C_{1-4}$ alkyl)-;

$R^{1-1}$ is halogen or hydroxyl;

Y is —$(CH_2)_m$—;

m is an integer from 1 to 6;

Z is a single bond,

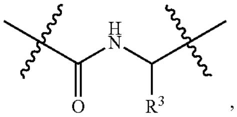

,

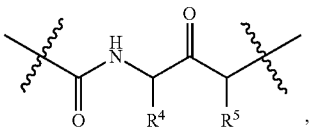

,

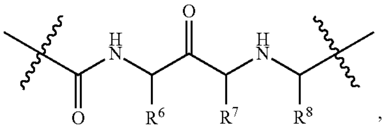

,

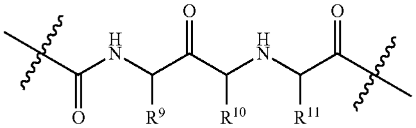

or

-continued

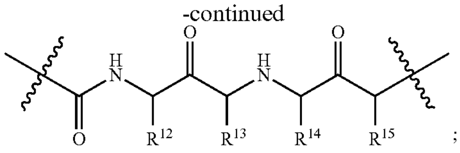

;

$R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently selected from hydrogen, unsubstituted or $R^{3-1}$ substituted $C_{1-6}$ alkyl, $C_{6-10}$ aryl, unsubstituted or $R^{3-2}$ substituted $C_{6-12}$ aryl-($C_{1-4}$ alkyl)-, heteroaryl, or heteroaryl-($C_{1-4}$ alkyl)-; and the heteroaryl is 5-10 membered heteroaryl;

$R^{3-1}$ is hydroxyl, carboxyl, amino, sulfhydryl, —(CO)$NR^{3-1-1}$, or —NH(C═NH)$NH_2$;

$R^{3-1-1}$ is hydrogen or $C_{1-4}$ alkyl;

$R^{3-2}$ is halogen or hydroxyl;

R is hydrogen, hydroxyl, $C_{1-6}$ alkoxy or

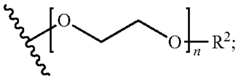

$R^2$ is $C_{1-6}$ alkyl or hydrogen;

n is an integer from 0 to 500; and

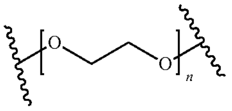

is polyethylene glycol (PEG) with a linear, tree, star or hyperbranched structure comprising —$(OCH_2CH_2)_n$; wherein the tree-shaped PEG is a polymer with a highly symmetrical, tree-like architecture, synthesized layer by layer from a central core to form a precise, multi-branched structure; the star-shaped PEG is a branched polymer architecture in which multiple linear PEG chains emanate from a central core molecule, creating a star-like or radial topology; the hyperbranched PEG is a three-dimensional, globular polymer obtained through a one-step synthesis; it possesses a densely yet irregularly branched structure, lacking the perfect symmetry of dendritic polymers.

13. The method according to claim 12, wherein the compound is prepared as a pharmaceutical composition with a pharmaceutical excipient.

* * * * *